US007662825B2

(12) United States Patent
Baxter et al.

(10) Patent No.: US 7,662,825 B2
(45) Date of Patent: Feb. 16, 2010

(54) N-PYRAZINYL-PHENYLSULPHONAMIDES AND THEIR USE IN THE TREATMENT OF CHEMOKINE MEDIATED DISEASES

(75) Inventors: Andrew Baxter, Loughborough (GB); Timothy Johnson, Loughborough (GB); Nicholas Kindon, Loughborough (GB); Bryan Roberts, Loughborough (GB); Michael Stocks, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 767 days.

(21) Appl. No.: 10/501,510

(22) PCT Filed: Jan. 14, 2003

(86) PCT No.: PCT/SE03/00041

§ 371 (c)(1),
(2), (4) Date: May 25, 2005

(87) PCT Pub. No.: WO03/059893

PCT Pub. Date: Jul. 24, 2003

(65) Prior Publication Data

US 2006/0025423 A1      Feb. 2, 2006

(30) Foreign Application Priority Data

Jan. 16, 2002    (SE)    .................... 0200119
Jun. 17, 2002    (SE)    .................... 0201857

(51) Int. Cl.
A61K 31/4965      (2006.01)
C07D 241/02      (2006.01)

(52) U.S. Cl. .................. 514/255.06; 544/406
(58) Field of Classification Search ............... None
See application file for complete search history.

(56) References Cited

U.S. PATENT DOCUMENTS

| 7,410,972 | B2 | 8/2008 | Baxter et al. | |
| 2002/0143024 | A1 | 10/2002 | Murugesan et al. | 514/258.1 |
| 2006/0122195 | A1* | 6/2006 | Harrison et al. | 514/255.06 |
| 2006/0128723 | A1 | 6/2006 | Mete et al. | |
| 2006/0189613 | A1 | 8/2006 | Cheshire et al. | |
| 2007/0093491 | A1 | 4/2007 | Baxter et al. | |
| 2008/0293742 | A1 | 11/2008 | Cheshire et al. | |

FOREIGN PATENT DOCUMENTS

| EP | 0713875 | 3/2001 |
| EP | 0749964 | 10/2001 |
| GB | 2295616 A | 6/1996 |
| WO | 95/26957 | 10/1995 |
| WO | WO 95/26957 | 10/1995 |
| WO | WO 98/13366 | 4/1998 |
| WO | WO 00/01389 | 1/2000 |
| WO | WO 01/44239 | 6/2001 |
| WO | WO 03/051870 | 6/2003 |
| WO | 2004/007472 | 1/2004 |
| WO | WO 2004/007472 | 1/2004 |
| WO | WO 2004/108690 | 12/2004 |
| WO | WO 2004/108692 | 12/2004 |
| WO | WO 2004/108717 | 12/2004 |
| WO | WO 2005/021513 | 3/2005 |
| WO | WO 2007/035154 | 3/2007 |
| WO | WO 2007/069978 | 6/2007 |

OTHER PUBLICATIONS

Daniels, et. al., Journal of the American Chemical Society (1941), 63, 257-8.*
Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Esche, J. et al., "Reaction products formed by bromometric titration of several sulfonamides of the pyridazine, pyrazine, and pyrazoteseries"; & Arch. Pharm. 1966,299 2,147-53.*
STN International, File CAPLUS, CAPLUS accession No. 2000:34745, Document No. 132:93309, Bristol-Myers Squibb Bo.: "Preparation of N-isoxazolyl biphenylsulfonamides and related compounds as dual angiotension II and endothelin receptor antagonists" & WO, A1, 2000001389, 20000113, see compound with CAS RN 25475-89-9.
STN International, File HCAPLUS, HCAPLUS accession No. 1982:484681: Document No. 97:84681, Kivman, G. Ya. et al: "Penetration of sulfanilamides into inflammatory foci"; & Khim.-Farm. Zh. (1982), 16(6), 665-7.
STN International, File CAPLUS, CAPLUS accession No. 1966:84579, Document No. 64:84579, Esche, J. et al.: "Reaction products formed by bromometric titration of several sulfonamides of the pyridazine, pyrazine, and pyrazole series"; & Arch. Pharm. (1966), 299(2), 147-53.

* cited by examiner

*Primary Examiner*—James O Wilson
*Assistant Examiner*—Jeffrey H Murray
(74) *Attorney, Agent, or Firm*—Morgan Lewis & Bockius LLP

(57) ABSTRACT

The invention provides N-pyrazinyl-phenyl-sulphonamides of formula (I) for use in the treatment of chemokine mediated diseases. Particularly inflammatory diseases, such as asthma.

(I)

14 Claims, No Drawings

N-PYRAZINYL-PHENYLSULPHONAMIDES AND THEIR USE IN THE TREATMENT OF CHEMOKINE MEDIATED DISEASES

CROSS-REFERENCE TO RELATED APPLICATIONS.

The present application is a U.S. National Phase Application of International Application No. PCT/SE03/00041 (filed Jan. 14, 2003) which claims the benefit of Sweden Application 0200119-6 (filed Jan. 16, 2002) and Sweden Application No. 0201857-0 (filed Jun. 17, 2002).

STATEMENT REGARDING FEDERALLY SPONSORED RESEARCH OR DEVELOPMENT.

Not Applicable.

THE NAMES OF THE PARTIES TO A JOINT RESEARCH AGREEMENT.

Not Applicable.

INCORPORATION-BY-REFERENCE OF MATERIAL SUBMITTED ON A COMPACT DISC.

Not Applicable.

BACKGROUND OF THE INVENTION

1. Field of the Invention

The present invention relates to a sulphonamide compound, processes and intermediates used in their preparation, pharmaceutical compositions containing them and their use in therapy.

2. Description of Related Art

Certain sulphonamide compounds are known in the art, for example see GB2295616, US patent 2002143024, WO 01/44239, EP 749964 and Esche, J; Wojahn, H. Arch. Pharm. (1966), 299(2), 147-153.

Chemokines play an important role in immune and inflammatory responses in various diseases and disorders, including asthma and allergic diseases, as well as autoimmune pathologies such as rheumatoid arthritis and atherosclerosis. These small-secreted molecules are a growing superfamily of 8-14 kDa proteins characterised by a conserved four cysteine motif. At the present time, the chemokine superfamily comprises three groups exhibiting characteristic structural motifs, the Cys-X-Cys (C—X—C), Cys-Cys (C—C) and Cys-X$_3$-Cys (C—X$_3$—C) families. The C—X—C and C—C families have sequence similarity and are distinguished from one another on the basis of a single amino acid insertion between the NH-proximal pair of cysteine residues. The C—X$_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β), Thymus and Activation Regulated Chemokine (TARC, CCL17) and Macrophage Derived Chemokine (MDC, CCL22).

The C—X$_3$—C chemokine (also known as fractalkine) is a potent chemoattractant and activator of microglia in the central nervous system (CNS) as well as of monocytes, T cells, NK cells and mast cells.

Studies have demonstrated that the actions of chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family. These receptors represent good targets for drug development since agents which modulate these receptors would be useful in the treatment of disorders and diseases such as those mentioned above.

BRIEF SUMMARY OF THE INVENTION

The present invention provides N-pyrazinyl-phenyl-sulphonamides of formula I shown below and pharmaceutically acceptable salts thereof, and the use thereof in the treatment of chemokine mediated diseases, particularly inflammatory diseases, such as asthma.

BRIEF DESCRIPTION OF THE SEVERAL VIEWS OF THE DRAWING(S).

Not Applicable.

DETAILED DESCRIPTION OF THE INVENTION

The present invention therefore provides a compound of formula (I) and pharmaceutically acceptable salts, solvates or N-oxides thereof:

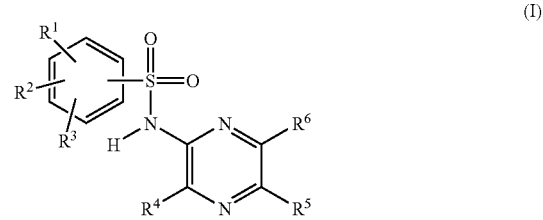

in which:

R$^1$, R$^2$ and R$^3$ are independently hydrogen, halogen, cyano, CF$_3$, OCF$_3$, OC$_{1-6}$ alkyl or C$_{1-6}$ alkyl;

R$^4$ is halogen, CO$_2$R$^{12}$,

C$_{1-6}$ alkoxy where the allyl group may form a 3-6 membered saturated ring or may be substituted with 1-3 fluorine atoms or a cyano group;

C$_{3-6}$ alkenyloxy or C$_{3-6}$ alkynyloxy where either may be optionally substituted with hydroxy or NR$^{14}$R$^{15}$;

OC$_{1-6}$ alkyl-X—C$_{1-6}$ alkyl where the alkyl groups may form a 3-6 membered saturated ring;

OC$_{1-6}$ alkylR$^{11}$, or OC$_{2-6}$ alkyl-X—R$^{11}$ where the alkyl group may form a 3-6 membered saturated ring and is optionally substituted with 1-3 groups selected from hydroxy, halogen, NR$^{14}$R$^{15}$, SR$^{13}$, S(O)$_2$R$^{13}$, S(O)R$^{13}$ or COR$^{13}$;

OC$_{1-6}$ alkylR$^{16}$;

R$^5$ and R$^6$ are independently hydrogen, cyano, halogen, CO$_2$R$^{12}$, CONR$^{14}$R$^{15}$;

$C_{1-6}$ alkyl optionally substituted by hydroxy, $NR^{14}R^{15}$, or 1-3 fluorines;
$C_{1-6}$ alkyl$R^{11}$ or $XCH(R^{11})C_{1-6}$ alkyl or $XCH(R^{16})C_{1-6}$ alkyl where the alkyl group may be optionally substituted with 1-3 groups selected from hydroxy, and $NR^{14}R^{15}$;
$NR^{14}R^{15}$; $N(R^{11})R^{11}$; $X-(CH_2)qNR^{14}R^{15}$; $(CH_2)nNR^{14}R^{15}$; $NHC(O)C_{1-6}$ alkyl optional substituted by one or more hydroxy groups,
$C_{3-6}$ alkynyl or $C_{3-6}$ alkenyl optionally branched and optionally substituted with 1-3 groups is selected from hydroxy, cyano, halogen and =O;
$R^{11}$; $X-R^{11}$; $X-R^{12}$; $X-C_{1-6}$alkyl$R^{16}$; $X-R^{16}$; $X-(CH_2)nCO_2R^{12}$; $X-(CH_2)nCONR^{14}R^{15}$; $X-(CH_2)nR^{11}$; $X-(CH_2)nCN$; $X-(CH_2)qOR^{12}$; $(CH_2)nOR^{12}$; $(CH_2)n-X-R^{11}$; $X-(CH_2)qNHC(O)NHR^{12}$; $X-(CH_2)qNHC(O)R^{12}$; $X-(CH_2)qNHS(O)_2R^{12}$; $X-(CH_2)qNHS(O)_2R^{11}$; $X-C_{3-6}$alkenyl; $X-C_{3-6}$alkynyl;
n is 1, 2, 3, 4 or 5;
q is 2, 3, 4, 5 or 6;
X is $NR^{13}$, O, S, S(O), S(O)$_2$;
$R^{11}$ is an aryl group or a 5-7 membered heteraromatic ring containing 1-4 heteroatoms selected from nitrogen, oxygen or sulphur each of which can be optionally substituted by 1-3 groups selected from halogen, $C(O)NR^{14}R^{15}$, $C(O)OR1^2$, hydroxy, =O, =S, CN, $NO_2$, $COR^{13}$, $NR^{14}R^{15}$, $X(CH_2)qNR^{14}R^{15}$, $(CH_2)nNR^{14}R^{15}$, $(CH_2)nOH$, $SR^{13}$, $S(O)_2R^{13}$ $C_{1-6}$ alkyl-$X-C_{1-6}$ alkyl, $C_{1-6}$ alkyl or $C_{1-6}$ alkoxy where the alkyl group may form a 3-6 membered ring or is optionally substituted with 1-3 groups selected from hydroxy, halogen, $NR^{14}R^{15}$, $SR^{13}$ $S(O)R^{13}$, $S(O)_2R^{13}$;
$R^{12}$ and $R^{13}$ are independently hydrogen or $C_{1-6}$ alkyl where the alkyl group may be substituted with 1-3 fluorine atoms or may form a saturated 3-6 membered ring;
$R^{14}$ and $R^{15}$ are independently hydrogen, $C_{1-6}$ alkyl, $C_{3-6}$ cycloalklyl or $(CH_2)qOH$,
or $R^{14}$ and $R^{15}$ together with the nitrogen atom to which they are attached form a 4-8 membered saturated ring containing 1-3 heteroatoms selected from nitrogen, oxygen and sulphur and optionally substituted by $C_{1-6}$ alkyl, $C_{1-6}$ alkyl-OH, or hydroxy; and
$R^{16}$ is a 4-8 membered saturated ring containing 1-3 heteroatoms selected from nitrogen, oxygen or sulphur and optionally substituted with 1-3 groups selected from hydroxy, cyano, halogen and =O,
provided that:
when $R^4$ is halogen or $C_{1-4}$alkoxy and $R^5$ is hydrogen, halogen, $C_{1-4}$alkyl, $C_{1-2}$alkoxy, $C_{1-2}$alkylthio, trifluoromethyl or ethynyl and when one of $R^1$, $R^2$ or $R^3$ is $C_{1-6}$alkyl or $C_{1-6}$alkoxy and is meta to the sulphonamide group then the group ortho to both the sulphonamide group and the $C_{1-6}$alkyl or $C_{1-6}$alkoxy group is not hydrogen,
when $R^4$ is halogen or $C_{1-4}$alkoxy and $R^5$ is hydrogen, halogen, $C_{1-4}$alkyl, $C_{1-2}$alkoxy, $C_{1-2}$alkylthio, trifluoromethyl or ethynyl and when one of $R^1$, $R^2$ or $R^3$ is $C_{1-6}$alkyl or $C_{1-6}$alkoxy and is ortho to the sulphonamide group then the group ortho to the $C_{1-6}$Alkyl or $C_{1-6}$alkoxy and also meta to the sulphonamide group is not hydrogen,
when two of $R^1$, $R^2$, $R^3$ are hydrogen and the other is a methyl group para to the sulphonamide and $R^4$ is methoxy then $R^5$ is not hydrogen or bromo, and
when $R^5$ is methyl and $R^6$ is methoxy and one of $R^1$, $R^2$ or $R^3$ is bromo or iodo and the other two are both hydrogen, then the bromo or iodo group is not ortho to the sulphonamide group.

The term aryl includes phenyl and naphthyl. The term alkyl, whether alone or as part of another group, includes straight chain and branched chain alkyl groups. Examples of 5- to 7-membered heteroaromatic ring containing 1 to 4 heteroatoms include thienyl, furanyl, pyrrolyl, imidazolyl, pyridyl, pyrazinyl, pyrimidyl, pyridazinyl, triazinyl, oxazolyl, thiazolyl, isoxazolyl, pyrazolyl, oxadiazolyl, thiadiazolyl, triazolyl and tetrazolyl. Examples of saturated 4- to 8-membered rings containing 1 to 3 heteroatoms include morpholine, piperidine and azetidine. Substituents on any rings can be present in any suitable ring position including suitable substituents on nitrogen atoms.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Preferred halogen groups for $R^1$, $R^2$ and $R^3$ are chloro, bromo and fluoro. Preferably one of $R^1$, $R^2$ and $R^3$ is hydrogen and the other is chloro, bromo or methyl. More preferably $R^1$ and $R^2$ are chloro at the 2- and 3-positions of the phenyl ring and $R^3$ is hydrogen (i.e. 2,3-dichlorophenyl), $R^1$ and $R^3$ are chloro at the 2- and 4-positions of the phenyl ring and $R^2$ is hydrogen (i.e. 2,4-dichlorophenyl) or $R^1$ is chloro at the 2-position and $R^2$ is methyl at the 3-position of the phenyl ring and $R^3$ is hydrogen (i.e 2-chloro-3-methylphenyl). Most preferably $R^1$ and $R^2$ are chloro at the 2- and 3-positions of the phenyl ring and $R^3$ is hydrogen (i.e. 2,3-dichlorophenyl).

In a further aspect the invention provides a compound of formula (I) as defined above but without the provisos where $R^1$ and $R^2$ are chloro at the 2- and 3-positions of the phenyl ring and $R^3$ is hydrogen (i.e. 2,3-dichlorophenyl), $R^1$ and $R^3$ are chloro at the 2- and 4-positions of the phenyl ring and $R^2$ is hydrogen (i.e. 2,4-dichlorophenyl) or $R^1$ is chloro at the 2-position and $R^2$ is methyl at the 3-position of the phenyl ring and $R^3$ is hydrogen (i.e 2-chloro-3-methylphenyl).

For the group $R^4$ examples of $C_{3-6}$ alkenyloxy include $OCH_2CH=CH_2$, examples of $C_{3-6}$ alkynyloxy include $OCH_2CCH$, examples of $OC_{1-6}$ alkyl-O-$C_{1-6}$ alkyl include $OCH_2CH_2OMe$, examples of $OC_{1-6}$ alkyl$R^{11}$ include $OCH_2R^{11}$, and examples of $OC_{1-6}$ alkyl$R^{16}$ include $OCH_2$pyrrolidine.

Preferred groups for $R^4$ include $C_{1-6}$ alkoxy such as methoxy, 2-furanylmethoxy, bromo, chloro, 2-methoxyethoxy, (5-methyl-3-isoxazolyl)methoxy, 2-, 3- or 4pyridylmethoxy, 3-pyridazinylmethoxy, methoxy, 2-(1-imidazolyl)ethoxy, (2-methyl4-oxazolyl)methoxy and 4methoxyphenylmethoxy. More preferably $R^4$ is methoxy.

For $R^5$ and $R^6$ examples of $NR^{14}R^{15}$ includes morpholine, pyrrolidine, $NMe_2$, $NHCH_2CH_2OMe$, NHMe, and the groups below:

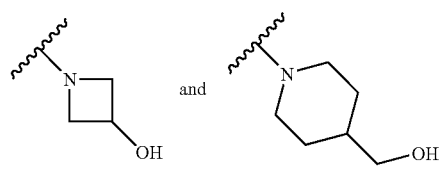

Examples of $X-(CH_2)qNR^{14}R^{15}$ include $SCH_2CH_2NH_2$ and $SCH_2CH_2NMe_2$, examples of $(CH_2)nNR^{14}R^{15}$ include $CH_2$morpholine, examples of $X-R^{12}$ includes SMe, OMe, OEt, OH, $SO_2Me$, examples of $X-C_{1-6}$alkyl$R^{16}$ includes $OCH_2$pyrrolidine, examples of $X-(CH_2)nCO_2R^{12}$ includes SCH$_2$CO$_2$H, SCH$_2$CO$_2$Me, SCH$_2$CH$_2$CO$_2$Me, examples of X—(CH$_2$)nCONR$^{14}$R$^{15}$ includes SCH$_2$CONH$_2$, SCH$_2$CONHMe, OCH$_2$CONEt$_2$, examples of X—(CH$_2$)nR$^{11}$ includes the groups below:

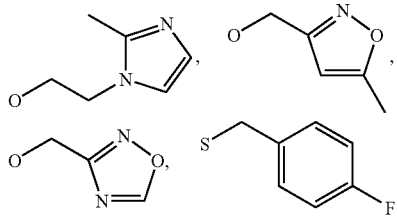

Examples of X—(CH$_2$)$_n$CN, includes SCH$_2$CN, examples of X—(CH$_2$)qOR$^{12}$ includes OCH$_2$CH$_2$OMe, examples of (CH$_2$)nOR$^{12}$ includes CH$_2$OH, CH$_2$OMe, examples of X—(CH$_2$)qNHC(O)NHR$^{12}$ includes SCH$_2$CH$_2$NHC(O)NHEt, and examples of X—(CH$_2$)qNHC(O)R$^{12}$ includes NHCH$_2$CH$_2$NHC(O)Me. Examples of NHC(O)C$_{1-6}$ alkyl optionally substituted by one or more hydroxy groups includes NHCOCH$_2$OH.

Preferred groups for R$^5$ include hydrogen, halogen such as bromo and chloro, phenyl, C$_{1-6}$ alkyl such as methyl, CH$_2$OH, cyano and 2-aminothanethiol. More preferably R$^5$ is hydrogen, methyl, CH$_2$OH or halogen such bromo or chloro.

Preferred groups for R$^6$ include hydrogen, C$_{1-6}$ allyl, CH$_2$OH and halogen, more preferably hydrogen, methyl, CH$_2$OH or chloro.

In a further aspect the invention provides a compound of formula (IA):

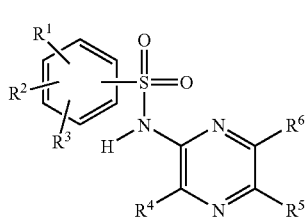

(IA)

in which
R$^1$, R$^2$ and R$^3$ are independently hydrogen, halogen, cyano, CF$_3$, OCF$_3$, C$_{1-6}$ alkenyl or C$_{1-6}$ alkyl;
R$^4$ is halogen, C$_{1-6}$ alkoxy or OR$^9$;
R$^5$ and R$^6$ are independently hydrogen, halogen, C$_{1-6}$ alkoxy, C$_{1-6}$ alkylthio, cyano, R$^9$, OR$^9$, NR$^9$R$^{10}$, SR$^9$, S(CH2)$_n$CO$_2$H, S(CH2)$_n$CO$_2$R$^{12}$, S(CH2)$_n$CONR$^{12}$R$^{13}$, S(CH2)$_n$R$^{11}$ or a 5- to 7-membered heteroaromatic or saturated ring containing 1 to 3 heteroatoms selected from nitrogen, oxygen and sulphur;
n is 1, 2 or 3;
R$^9$ and R$^{10}$ are independently hydrogen, C$_{1-6}$ alkyl optionally substituted by hydroxy, C$_{1-6}$ alkoxy or NHCOC$_{1-6}$ alkyl, or R$^9$ and R$^{10}$ are optionally substituted aryl, C$_{1-6}$ alkyl-aryl or C$_{1-6}$ alkyl-R$^{11}$ or R$^9$ and R$^{10}$ together with the nitrogen atom to which they are attached form a 4- to 8-membered saturated ring containing 1 to 3 heteroatoms selected from nitrogen, oxygen and sulphur and optionally substituted by C$_{1-6}$ alkyl or C$_{1-6}$ alkyl-OH; and
R$^{11}$ is a 5- to 7-membered heteroaromatic ring containing 1 to 3 heteroatoms selected from nitrogen, oxygen and sulphur and optionally substituted by C$_{1-6}$ alkyl; and
R$^{12}$ and R$^{13}$ are independently hydrogen or C$_{1-6}$ alkyl.

For compounds (IA) R$^1$, R$^2$ and R$^3$ are independently hydrogen, halogen, cyano, CF$_3$, OCF$_3$, C$_{1-6}$ alkenyl or C$_{1-6}$ alkyl, preferred halogen groups being chloro. Preferably one of R$^1$, R$^2$ and R$^3$ is methyl, ethenyl, cyano, chloro, fluoro, iodo or two are chloro or all three are fluoro. More preferred are compounds where R$^1$—R$^3$ together with the phenyl group to which they are attached form a 3-chloro-2-methylphenyl or a 2,3-dichlorophenyl group.

For compounds (IA) preferred groups for R$^4$ include halogen such as bromo and chloro, C$_{1-6}$ alkoxy such as methoxy and ethoxy, C$_{1-6}$ alkyl or OR$^9$ where R$^9$ is CH$_2$R$^{11}$ where R$^{11}$ is a 5- or 6-membered heteroaromatic ring containing 1 or 2 heteroatoms.

More preferably R$^4$ is methoxy, halogen, such as chloro, or OR$^9$ where R$^9$ is CH$_2$R$^{11}$ where R$^{11}$ is furanyl, 5-methyl-3-isoxazolyl, pyridyl optionally substituted by methyl, pyridazinyl, pyrazinyl, 1-methyl-6-oxo-1,6-dihydro-3-pyridinyl.

For compounds (IA) preferably R$^5$ is hydrogen, methyl, bromo, chloro, methoxy, morpholinyl, pyrrolinyl, dimethylamino, hydroxy, 2-methoxyethoxy, pyrazinyl, pyrimidinyl, O-Ph-CO$_2$H, 2-hydroxyethylamino, 2-methoxyethylamino, NHCH$_2$CH$_2$NHCOMe, cyano, 4-hydroxymethyl-1-piperidinyl, SMe, NHMe, or 2,4-difluorophenyl.

For compounds (IA) preferably R$^6$ is hydrogen or chloro.

Preferred compounds of formula (I)/(IA) include those exemplified herein both in free base form and as pharmaceutically acceptable salts.

According to the invention there is also provided a process for the preparation of compound (I) which comprises reaction of a compound of formula (II):

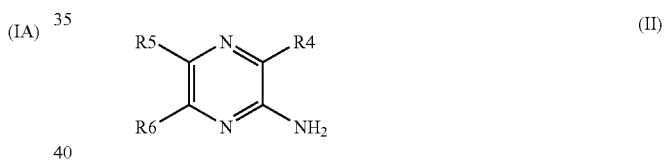

(II)

where R$^4$, R$^5$ and R$^6$ are as defined in formula (I) or are protected derivatives thereof with a compound of formula (III):

(III)

where R$^1$, R$^2$ and R$^3$ are as defined in formula (I) or are protected derivatives thereof and LG is a leaving group, and optionally thereafter
removing any protecting groups,
forming a pharmaceutically acceptable salt.

Preferred leaving groups LG include halogen such as chloro. Preferably the reaction between compounds (II) and (III) is carried out by treating compound (II) with a base such as sodium hydride or potassium tert-butoxide in a suitable solvent such as 1,2-dimethoxyethane or tetrahydrofuran.

Where R$^4$ is C$_{1-6}$ alkoxy where the alkyl group may form a 3-6 membered saturated ring or may be substituted with 1-3 fluorine atoms or a cyano group;

$C_{3-6}$ alkenyloxy or $C_{3-6}$ alkynyloxy where either may be optionally substituted with hydroxy or $NR^{14}R^{15}$;

$OC_{1-6}$ alkyl-X—$C_{1-6}$ alkyl where the alkyl groups may form a 3-6 membered saturated ring;

$OC_{1-6}$ alkylR$^{11}$, or $OC_{2-6}$ alkyl-X—R$^{11}$ where the alkyl group may form a 3-6 membered saturated ring and is optionally substituted with 1-3 groups selected from hydroxy, halogen, $NR^{14}R^{15}$, $SR^{13}$, $S(O)_2R^{31}$, $S(O)R^{13}$; or $OC_{1-6}$ alkylR$^{16}$;

compounds of formula (II) can be prepared by treating a compound of the formula (IV), where LG is a leaving group (such as chlorine or bromine):

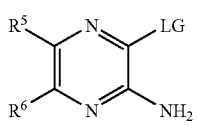

(IV)

with a compound of formula (V)

$R^4$—H  (V)

in a suitable solvent (such as 1,2-dimethoxyethane, N,N-dimethylformamide or tetrahydrofuran) with a suitable base such as sodium hydride or potasssium tert-butoxide at a suitable temperature such as 25° C. to 60° C.

Where $R^4$ is $C_{1-6}$ alkoxy where the alkyl group may form a 3-6 membered saturated ring or may be substituted with 1-3 fluorine atoms or a cyano group;

$C_{3-6}$ alkenyloxy or $C_{3-6}$ alkynyloxy where either may be optionally substituted with hydroxy or $NR^{14}R^{15}$;

$OC_{1-6}$ alkyl-X—$C_{1-6}$ alkyl where the alkyl groups may form a 3-6 membered saturated ring; $OC_{1-6}$ alkylR$^{11}$, or $OC_{2-6}$ alkyl-X—R$^{11}$ where the alkyl group may form a 3-6 membered saturated ring and is optionally substituted with 1-3 groups selected from hydroxy, halogen, $NR^{14}R^{15}$, $SR^{13}$, $S(O)_2R^{13}$, $S(O)R^{13}$; or $OC_{1-6}$ alkylR$^{16}$;

compounds of formula (I) can be prepared by treating a compound of the formula (VI), where LG is a leaving group (such as chlorine or bromine):

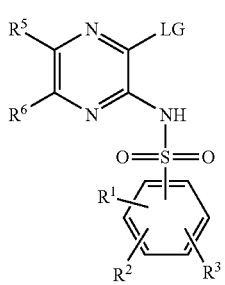

(VI)

with a compound of formula (V)

in a suitable solvent (such as 1,2-dimethoxyethane, N,N-dimethylformamide or tetrahydrofuran) with a suitable base such as sodium hydride or potasssium tert-butoxide at a suitable temperature such as 25° C. to 60° C.

Compounds of structure (VIII) can be prepared by taking a compound of formula (VII) where LG is a leaving group (such as chlorine or bromine) and protecting the sulfonamide as for example the trimethylsilyethoxymethyl ether (SEM) or methoxymethyl ether (MOM) by the standard literature methods (such as SEM-chloride or MOM-chloride) in a suitable solvent (such as tetrahydrofuran) with a suitable base (such as triethylamine) at a suitable temperature (such as 0-20° C.) to afford compound of the formula (VIII):

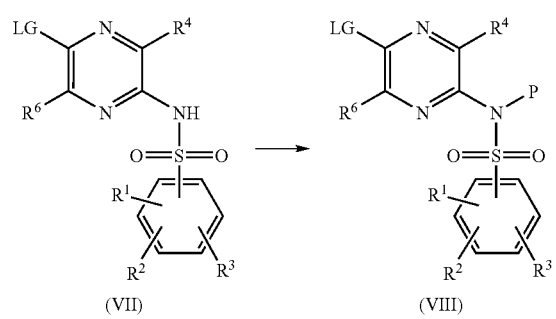

(VII) (VIII)

Compound of formula (VIII) could then be treated with compounds of formulae (IX):

$R^5$—H  (IX)

where $R^5$—H is a primary or secondary amine, thiol or alcohol as defined above (i.e. where $R^5$ is a group containing an X moiety where X is $NR^{13}$, O or S), in a suitable solvent (such as tetrahydrofuran or acetonitrile) with or without a suitable base (such as sodium hydride, caesium carbonate or triethylamine) at a suitable temperature ranging from 25-85° C. to afford compound of the formula (X):

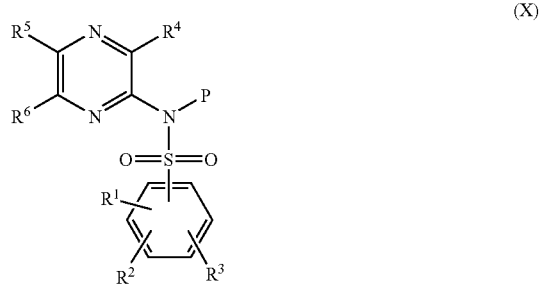

(X)

The protecting group (P) can then be removed by standard methods to afford compound of formula (1).

Compounds of structure (11) or (1), where $R^5$ is an optionally substituted aryl or heteroaryl ring as defined in the claims, can be prepared by taking a compound of formula (XI) or (VII) where LG is a suitable leaving group such as bromine, chlorine or iodine and reacting it with an aryl or heteroaryl boronic acid such as phenyl boronic acid, a palladium catalyst such as [1,1'-bis(diphenylphosphino)ferrocene]palladium (11) chloride, a suitable base such as caesium fluoride, sodium acetate or caesium carbonate and a suitable solvent such as methanol or ethanol and heating between 40-80° C.

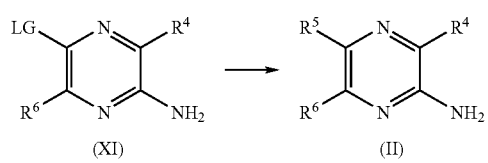

(XI) (II)

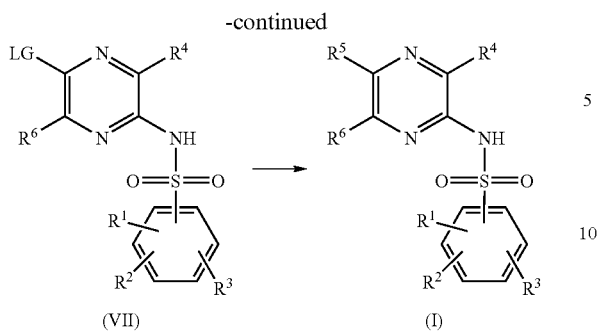

(VII)        (I)

Compounds of formula (11) and (1) where $R^5$ or R6 is $CO_2R^{13}$ can be prepared by reacting a compound of formula (11) or (1), where $R^5$ or $R^6$ is bromine or iodine, in a suitable solvent such as $R^{13}$ OH or dioxane containing $R^{13}OH$, a suitable tertiary amine such as triethylamine, a suitable palladium catalyst such as [1,1'-bis(diphenylphosphino)ferrocene]palladium (11) chloride under an atmosphere of carbon monoxide usually at 2-10 bar, ideally at 46 bar and at a temperature of 70-120° C. Compounds of formula (11) and (1) where $R^5$ or $R^6$ is $CONR^{14}R^{15}$ can be prepared by reacting a compound of formula (11) or (1), where $R^5$ or $R^6$ is bromine or iodine, in a suitable solvent such as dioxane containing $NHR^{14}R^{15}$, a suitable tertiary amine such as triethylamine, a suitable palladium catalyst such as [1,1'-bis(diphenylphosphino)ferrocene]palladium (11) chloride under an atmosphere of carbon monoxide usually at 2-10 bar, ideally at 4-6 bar and at a temperature of 70-120 ° C. Compounds of formula (1) where $R^5$ or $R^6$ is $CH_2OH$ can be prepared from compounds of formula (1) where $R^5$ or $R^6$ is $CO_2R^{13}$ by reduction using a suitable reducing agent such as lithium triethylborohydride in a suitable solvent such as tetrahydrofuran at a temperature of 0-10° C.

Compounds of formula (1) where $R^5$ or $R^6$ is CHO can be prepared from compounds of formula (1) where $R^5$ or $R^6$ is $CH_2OH$ by oxidation using a suitable oxidising agent such as manganese dioxide or pyridinium chlorochromate (PCC) in a suitable solvent such as tetrahydrofuran or dichloromethane at a temperature of 0-50° C.

Compounds of formula (1) where $R^5$ or $R^6$ is $CH(OH)R^{11}$ or CH(OH)(C1-5)alkyl can be prepared from compounds of formula (1) where $R^5$ or $R^6$ is CHO by reaction with a compound of formula (XII) where M is a metal such as magnesium or lithium in a suitable solvent such as tetrahydrofuran or diethyl ether at a temperature of 0-10° C.

$C_{1-5}$ alkylM or $R^{11}M$ (XII)

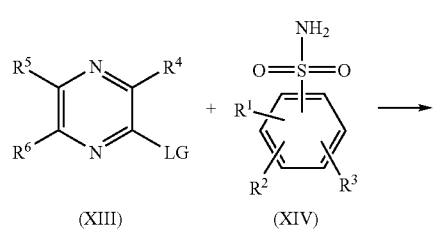

(XIII)        (XIV)

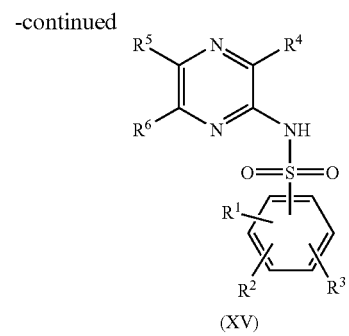

(XV)

A compound of formula (XV) can be made by reacting a compound of formula (XIII), where $R^4$ is preferrably chloro, bromo or alkoxy and LG is a suitable leaving group such as chloro or bromo, with a compound of formula (XIV) using a suitable base such as potassium carbonate or caesium carbonate in a suitable solvent such as N)N-dimethylformamide at a temperature of 40-90° C.

Intermediate compounds of formula (II) and (III) can be prepared using standard chemistry or are available commercially.

It will be appreciated by those skilled in the art that in the processes of the present invention certain functional groups such as hydroxyl or amino groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley—Interscience (1991).

The compounds of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

Certain compounds of formula (II) and (III) are believed to be novel and form a further aspect of the invention.

The compounds of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

The compounds of formula (I) has activity as pharmaceuticals, in particular as modulators of chemokine receptor (especially CCR4) activity, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) gout, rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) pruritis, scleroderma, otitus, psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis, lupus;

(4) (gastrointestinal tract) Coeliac disease, proctitis, eosinopilic gastro-enteritis, mastocytosis, inflammatory bowel diseases such as Crohn's disease, ulcerative colitis, ileitis and enteritis, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal diorders, e.g. tropical spastic paraparesis, and stiff-man syndrome: paraneoplastic syndromes, e.g. cerebellar degeneration and encephalomyelitis; CNS trauma; migraine; stroke and correctum diseases such as meningitis (6) (other tissues and systemic disease) hepatitis, vasculitis, spondyloarthopathies, vaginitis, glomerulonephritis, myositis, atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) (allograft and xenograft rejection) acute and chronic following, for example, transplantation of kidney, heart, liver, lung, bone marrow, skin and cornea; and chronic graft versus host disease;

(8) Cancer, carcinoma & tumour metastasis, including that of the bladder, breast, colon, kidney, liver, lung, ovary, pancreas, stomach, cervix, thyroid and skin, especially non-small cell lung cancer (NSCLC), malignant melanoma, prostate cancer and squamous sarcoma. Hematopoietic tumors of lymphoid lineage, including acute lymphocytic leukemia, B cell lymphoma and Burketts lymphoma, Hodgkins Lymphoma, Acute Lymphoblastic Leukemia. Hematopoietic tumors of myeloid lineage, including acute and chronic myelogenous leukemias and promyelocytic leukemia. Tumors of mesenchymal origin, including fibrosarcoma and rhabdomyosarcoma, and other tumors, including melanoma, seminoma, tetratocarcinoma, neuroblastoma and glioma.

(9) All diseases that result from a general inbalance of the immune system and resulting in increased atopic inflammatory reactions.

(10) Cystic fibrosis, re-perfusion injury in the heart, brain, peripheral limbs and other organs.

(11) Burn wounds & chronic skin ulcers

(12) Reproductive Diseases (e.g. Disorders of ovulation, menstruation and implantation, Pre-term labour, Endometriosis)

(13) thrombosis

(14) infectious diseases such as HIV infection and other viral infections, bacterial infections.

Thus, the present invention provides a compound of formula (I), or a pharmaceutically-acceptable salt or solvate thereof, as hereinbefore defined for use in therapy.

Preferably the compound of the invention are used to treat diseases in which the chemokine receptor belongs to the CC chemokine receptor subfamily, more preferably the target chemokine receptor is the CCR4 receptor.

Particular conditions which can be treated with the compound of the invention are asthma, rhinitis and inflammatory skin disorders, diseases in which there are raised TARC, MDC or CCR4 levels. It is preferred that the compound of the invention is used to treat asthma and rhinitis, especially asthma.

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity, particularly CCR4 activity, is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CCR4) receptor, which comprises administering to a patient a therapeutically effective amount of a compound of formula (I), or a pharmaceutically acceptable salt or solvate thereof, as hereinbefore defined.

The invention also provides a method of treating a respiratory disease, such as athma and rhinitis, especially asthma, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compound of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2,-receptor agonists and oral leukotriene receptor antagonists).

The following examples illustrate the invention.

EXAMPLE 1

2,3-Dichloro-N-(3-methoxy-5-methyl-2-pyrazinyl)-benzenesulphonamide

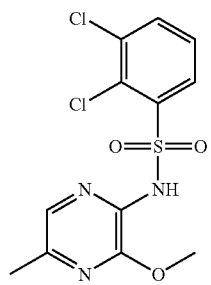

Sodium hydride (0.1 g of 60%) was added to 3-methoxy-5-methyl-2-pyrazinamine (0.07 g) in 1,2-dimethoxyethane (3 mL) under nitrogen at room temperature. After 1 hour at 50°, 2,3-dichlorobenzenesuphonyl chloride (0. 15 g) was added. After stirring for 30 minutes, 5% aqueous citric acid was added and the product extracted with ethyl acetate (X3). The combined extracts were washed with saturated brine, dried (MgSO$_4$) and the solvent was evaporated. Chromatography on silica eluting with dichloromethane/methanol mixtures gave the title compound as a white solid (0.08 g).

m/e 346/8/350 (M−1$^+$, 100%)

$^1$H NMR (D6-DMSO) δ 11.27 (1H, s), 8.06 (1H, d), 7.93 (1H, d), 7.60-7.55 (1H, br s), 7.58 (1H, t), 3.87 (3H, s), 2.28 (3H, s).

EXAMPLE 2

N-(6-Chloro-3-methoxy-2-pyrazinyl)-2,3,4-tifluorobenzenesulphonamide

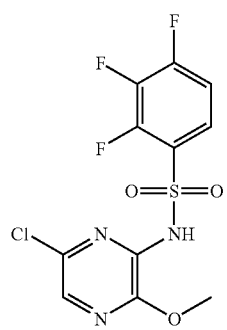

Prepared by the method of Example 1 (reaction performed at room temperature) using 6-chloro-3-methoxy-2-pyrazinamine (0.16 g) and 2,3,4-trifluorobenzenesulphonyl chloride (0.25 g). Yield 0.08 g.

m/e 352/4 (M−1$^+$, 100%)

$^1$H NMR (D6-DMSO) δ 7.93-7.80 (1H, m), 7.89 (1H, s), 7.60-7.50 (1H, m), 3.91 (3H, s).

EXAMPLE 3

3-Chloro-N-(6-chloro-3-methoxy-2-pyrazinyl)-2-methylbenzenesulphonamide

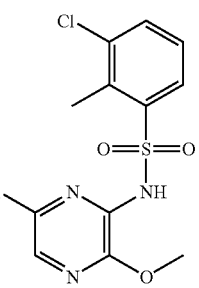

Prepared by the method of Example 1 (reaction performed at room temperature) using 6-chloro-3-methoxy-2-pyrazinamine (0.16 g) and 3-chloro-2-methylbenzenesulphonyl chloride (0.23 g). Yield 0.15 g.

m/e 346/8/50 (M−1$^+$, 100%)

$^1$H NMR (D6-DMSO) δ 8.05 (1H, d), 7.85 (1H, s), 7.75 (1H, d), 7.47 (1t), 3.92 (3H, s), 2.66 (3H, s).

EXAMPLE 4

2,3-Dichloro-N-(6-chloro-3-methoxy-2-pyrazinyl)benzenesulphonamide a) 3-Bromo-6-chloro-2-pyrazinamine

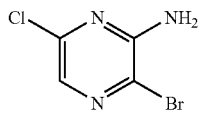

N-bromosuccinamide (6.9 g) was added portionwise over 0.5 h to a stirred solution of 6-chloro-2-pyrazinamine (5.0 g) in chloroform (200 mL) heated under reflux. After the addition was complete the reaction mixture was allowed to cool, washed with water and evaporated to give a 3:1 mixture of 5-bromo-6-chloro-2-pyrazinamine and the subtitle compound which were separated by silica gel chromatography eluting with dichloromethane. Yield 2.0 g. Used directly.

b) 6-Chloro-3-methoxy-2-pyrazinamine and 3-bromo-6-methoxy-2-pyrazinamine

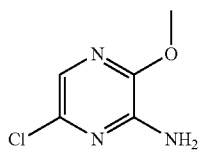

3-Bromo-6-chloro-2-pyrazinamine (1.0 g), sodium methoxide (3 mL of 25% solution in methanol) and methanol (10 mL) were heated at reflux for 3 hours. The solvent was evaporated and the residue was dissolved in ethyl acetate and brine. The organic layer was separated dried (MgSO$_4$) and the solvent was evaporated to give a mixture of the sub-title compounds (ratio 10:1). Purification was by silica gel chromatography eluting with dichloromethane. Yield 0.5 g. Used directly.

c) 2,3-Dichloro-N-(6-Chloro-3-methoxy-2-pyrazinyl)benzenesulphonamide

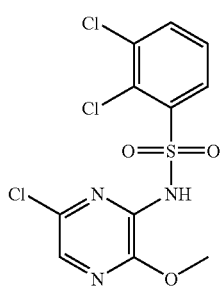

Prepared by the method of Example 1 (reaction performed at room temperature) using 6-chloro-3-methoxy-2-pyrazinamine (0.24 g) and 2,3-dichlorobenzenesulphonyl chloride (0.32 g). Yield 0.24 g.

m/e 366/8/370/2 (M−1$^+$, 100%)

$^1$H NMR (D6-DMSO) δ 8.14 (1H, d), 7.96 (1H, d), 7.89 (1H, s), 7.62 (1H, t), 3.91 (3H, s).

EXAMPLE 5

2,3-Dichloro-N-(5-chloro-3-methoxy-2-pyrazinyl)benzenesulphonamide

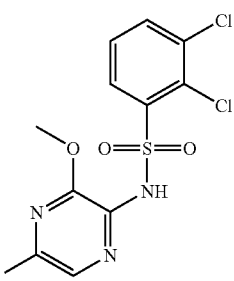

Prepared by the method of Example I (reaction performed at room temperature) using 5-chloro-3-methoxy-2-pyrazinamine (0.1 g) and 2,3-dichlorobenzenesulphonyl chloride (0.15 g). Yield 0.05 g.

m/e 366/8/370/2 (M−1$^+$, 100%)

$^1$H NMR (D6-DMSO) δ 8.15 (1H, d), 7.93 (1H, d), 7.79 (1H, s), 7.58 (1H, t), 3.93 (3H,s ).

EXAMPLE 6

N-(5-Bromo-3-methoxy-2-pyrazinyl)-2,5-dichlorobenzenesulphonamide

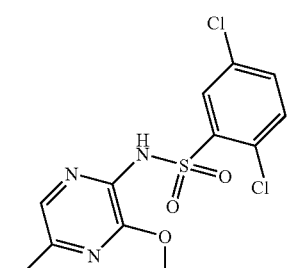

Prepared by the method of Example 1 (reaction performed at room temperature) using 5-bromo-3-methoxy-2-pyrazinamine (0.2 g) and 2,5-dichlorobenzenesulphonyl chloride (0.24 g). Yield 0.14 g.

m/e 410/2/4/6 (M−1$^+$, 100%)

$^1$H NMR (D6-DMSO) δ 8.04 (1H, d), 7.86 (1H, s), 7.73 (1H, dd), 7.66 (1H, dd), 3.91 (3H, s).

EXAMPLE 7

N-(5-Bromo-3-methoxy-2-pyrazinyl)-3,5-dichlorobenzenesulphonamide

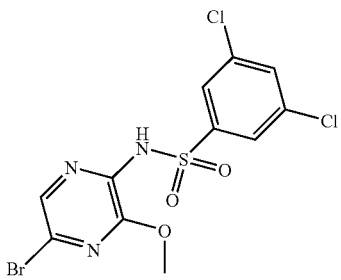

Prepared by the method of Example 1 (reaction performed at room temperature) using 5-bromo-3-methoxy-2-pyrazinamine (0.2 g) and 3,5-dichlorobenzenesulphonyl chloride (0.24 g). Yield 0.012 g.

m/e 410/2/4/6 (M–1$^+$, 100%)

$^1$H NMR (D6-DMSO) δ 7.96-7.91 (4H, m), 3.93 (3H, s).

EXAMPLE 8

N-(5-Bromo-3-methoxy-2-pyrazinyl)-2,3-dichlorobenzenesulphonamide

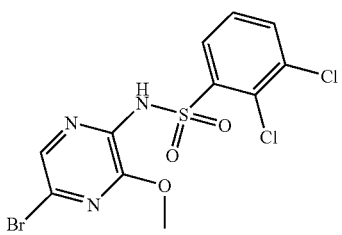

Prepared by the method of Example 1 (reaction performed at room temperature) using 5-bromo-3-methoxy-2-pyrazinamine (0.1 g) and 2,3-dichlorobenzenesulphonyl chloride (0.2 g). Yield 0.045 g., m/e 410/2/4/6 (M–1$^+$, 100%)

$^1$H NMR (D6-DMSO) δ 8.06 (1H, dd), 7.93 (1H, dd), 7.82 (1H, s), 7.57 (1H, t), 3.92 (3H, s).

EXAMPLE 9

N-(5-Bromo-3-methoxy-2-pyrazinyl)-2,4-dichlorobenzenesulphonamide

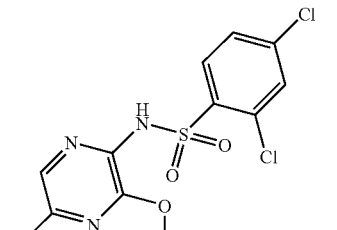

Prepared by the method of Example 1 (reaction performed at room temperature) using 5-bromo-3-methoxy-2-pyrazinamine (0.2 g) and 2,4-dichlorobenzenesulphonyl chloride (0.24 g). Yield 0.059 g.

m/e 410/2/4/6 (M–1$^+$, 100%)

$^1$H NMR (D6-DMSO) δ 8.07 (1H, d), 7.85 (2H, d), 7.64 (1H, dd), 3.92 (3H, s).

EXAMPLE 10

N-(5-Bromo-3-methoxy-2-pyrazinyl)-3,4-dichlorobenzenesulphonamide

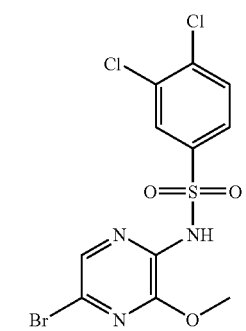

Prepared by the method of Example 1 (reaction performed at room temperature) using 5-bromo-3-methoxy-2-pyrazinamine (0.15 g) and 3,4-dichlorobenzenesulphonyl chloride (0.15 g). Yield 0.09 g.

m/e 410/2/4/6 (M–1$^+$, 100%)

$^1$H NMR (D6-DMSO) δ 8.14 (1H, s), 8.00-7.85 (3H, m), 3.94 (3H, s).

EXAMPLE 11

N-(5-Bromo-3-methoxy-2-pyrazinyl)4-chlorobenzenesulphonamide

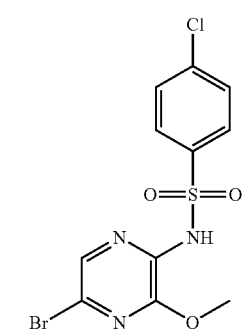

Prepared by the method of Example 1 (reaction performed at room temperature) using 5-bromo-3-methoxy-2-pyrazinamine (0.1 g) and 4-chlorobenzenesulphonyl chloride (0.13 g).

Yield 0.13 g.

m/e 376/8/380 (M–1$^+$, 100%)

$^1$H NMR (D6-DMSO) δ 11.3 (1H, br s), 7.97 (2H, d), 7.91 (1H, s), 7.66 (2H, d), 3.93 (3H, s).

EXAMPLE 12

N-(5-Bromo-3-methoxy-2-pyrazinyl)-3-chlorobenzenesulphonamide

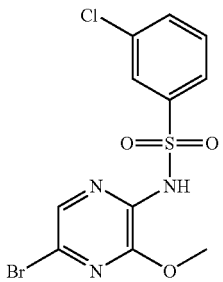

Prepared by the method of Example 1 (reaction performed at room temperature) using 5-bromo-3-methoxy-2-pyrazinamine (0.1 g) and 3-chlorobenzenesulphonyl chloride (0.13 g).
Yield 0.14 g.
m/e 376/8/380 (M−1$^+$, 100%)
$^1$H NMR (D6-DMSO) δ 8.00-7.90 (3H, m), 7.75 (1H, d), 7.64 (1H, t), 3.94 (3H, s).

EXAMPLE 13

N-(3-Methoxy-5-methyl-2-pyrazinyl)-2-fluorobenzenesulphonamide

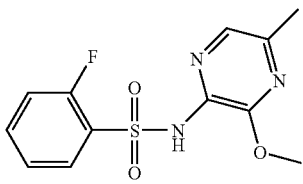

Prepared by the method of Example 1 using 3-methoxy-5-methyl-2-pyrazinamine and 2-fluorobenzenesulphonyl chloride.
m/e 298 (M+1$^+$, 100%)
$^1$H NMR (D6-DMSO) δ 11.05 (1H, br s), 7.85-7.95 (1H, m), 7.65-7.75 (1H, m), 7.50-7.60 (1H, m), 7.35-7.45 (1H, m), 3.90 (3H, s), 2.30 (3H, s).
MP 150-152° C.

EXAMPLE 14

N-(3-Methoxy-5-methyl-2-pyrazinyl)benzenesulphonamide

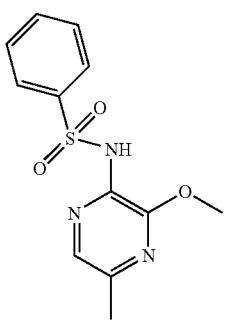

Prepared by the method of Example 1 using 3-methoxy-5-methyl-2-pyrazinamine and benzenesulphonyl chloride
MP 138-139° C.

EXAMPLE 15

N-(3-Methoxy-5-methyl-2-pyrazinyl)-2-iodobenzenesulphonamide

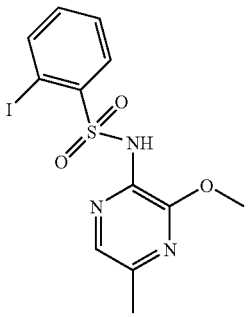

Prepared by the method of Example 1 using 3-methoxy-5-methyl-2-pyrazinamine and 2-iodobenzenesulphonyl chloride.
$^1$H NMR (D6-DMSO) δ 10.75 (1H, br s), 8.05-8.15 (2H, m), 7.65-7.75 (2H, m), 7.30 (1H, dt), 3.90 (3H, s), 2.30 (3H, s).
MP 140-141° C.

EXAMPLE 16

N-(3-Methoxy-5-methyl-2-pyrazinyl)-3-fluorobenzenesulphonamide

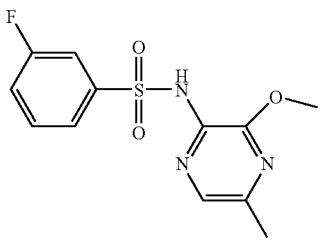

Prepared by the method of Example 1 using 3-methoxy-5-methyl-2-pyrazinamine and 3-fluorobenzenesulphonyl chloride.

EXAMPLE 17

2[[(3-Methoxy-5-methyl-2-pyrazinyl)amino]sulphonyl]benzonitrile

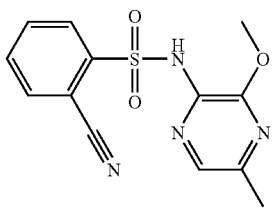

Prepared by method of Example 1 using 3-methoxy-5-methyl-2-pyrazinamine and 2-cyanobenzenesulphonyl chloride.
m/e 305 (M+1$^+$, 100%)

¹H NMR (D6-DMSO) δ 8.15 (1H, dd), 8.05 (1H, dd), 7.85 (1H, dt), 7.80 (1H, dt), 7.60 (1H, s), 3.85 (3H, s), 2.30 (3H, s).

EXAMPLE 18

N-(5-Bromo-3methoxy-2-pyrazinyl)benzenesulphonamide

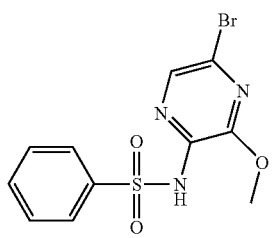

Prepared by method of Example 1 (reaction performed at room temperature) using 5-bromo-3-methoxy-2-pyrazinamine and benzenesulphonyl chloride
m/e 344 (M+1$^+$, 100%)

EXAMPLE 19

N-(5-Bromo-3-methoxy-2-pyrazinyl)2-iodobenzenesulphonamide

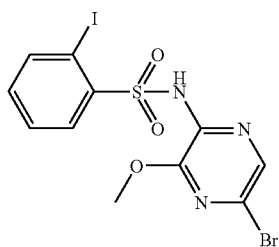

Prepared by the method of Example 1 (reaction performed at room temperature) using 5-bromo-3-methoxy-2-pyrazinamine and 2-iodobenzenesulphonyl chloride.
m/e 470 (M+1$^+$, 100%)
¹H NMR (D6-DMSO) δ 11.30 (1H, br s), 8.0-8.1 (2H, m), 7.80 (1H, s), 7.60 (1H, dt), 7.30 (1H, dt), 3.95 (3H, s).

EXAMPLE 20

2,3-Dichloro-N-[3-(2-furanylmethoxy)-5-methyl-2-pyrazinyl]benzenesulphonamide a) N-(3-Bromo-5-methyl-2-pyrazinyl)-2,3-dichlorobenzenesulphonamide

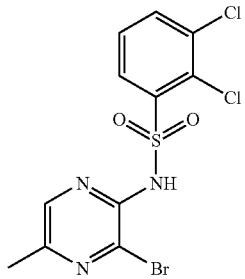

Prepared by the method of Example 1 using 3-bromo-5-methyl-2-pyrazinamine (0.84 g) and 2,3-dichlorobenzenesulphonyl chloride (1.1 g). Yield 0.92 g.

b) 2,3-Dichloro-N-[3-(2-furanylmethoxy)-5-methyl-2-pyrazinyl]benzenesulphonamide

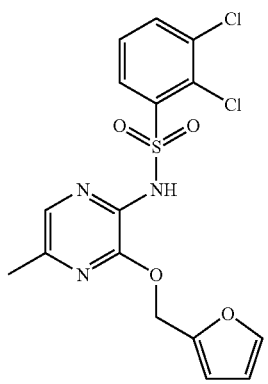

Sodium hydride (0.04 g of a 60% dispersion in oil) was added to fi rylalcohol (0.034 g) in 1,2-dimethoxyethane (1 mL). After 5 minutes N-(3-Bromo-5-methyl-2-pyrazinyl)-2,3-dichlorobenzenesulphonamide (Example 20 part a) (0.1 g) was added and the mixture heated at 40° C. After 16 h, 5% aqueous citric acid (10 mL) was added and the mixture extracted with ethyl acetate (2×50 mL). The combined extracts were washed with brine, dried (MgSO$_4$) and the solvent evaporated. Chromatography on silica gel eluting with dichloromethane gave the title compound as a white solid (0.02 g)
m/e 412 (M−1$^+$, 100%)
¹H NMR (D6-DMSO) δ 11.33 (1H, br s), 8.01 (1H, d), 7.90 (1H, d), 7.70 (1H, s), 7.62 (1H, br s), 7.54 (1H, t), 6.61-6.58 (1H, m), 6.50-6.45 (1H, m), 5.33 (2H, s), 2.32 (3H, s)
MP 127-129° C.

EXAMPLE 21

2,3-Dichloro-N-[5-methyl-3-(5-methyl-3-isoxazolylmethoxy)-2-pyrazinyl]benzenesulphonamide

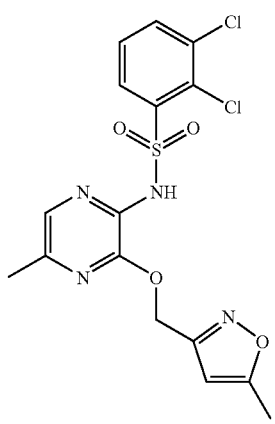

Prepared by the method of Example 20 using (5-methyl-3-isoxazolyl)methanol (0.05 g) and N-(3-bromo-5-methyl-2-pyrazinyl)-2,3-dichlorobenzenesulphonamide (0.1 g). Yield 0.05 g.
m/e 429 (M+1$^+$, 100%)

¹H NMR (D6-DMSO) δ 11.39 (1H, br s), 8.03 (1H, d), 7.91 (1H, d), 7.64 (1H, br s), 7.47 (1H, t), 6.33 (1H, s), 5.37 (2H, s), 2.41 (3H, s), 2.29 (3H, s)

MP 155-156° C.

EXAMPLE 22

2,3-Dichloro-N-[5-methyl-3-(2-pyridinylmethoxy)-2-pyrazinyl]benzenesulphonamide

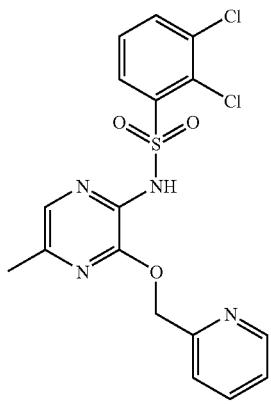

Prepared by the method of Example 20 using pyridine-2-methanol (0.05 g) and N-(3-bromo-5-methyl-2-pyrazinyl)-2,3-dichlorobenzenesulphonamide (0.1 g). Yield 0.07 g.

m/e 425 (M+1⁺, 100%)

¹H NMR (D6-DMSO) δ 8.57-8.54 (1H, m), 8.05 (1H, d), 7.89 (1H, d), 7.83 (1H, dt), 7.65-7.50 (2H, m), 7.56 (1H, t), 7.35-7.30 (1H, m), 5.44 (2H, s), 2.26 (3H, s)

EXAMPLE 23

2,3-Dichloro-N-[5-methyl-3-(6-methyl-2-pyridinyl-methoxy)-2-pyrazinyl]benzenesulphonamide

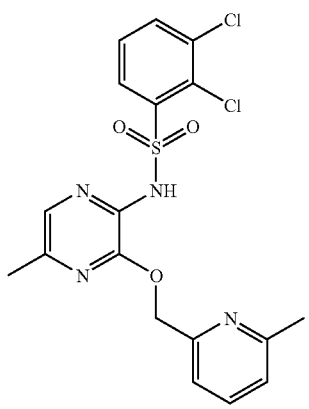

Prepared by the method of Example 20 using 6-methylpyridine-2-methanol (0.05 g) and N-(3-bromo-5-methyl-2-pyrazinyl)-2,3-dichlorobenzenesulphonamide (0.1 g). Yield 0.023 g.

m/e 439 (M+1⁺, 100%)

¹H NMR (D6-DMSO) δ 8.05 (1H, dd), 7.89 (1H, dd), 7.70 (1H, t), 7.59 (1H, br s), 7.54 (1H, t), 7.34 (1H, d), 7.19 (1H, d), 5.39 (2H, s), 2.47 (3H, s), 2.26 (3H, s)

MP 164-165° C.

EXAMPLE 24

2,3-Dichloro-N-[5-methyl-3-(3-pyridinylmethoxy)-2-pyrazinyl]benzenesulphonamide

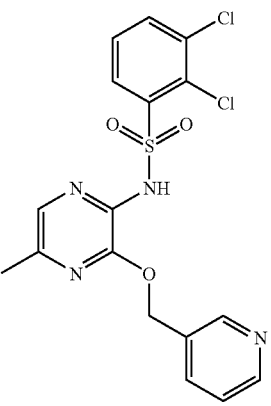

Prepared by the method of Example 20 using pyridine-3-methanol (0.05 g) and N-(3-bromo-5-methyl-2-pyrazinyl)-2,3-dichlorobenzenesulphonamide (0.1 g). Yield 0.023 g.

m/e 425 (M+1⁺, 100%)

¹H NMR (D6-DMSO) δ 8.74 (1H, d), 8.55 (1H, dd), 8.03 (1H, dd), 7.95-7.85 (2H, m), 7.59 (1H, br s), 7.54 (1H, t), 7.42 (1H, dd), 5.41 (2H, s), 2.29 (3H, s)

MP 160-161° C.

EXAMPLE 25

2,3-Dichloro-N-[5-m ethyl-3-(4-pyridinylmethoxy)-2-pyrazinyl]benzenesulphonamide

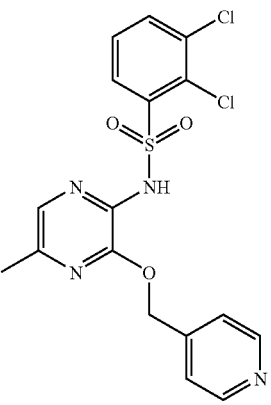

Prepared by the method of Example 20 using pyridine-4-methanol (0.05 g) and N-(3-bromo-5-methyl-2-pyrazinyl)-2,3-dichlorobenzenesulphonamide (0.1 g). Yield 0.009 g.

m/e 425 (M+1⁺, 100%)

¹H NMR (D6-DMSO) δ 8.57 (2H, d), 8.05 (1H, dd), 7.89 (1H, dd), 7.60 (1H, s), 7.55 (1H, t), 7.50 (2H, d), 5.43 (2H, s), 2.26 (3H, s)

MP 183-184° C.

EXAMPLE 26

2,3-Dichloro-N-[5-methyl-3-(3-methyl-2-pyridinyl-methoxy)-2-pyrazinyl]benzenesulphonamide

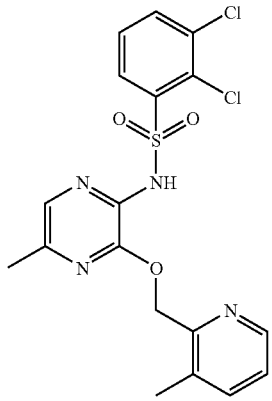

Prepared by the method of Example 20 using 3-methylpyridine-2-methanol (0.05 g) and N-(3-bromo-5-methyl-2-pyrazinyl)-2,3-dichlorobenzenesulphonamide (0.1 g). Yield 0.021 g.

m/e 439 (M+1$^+$, 100%)

$^1$H NMR (D6-DMSO) δ 8.36 (1H, d), 8.05 (1H, dd), 7.83 (1H, dd), 7.64 (1H, d), 7.60 (1H, br s), 7.49 (1H, t), 7.31 (1H, dd), 5.40 (2H, s), 2.33 (3H, s), 2.29 (3H, s)

MP 137-138° C.

EXAMPLE 27

2,3-Dichloro-N-[5-methyl-3-(3-pyridazinyl-methoxy)-2-pyrazinyl]benzenesulphonamide

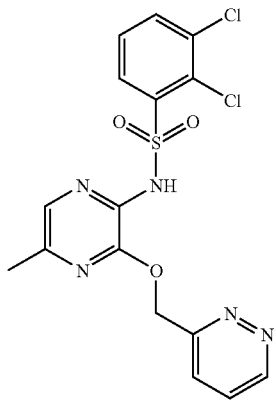

Prepared by the method of Example 20 using pyridazine-3-methanol (0.1 g) and N-(3-bromo-5-methyl-2-pyrazinyl)-2,3-dichlorobenzenesulphonamide (0.15 g). Yield 0.038 g.

m/e 424 (M−1$^+$, 100%)

$^1$H NMR (D6-DMSO) δ 11.47 (1H, br s), 9.21 (1H, dd), 8.05 (1H, dd), 8.00-7.95 (1H, m), 7.88 (1H, d), 7.80-7.75 (1H, m), 7.62 (1H, br s), 7.54 (1H, t), 5.65 (2H, s), 2.27 (3H, s)

MP 119-124° C.

EXAMPLE 28

2,3-Dichloro-N-[3-(2-pyridinylmethoxy)-2-pyrazinyl]benzenesulphonamide a) 2,3-Dichloro-N-(3-chloro-2-pyrazinyl)benzenesulphonamide

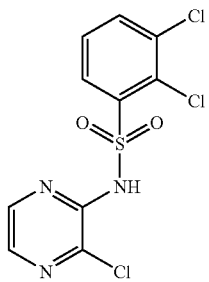

2,3-Dichloropyrazine (2.6 g), 2,3-dichlorobenzenesulphonamide (4.0 g) and potassium is carbonate (10.0 g) in N,N-dimethylformamide (50 mL) was heated at 75° C. After 16 h, 5% aqueous citric acid (30 mL) was added and the mixture extracted with ethyl acetate (2×100 mL). The combined extracts were washed with brine, dried (MgSO$_4$) and the solvent evaporated. Chromatography on silica gel eluting with ethyl acetate/isohexane mixtures gave the title compound (1.5 g).

b) 2,3-Dichloro-N-[3-(2-pyridinylmethoxy)-2-pyrazinyl]benzenesulphonamide

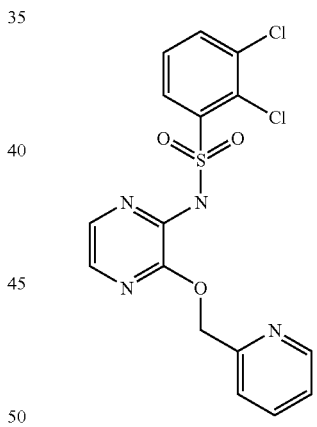

Sodium hydride (0.05 g of a 60% dispersion in oil) was added to pyridine-2-methanol (0.088 g) in 1,2-dimethoxyethane (3.0 mL). After 5 minutes, 2,3-dichloro-N-(3-chloro-2-pyrazinyl)benzenesulphonamide (0.1 g) was added and the mixture heated at 70° C. After 4 h, 5% aqueous citric acid (10 mL) was added and the mixture extracted with ethyl acetate (2×50 mL). The combined extracts were washed with brine, dried (MgSO$_4$) and the solvent evaporated. Chromatography on silica gel eluting with ethyl acetate/isohexane mixtures gave the title compound as a white solid (0.06 g).

m/e 411 (M+1$^+$, 100%)

$^1$H NMR (D6-DMSO) δ 8.57 (1H, d), 8.13 (1H, d), 7.93 (1H, d), 7.90-7.75 (2H, m), 7.75-7.65 (1H, m), 7.65-7.55 (2H, m), 7.40-7.30 (1H, m), 5.49 (2H, s)

MP 167-168° C.

EXAMPLE 29

2,3-Dichloro-N-[3-(3-pyridinylmethoxy)-2-pyrazinyl]benzenesulphonamide

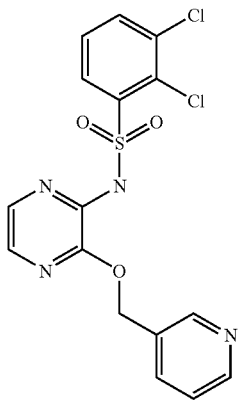

Prepared by the method of Example 28 using pyridine-3-methanol (0.09 g) and 2,3-dichloro-N-(3-chloro-2-pyrazinyl)benzenesulphonamide (0.1 g). Yield 0.042 g.

m/e 409 (M−1$^+$, 100%)

$^1$H NMR (CDCl$_3$) δ 8.70 (1H, s), 8.65 (1H, d), 8.28 (1H, dd), 7.79 (1H, d), 7.70-7.67 (2H, m), 7.61 (1H, d), 7.40-7.35 (2H, m), 5.45 (2H, s)

MP 138-139° C.

EXAMPLE 30

2,3-Dichloro-N-(3-methoxy-2-pyrazinyl)benzenesulphonamide

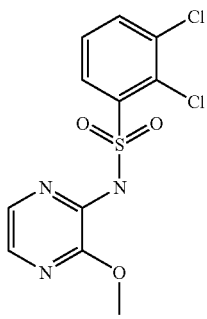

2,3-Dichloro-N-(3-chloro-2-pyrazinyl)benzenesulphonamide (Example 28 part a) (0.2 g) in 10% sodium methoxide in methanol (10 mL) was heated at 85° C. After 4 h, 5% aqueous citric acid (50 mL) was added and the mixture extracted with ethyl acetate (2×150 mL). The combined extracts were washed with brine, dried (MgSO$_4$) and the solvent evaporated. Chromatography on silica gel eluting with ethyl acetate/isohexane mixtures gave the title compound as a white solid (0.12 g)

m/e 334 (M+1$^+$, 100%)

$^1$H NMR (D6-DMSO) δ 11.54 (1H, br s), 8.10 (1H, d), 7.94 (1H, d), 7.85-7.75 (1H, m), 7.70-7.55 (1H, m), 7.59 (1H, t), 3.90 (3H, s)

MP 183-184° C.

EXAMPLE 31

N-[5-Bromo-3-(2-pyrazinylmethoxy)-2-pyrazinyl]-2,3-dichlorobenzenesulphonamide a) 2,3-Dichloro-N-(3,5-dibromo-2-pyrazinyl)benzenesulphonamide

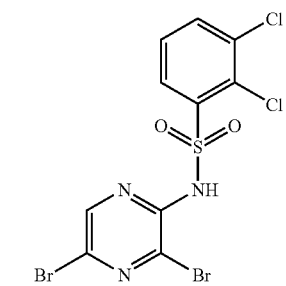

Prepared by the method of Example 1 (reaction performed at room temperature) using 3,5-dibromo-2-pyrazinamine (2.9 g) and 2,3-dichloro benzenesulphonyl chloride (2.8 g). Yield 4.4 g.

b) N-[5-Bromo-3-(2-pyrazinylmethoxy)-2-pyrazinyl]-2,3-dichlorobenzenesulphonamide Sodium hydride (0.05 g of a 60% dispersion in oil) was added to pyrazine-2-methanol (0.04 g) in 1,2-dimethoxyethane (3 ml). After 5 minutes, 2,3-Dichloro-N-(3,5-dibromo-2-pyrazinyl)benzenesulphonamide (0.12 g) was added. After 0.5 h, 5% aqueous citric acid (10 mL) was added and the mixture extracted with ethyl acetate (2×30 mL). The combined extracts were washed with brine, dried (MgSO$_4$) and the solvent evaporated. Chromatography on silica gel eluting with ethyl acetate/isohexane mixtures gave the title compound as a white solid (0.06 g).

m/e 489 (M−1$^+$, 100%)

$^1$H NMR (D6-DMSO) δ 9.00 (1H, s), 8.66 (2H, s), 8.08 (1H, dd), 7.92 (1H, dd), 7.91 (1H, s), 7.56 (1H, t), 5.53 (2H, s)

MP 207-209° C.

EXAMPLE 32

N-[5-Bromo-3-(1-methyl-6-oxo-1,6-dihydro-3-pyridinylmethoxy)-2-pyrazinyl]-2,3-dichlorobenzenesulphonamide

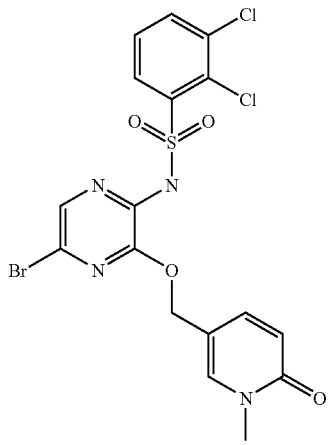

Prepared by the method of Example 31 using 5-hydroxymethyl-1-methyl-1H-pyridin-2-one (0.1 g) and 2,3-dichloro-N-(3,5-dibromo-2-pyrazinyl)benzenesulphonamide (0.16 g). Yield 0.035 g.

m/e 521 (M+1$^+$, 100%)

$^1$H NMR (D6-DMSO) δ 8.04 (1H, dd), 7.91 (1H, dd), 7.90-7.87 (2H, m), 7.60-7.50 (2H, m), 6.42 (1H, d), 5.10 (2H, s), 3.41 (3H, s)

MP 169-170° C.

EXAMPLE 33

N-[5-Bromo-3-(3-pyridazinyl]methoxy)-2-pyrazinyl]-2,3-dichlorobenzenesulphonamide

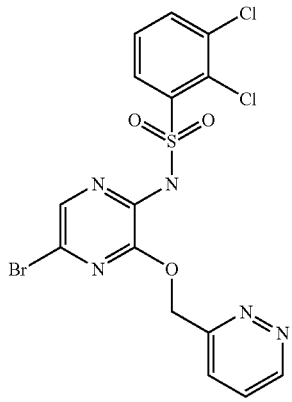

Is Prepared by the method of Example 31 using pyridazine-3-methanol (0.07 g) and 2,3-dichloro-N-(3,5-dibromo-2-pyrazinyl)benzenesulphonamide (0.15 g). Yield 0.06 g.

m/e 489 (M−1$^+$, 100%)

$^1$H NMR (D6-DMSO) δ 9.23 (1H, d), 8.08 (1H, dd), 7.99 (1H, dd), 7.92 (1H, dd), 7.91 (1H, s), 7.80 (1H, dd), 7.56 (1H, t), 5.67 (2H, s)

MP 115-120° C.

EXAMPLE 34

N-[5-Bromo-3-(3-pyridinylmethoxy)-2-pyrazinyl]-2,3-dichlorobenzenesulphonamide

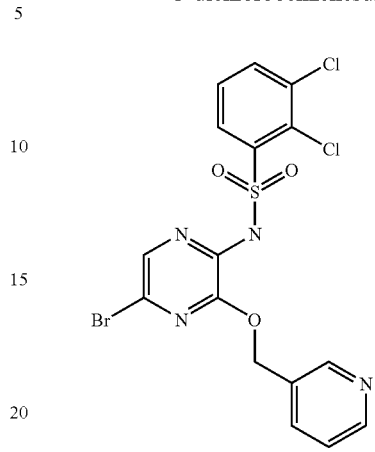

Prepared by the method of Example 31 using pyridine-3-methanol (0.44 g) and 2,3-dichloro-N-(3,5-dibromo-2-pyrazinyl)benzenesulphonamide (1.0 g). Yield 0.6 g.

m/e 491 (M+1$^+$, 100%)

$^1$H NMR (D6-DMSO) δ 8.78 (1H, d), 8.58 (1H, dd), 8.06 (1H, d), 7.99 (1H, dt), 7.91 (1H, d), 7.88 (1H, s), 7.55 (1H, t), 7.55-7.50 (1H, m), 5.44 (2H, s)

MP 204-206° C.

EXAMPLE 35

N-[5-Bromo-3-(5-pyrimidinylmethoxy)-2-pyrazinyl]-2,3-dichlorobenzenesulphonamide

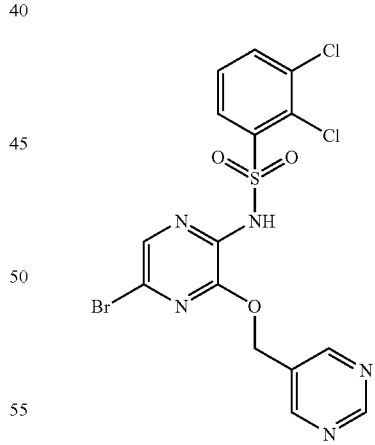

Prepared by the method of Example 31 using pyrimidine-5-methanol (0.035 g) and 2,3-dichloro-N-(3,5-dibromo-2-pyrazinyl)benzenesulphonamide (0.16 g). Yield 0.028 g.

m/e 490 (M−1$^+$, 100%)

$^1$H NMR (D6-DMSO) δ 9.21 (1H, s), 9.02 (2H, s), 8.07 (1H, dd), 7.92 (1H, dd), 7.91 (1H, s), 7.56 (1H, t), 5.45 (2H, s)

MP 208-209° C.

EXAMPLE 36

N-[5-Chloro-3-(3-pyridinylmethoxy)-2-pyrazinyl]-2,3-dichlorobenzenesulphonamide

Prepared by the method of Example 31 using pyridine-3-methanol (0.13 g) and 2,3-dichloro-N-(3,5-dichloro-2-pyrazinyl)benzenesulphonamide (Example 74) (0.3 g). Yield 0.19 g.

m/e 447 (M+1$^+$, 100%)

$^1$H NMR (D6-DMSO) δ 8.78 (1H, s), 8.59 (1H, dd), 8.06 (1H, dd), 7.96 (1H, dt), 7.91 (1H, dd), 7.83 (1H, s), 7.55 (1H, t), 7.47 (1H, dd), 5.44 (2H, s)

MP 200-204° C.

EXAMPLE 37

N-[5-Chloro-3-(5-pyrimidinylmethoxy)-2-pyrazinyl]-2,3-dichlorobenzenesulphonamide Prepared by the method of Example 31 using pyrimidine-5-methanol (0.035 g) and 2,3-dichloro-N-(3,5-dichloro-2-pyrazinyl)benzenesulphonamide (Example 74) (0.07 g). Yield 0.015 g.

m/e 448 (M+1$^+$, 100%)

$^1$H NMR (D6-DMSO) δ 9.21 (1H, s), 9.02 (2H, s), 8.08 (1H, dd), 7.92 (1H, dd), 7.86 (1H, s), 7.56 (1H, t), 5.46 (2H, s)

MP 205-206° C.

EXAMPLE 38

2-Chloro-N-(6-chloro-3-methoxy-2-pyrazinyl)benzenesulphonamide

Prepared by the method of Example 1 (reaction performed at room temperature) using 6-chloro-3-methoxy-2-pyrazinamine (0.1 g) and 2-chlorobenzenesulphonyl chloride (0.13 g).

Yield 0.11 g.

m/e 332 (M−1$^+$, 100%)

$^1$H NMR (D6-DMSO) δ 8.15 (1H, d), 7.86 (1H, s), 7.70-7.50 (3H, m), 3.91 (3H, s)

MP 172-173° C.

EXAMPLE 39

3-Chloro-N-(6-chloro-3-methoxy-2-pyrazinyl)benzenesulphonamide

Prepared by the method of Example 1 (reaction performed at room temperature) using 6-chloro-3-methoxy-2-pyrazinamine (0.1 g) and 3-chlorobenzenesulphonyl chloride (0.13 g).

Yield 0.14 g.

m/e 332 (M−1$^+$, 100%)

$^1$H NMR (D6-DMSO) δ 8.05 (1H, d), 7.93 (1H, dd), 7.90 (1H, s), 7.76 (1H, dd), 7.65 (1H, t) 3.92 (3H, s)

MP 126-127° C.

EXAMPLE 40

4-Chloro-N-(6-chloro-3-methoxy-2-pyrazinyl)benezenesulphonamide

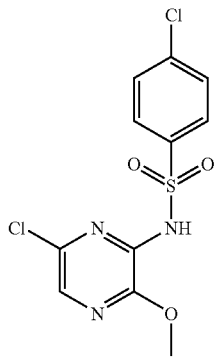

Prepared by the method of Example 1 (reaction performed at room temperature) using 6-chloro-3-methoxy-2-pyrazinamine (0.1 g) and 4-chlorobenzenesulphonyl chloride (0.13 g).

Yield 0.13 g.

m/e 332 (M−1$^+$, 100%)

$^1$H NMR (D6-DMSO) δ 7.99 (2H, dt), 7.89 (1H, s), 7.70 (2H, dt), 3.92 (3H, s)

MP 174-175° C.

EXAMPLE 41

N-(6-Chloro-3-methoxy-2-pyrazinyl)-2,4-dichlorobenezenesulphonamide

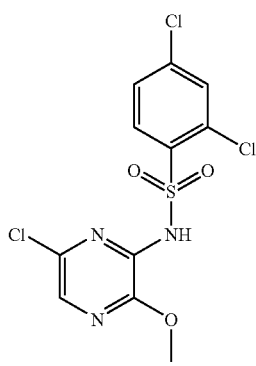

Prepared by the method of Example 1 (reaction performed at room temperature) using 6-chloro-3-methoxy-2-pyrazinamine (0.05 g) and 2,4-dichlorobenzenesulphonyl chloride (0.1 g). Yield 0.07 g.

m/e 368 (M−1$^+$, 100%)

$^1$H NMR (D6-DMSO) δ 8.13 (1H, d), 7.86 (1H, s), 7.85 (1H, d), 7.70 (1H, dd), 3.91 (3H, s)

MP 189-190° C.

EXAMPLE 42

N-(6-Chloro-3-methoxy-2-pyrazinyl)-3,4-dichlorobenezenesulphonamide

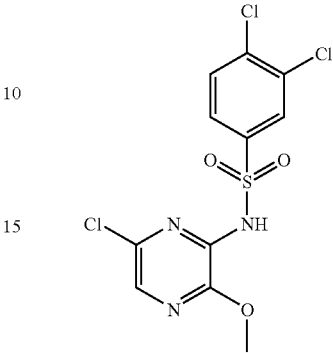

Prepared by the method of Example 1 (reaction performed at room temperature) using 6-chloro-3-methoxy-2-pyrazinamine (0.05 g) and 3,4-dichlorobenzenesulphonyl chloride (0.09 g). Yield 0.08 g.

m/e 368 (M−1$^+$, 100%)

$^1$H NMR (D6-DMSO) δ 8.21 (1H, s), 7.93-7.90 (3H, m), 3.92 (3H, s)

MP 176-177° C.

EXAMPLE 43

3-Chloro-N-(3-methoxy-5-methyl-2-pyrazinyl)-2-methylbenezenesulphonamide

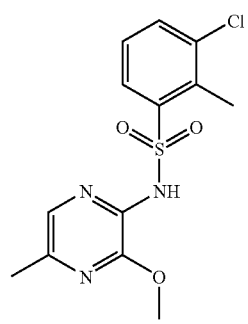

Prepared by the method of Example 1 using 3-methoxy-5-methyl-2-pyrazinamine (0.1 g) and 3-chloro-2-methylbenzenesulphonyl chloride (0.19 g). Yield 0.08 g.

m/e 328 (M+1$^+$, 100%)

$^1$H NMR (D6-DMSO) δ 11.09 (1H, br s), 7.95 (1H, d), 7.72 (1H, d), 7.54 (1H, br s), 7.41 (1H, t), 3.88 (3H, s), 2.64 (3H, s), 2.27 (3H, s)

MP 133-135° C.

EXAMPLE 44

2-Chloro-N-(3-methoxy-5-methyl-2-pyrazinyl)benezenesulphonamide

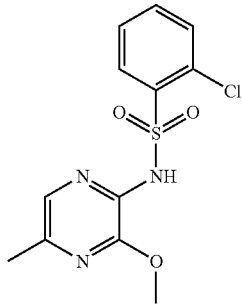

Prepared by the method of Example 1 using 3-methoxy-5-methyl-2-pyrazinamine (0.1 g) and 2-chlorobenzenesulphonyl chloride (0.15 g). Yield 0.06 g.

m/e 314 (M+1$^+$, 100%)

$^1$H NMR (D6-DMSO) δ 11.07 (1H, br s), 8.06 (1H, d), 7.69-7.46 (4H, m), 3.90 (3H, s), 2.24 (3H, s)

EXAMPLE 45

3-Chloro-N-(3-methoxy-5-methyl-2-pyrazinyl)benezenesulphonamide

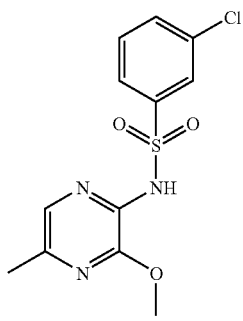

Prepared by the method of Example 1 using 3-methoxy-5-methyl-2-pyrazinamine (0.1 g) and 3-chlorobenzenesulphonyl chloride (0.18 g). Yield 0.042 g.

m/e 314 (M+1$^+$, 100%)

$^1$H NMR (D6-DMSO) δ 10.89 (1H, br s), 7.97 (1H, d), 7.92 (1H, d), 7.73 (1H, d), 7.65-7.58 (2H, m), 3.90 (3H, s), 2.29 (3H, s)

MP 123-125° C.

EXAMPLE 46

4-Chloro-N-(3-methoxy-5-methyl-2-pyrazinyl)benezenesulphonamide

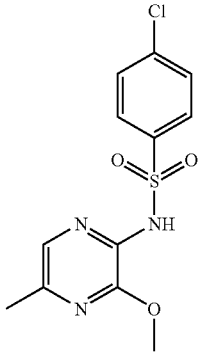

Prepared by the method of Example 1 using 3-methoxy-5-methyl-2-pyrazinamine (0.1 g) and 4-chlorobenzenesulphonyl chloride (0.18 g). Yield 0.06 g.

m/e 314 (M+1$^+$, 100%)

$^1$H NMR (D6-DMSO) δ 10.83 (1H, br s), 7.96 (2H, d), 7.65 (2H, d), 7.60 (1H, s), 3.88 (3H, s), 2.28 (3H, s)

MP 155-156° C.

EXAMPLE 47

2,4-Dichloro-N-(3-methoxy-5-methyl-2-pyrazinyl)benezenesulphonamide

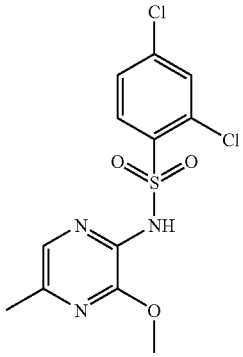

Prepared by the method of Example 1 using 3-methoxy-5-methyl-2 -pyrazinamine (0.1 g) and 2,4-dichlorobenzenesulphonyl chloride (0.21 g). Yield 0.041 g.

m/e 348 (M+1$^+$, 100%)

$^1$H NMR (D6-DMSO) δ 8.05 (1H, d), 7.83 (1H, d), 7.64 (1H, dd), 7.54 (1H, br s), 3.87 (3H, s), 2.27 (3H, s)

MP 135-136° C.

EXAMPLE 48

3,4-Dichloro-N-(3-methoxy-5-methyl-2-pyrazinyl)benezenesulphonamide

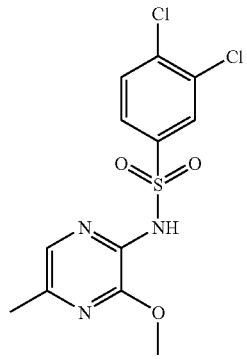

Prepared by the method of Example 1 using 3-methoxy-5-methyl-2-pyrazinamine (0.1 g) and 3,4-dichlorobenzenesulphonyl chloride (0.21 g). Yield 0.046 g.

m/e 348 (M+1$^+$, 100%)

$^1$H NMR (D6-DMSO) δ 10.97 (1H, s), 8.14 (1H, d), 7.91 (1H, dd), 7.88 (1H, d), 7.63 (1H, s), 3.89 (3H, s), 2.27 (3H, s)
MP 148-149° C.

EXAMPLE 49

N-(5-Bromo-3-methoxy-2-pyrazinyl)-2-trifluoromethoxybenezenesulphonamide

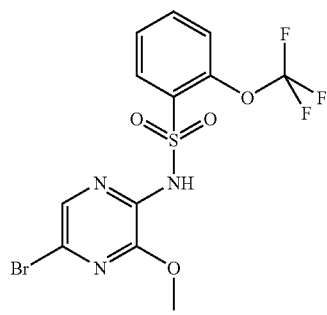

Prepared by the method of Example 1 (reaction performed at room temperature) using 5-bromo-3-methoxy-2-pyrazinamine (0.1 g) and 2-trifluoromethoxybenzenesulphonyl chloride (0.13 g). Yield 0.097 g m/e 428 (M−1$^+$, 100%)

$^1$H NMR (D6-DMSO) δ 8.03 (1H, dd), 7.87 (1H, s), 7.82-7.74 (1H, m), 7.60-7.52 (2H, m), 3.92 (3H, s)
MP 156-157° C.

EXAMPLE 50

3-Chloro-N-(5-chloro-3-methoxy-2-pyrazinyl)-2-methylbenzenesulphonamide

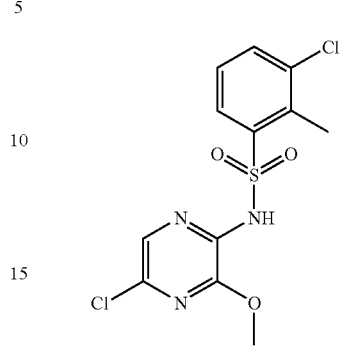

Prepared by the method of Example 1 (reaction performed at room temperature) using 5-chloro-3-methoxy-2-pyrazinamine (0.1 g) and 3-chloro-2-methylbenzenesulphonyl chloride (0.15 g). Yield 0.085 g.

m/e 346 (M−1$^+$, 100%)

$^1$H NMR (CDCl$_3$) δ 8.17 (1H, d), 7.69 (1H, br s), 7.64 (1H, s), 7.61 (2H, d), 7.30 (1H, t), 4.04 (3H, s), 2.73 (3H, s)
MP 150-152° C.

EXAMPLE 51

2-Chloro-N-(5-chloro-3-methoxy-2-pyrazinyl)benzenesulphonamide

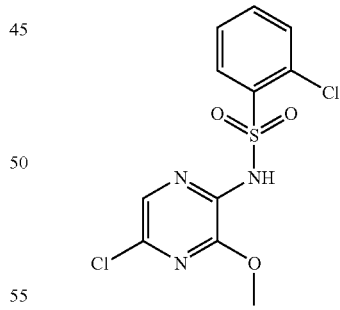

Prepared by the method of Example 1 (reaction performed at room temperature) using 5-chloro-3-methoxy-2-pyrazinamine (0.1 g) and 2-chlorobenzenesulphonyl chloride (0.13 g).

Yield 0.082 g.

m/e 332 (M+1$^+$, 100%)

$^1$H NMR (CDCl$_3$) δ 8.33 (1H, d), 7.82 (1H, s), 7.64-7.62 (1H, m), 7.61 (1H, s), 7.50-7.42 (2H, m), 4.04 (3H, s)
MP 190-192° C.

EXAMPLE 52

3-Chloro-N-(5-chloro-3-methoxy-2-pyrazinyl)benzenesulphonamide

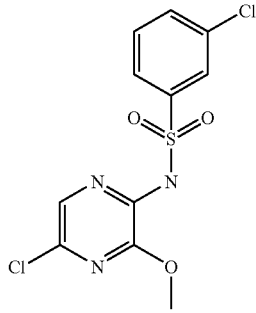

Prepared by the method of Example 1 (reaction performed at room temperature) using 5-chloro-3-methoxy-2-pyrazinamine (0.1 g) and 3-chlorobenzenesulphonyl chloride (0.13 g).

Yield 0.095 g.

m/e 332 (M+1$^+$, 100%)

$^1$H NMR (CDCl$_3$) δ 8.14 (1H, s), 8.03 (1H, d), 7.76 (1H, s), 7.68-7.53 (2H, m), 7.46 (1H, t), 4.02 (3H, s)

MP 129-130° C.

EXAMPLE 53

4-Chloro-N-(5-chloro-3-methoxy-2-pyrazinyl)benzenesulphonamide

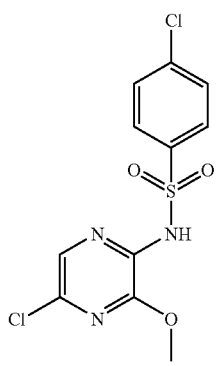

Prepared by the method of Example 1 (reaction performed at room temperature) using 5-chloro-3-methoxy-2-pyrazinamine (0.1 g) and 4-chlorobenzenesulphonyl chloride (0.13 g).

Yield 0.05 g.

m/e 332 (M+1$^+$, 100%)

$^1$H NMR (CDCl$_3$) δ 8.07 (2H, d), 7.75 (1H, s), 7.56 (1H, s), 7.49 (2H, d), 4.02 (3H, s)

MP 179-180° C.

EXAMPLE 54

N-(5-Chloro-3-methoxy-2-pyrazinyl)-2,4-dichlorobenzenesulphonamide

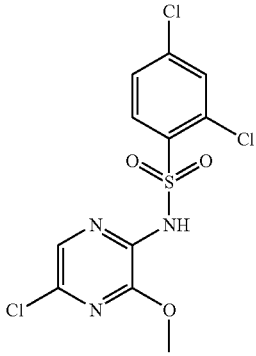

Prepared by the method of Example 1 (reaction performed at room temperature) using 5-chloro-3-methoxy-2-pyrazinamine (0.1 g) and 2,4-dichlorobenzenesulphonyl chloride (0.13 g). Yield 0.045 g.

m/e 368 (M−1$^+$, 100%)

$^1$H NMR (CDCl$_3$) δ 8.27 (1H, d), 7.78 (1H, s), 7.63 (1H, s), 7.48 (1H, s), 7.43 (1H, d), 4.05 (3H, s)

MP 170-171° C.

EXAMPLE 55

2,3-Dichloro-N-[3-methoxy-5-(4-morpholinyl)-2-pyrazinyl]benzenesulphonamide a) N-(5-Bromo-3-methoxy-2-pyrazinyl)-2,3-dichloro-N-{[2-(trimethylsilanyl)ethoxy]methyl}benzenesulphonamide

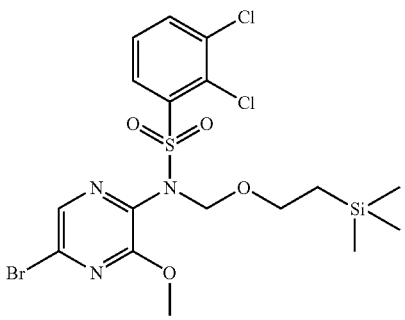

A mixture of N-(5-Bromo-3-methoxy-2-pyrazinyl)-2,3-dichlorobenzenesulphonamide (Example 8) (0.40 g), diisopropylethylamine (0.26 g) and [2-(chloromethoxy)ethyl]trimethylsilane (0.25 g) in dichloromethane (50 mL) was stirred at room temperature. After 2 h, the solution was washed with water, dried (MgSO$_4$) and evaporated. Chromatography on silica gel eluting with ethyl acetate/isohexane mixtures gave the title compound as a white solid (0.40 g).

$^1$H NMR (CDCl$_3$) δ 8.09 (1H, s), 7.96 (1H, dd), 7.68 (1H, dd), 7.29 (1H, t), 5.24 (2H, s), 3.92 (3H, s), 3.77-3.73 (2H, m), 0.86-0.82 (2H, m), 0.00 (9H, s)

b) 2,3-Dichloro-N-[3-methoxy-5-(4-morpholinyl)-2-pyrazinyl]benzenesulphonamide

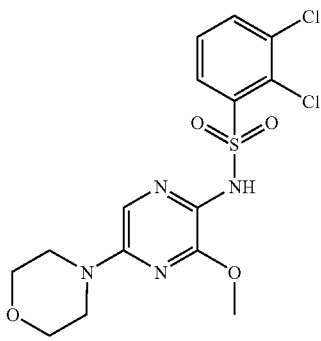

N-(5-Bromo-3-methoxy-2-pyrazinyl)-2,3-dichloro-N-[{12-(trimethylsilanyl)ethoxy}methyl]benzenesulphonamide (0.30 g) and morpholine (0.45 g) in acetonitrile (10 mL) was heated at 50° C. After 16 h, the solution was evaporated. Chromatography on silica gel eluting with ethyl acetate/isohexane mixtures gave the title compound with SEM group attached, as a white solid. The solid was dissolved in trifluoroacetic acid (5.0 mL) and dichloromethane (5.0 mL). After 2 h, the solution was evaporated. Chromatography on silica gel eluting with ethyl acetate/isohexane mixtures gave the title compound as a white solid (0.06 g).

m/e 417 (M−1$^+$, 100%)

$^1$H NMR (CDCl$_3$) δ 8.17 (1H, d), 7.65 (1H, d), 7.41 (1H, s), 7.34 (1H, t), 7.16 (1H, s), 3.89 (3H, s), 3.80-3.75 (4H, m), 3.40-3.35 (4H, m)

MP 167-168° C.

EXAMPLE 56

2,3-Dichloro-N-[3,5-dimethoxy-2-pyrazinyl]benzenesulphonamide

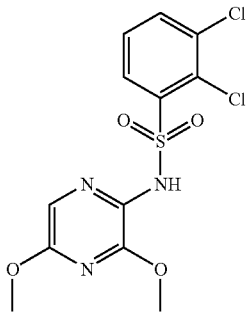

N-(5-Bromo-3-methoxy-2-pyrazinyl)-2,3-dichloro-N-[{2-(trimethylsilanyl)ethoxy}methyl]benzenesulphonamide (0.30 g) in methanolic sodium methoxide (10 mL of 0.5 molar solution) was stirred at room temperature. After 16 h, the solution was evaporated to dryness and dichloromethane (10 mL) and trifluoroacetic acid (10 mL) added. After 2 h, the mixture was evaporated to dryness, dichloromethane added and the inorganic salts removed by filtration. Chromatography on silica gel eluting with ethyl acetate/isohexane mixtures gave the title compound as a white solid (0.1 g).

m/e 364 (M+1$^+$, 100%)

$^1$H NMR (CDCl$_3$) δ 8.21 (1H, d), 7.67 (1H, d), 7.50 (1H, s), 7.37 (1H, t), 7.26 (1H, s), 3.98 (3H, s), 3.87 (3H, s)

MP 138-139° C.

EXAMPLE 57

2,3-Dichloro-N-[3-methoxy-5-(1-pyrrolinyl)-2-pyrazinyl]benzenesulphonamide

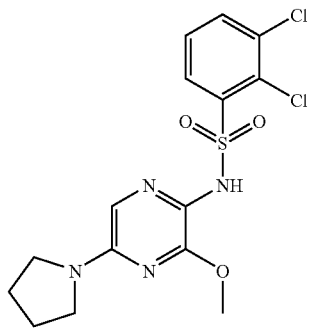

Prepared by the method of Example 55 using pyrrolidine (0.4 g) and N-(5-bromo-3-methoxy-2-pyrazinyl)-2,3-dichloro-N-[{2-(trimethylsilanyl)ethoxy}methyl]benzenesulphonamide (0.3 g). Yield 0.045 g.

m/e 403 (M+1$^+$, 100%)

$^1$H NMR (CDCl$_3$) δ 8.08 (1H, d), 7.64 (1H, d), 7.30 (1H, t), 7.21 (1H, s), 6.99 (1H, s), 3.81 (3H, s), 3.40-3.35 (4H, m), 2.00-1.95 (4H, m)

MP 179-180° C.

EXAMPLE 58

3-Chloro-N-(5,6-dichloro-3-methoxy-2-pyrazinyl)-2-methylbenzenesulphonamide

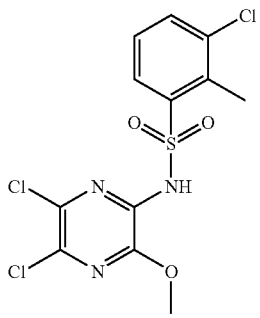

Prepared by the method of Example 1 (reaction performed at room temperature) using 5,6-dichloro-3-methoxy-2-pyrazinamine (0.1 g) and 3-chloro-2-methylbenzenesulphonyl chloride (0.14 g). Yield 0.13 g.

m/e 381 (M−1$^+$, 100%)

$^1$H NMR (CDCl$_3$) δ 8.25 (1H, d), 7.65 (1H, br s), 7.62 (1H, d), 7.35 (1H, t), 4.04 (3H, s), 2.73 (3H, s)

MP 177-178° C.

EXAMPLE 59

2,3-Dichloro-N-(5,6-dichloro-3-methoxy-2-pyrazinyl)benzenesulphonamide

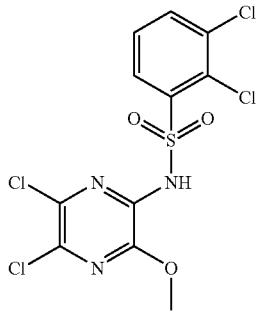

Prepared by the method of Example 1 (reaction performed at room temperature) using 5,6-dichloro-3-methoxy-2-pyrazinamine (0.1 g) and 2,3-dichlorobenzenesulphonyl chloride (0.15 g). Yield 0.12 g.

m/e 402 (M–1$^+$, 100%)

$^1$H NMR (CDCl$_3$) δ 8.31 (1H, d), 7.81 (1H, br s), 7.72 (1H, d), 7.45 (1H, t), 4.05 (3H, s)

MP 172-173° C.

EXAMPLE 60

2-Chloro-N-(5,6-dichloro-3-methoxy-2-pyrazinyl)benzenesulphonamide

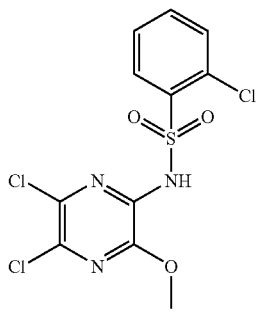

Prepared by the method of Example 1 (reaction performed at room temperature) using 5,6-dichloro-3-methoxy-2-pyrazinamine (0.1 g0 and 2-chlorobenzenesulphonyl chloride (0.13 g). Yield 0.096 g.

m/e 367 (M–1$^+$, 100%)

$^1$H NMR (CDCl$_3$) δ 8.39 (1H, 4), 7.79 (1H, br s), 7.58-7.45 (3H, m), 4.04 (3H, s)

MP 217-218° C.

EXAMPLE 61

3-Chloro-N-(5,6-dichloro-3-methoxy-2-pyrazinyl)benzenesulphonamide

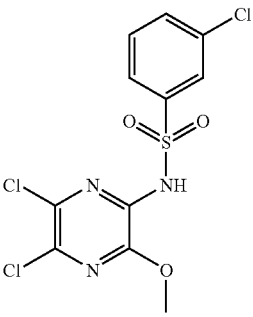

Prepared by the method of Example 1 (reaction performed at room temperature) using 5,6-dichloro-3-methoxy-2-pyrazinamine (0.1 g) and 3-chlorobenzenesulphonyl chloride (0.13 g). Yield 0.047 g.

m/e 367 (M–1$^+$, 100%)

$^1$H NMR (CDCl$_3$) δ 8.19 (1H, s), 8.07 (1H, d), 7.61 (1H, d), 7.59 (1H, br s), 7.50 (1H, t), 4.02 (3H, s)

MP 171-172° C.

EXAMPLE 62

4-Chloro-N-(5,6-dichloro-3-methoxy-2-pyrazinyl)benzenesulphonamide

Prepared by the method of Example 1 (reaction performed at room temperature) using 5,6-dichloro-3-methoxy-2-pyrazinamine (0.1 g) and 4-chlorobenzenesulphonyl chloride (0.13 g). Yield 0.09 g.

m/e 367 (M–1$^+$, 100%)

$^1$H NMR (CDCl$_3$) δ 8.11 (2H, d), 7.57 (1H, br s), 7.50 (2H, d), 4.02 (3H, s)

MP 186-187° C.

EXAMPLE 63

2,4-Dichloro-N-(5,6-dichloro-3-methoxy-2-pyrazinyl)benzenesulphonamide

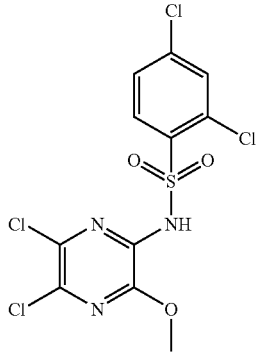

Prepared by the method of Example 1 (reaction performed at room temperature) using 5,6-dichloro-3-methoxy-2-pyrazinamine (0.1 g) and 2,4-dichlorobenzenesulphonyl chloride (0.15 g). Yield 0.076 g.

m/e 402 (M−1+, 100%)

$^1$H NMR (CDCl$_3$) δ 8.30 (1H, d), 7.76 (1H, br s), 7.50 (1H, s), 7.48 (1H, d), 4.05 (3H, s)

MP 171-172° C.

EXAMPLE 64

3,4-Dichloro-N-(5,6-dichloro-3-methoxy-2-pyrazinyl)benzenesulphonamide

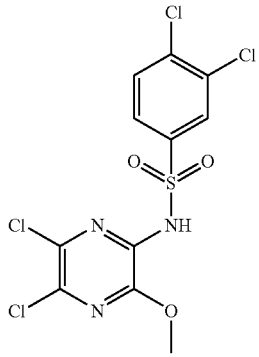

Prepared by the method of Example 1 (reaction performed at room temperature) using 5,6-dichloro-3-methoxy-2-pyrazinamine (0.1 g) and 3,4-dichlorobenzenesulphonyl chloride (0.15 g). Yield 0.11 g.

m/e 402 (M−1+, 100%)

$^1$H NMR (CDCl$_3$) δ 8.30 (1H, s), 8.01 (1H, d), 7.63 (1H, d), 7.58 (1H, br s), 4.03 (3H, s)

MP 189-191° C.

EXAMPLE 65

2,3-Dichloro-N-(3-methoxy-5,6-dimethyl-2-pyrazinyl)benzenesulphonamide

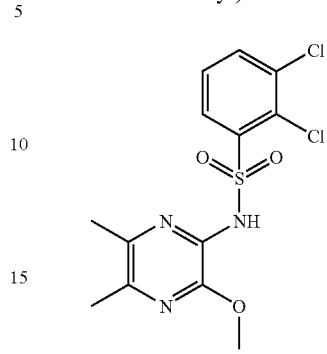

Prepared by the method of Example 1 using 3-methoxy-5,6-dimethyl-2-pyrazinamine (0.07 g) and 2,3-dichlorobenzenesulphonyl chloride (0.12 g). Yield 0.04 g.

m/e 360 (M−1+, 100%)

$^1$H NMR (CDCl$_3$) δ 8.32 (1H, d), 7.67 (1H, s), 7.65 (1H, d), 7.39 (1H, t), 3.95 (3H, s), 2.28 (3H, s), 2.14 (3H, s)

MP 165-166° C.

EXAMPLE 66

2,3-Dichloro-N-(6-chloro-3,5-dimethoxy-2-pyrazinyl)benzenesulphonamide a) 2,3-Dichloro-N-(5,6-dichloro-3-methoxy-2-pyrazinyl)-N-{[2-(trimethylsilyl)ethoxy]methyl}benzenesulphonamide

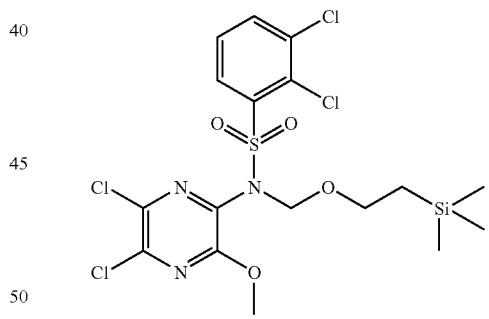

To a stirred solution of 2,3-Dichloro-N-(5,6-dichloro-3-methoxy-2-pyrazinyl)benzenesulphonamide (0.68 g) in dichloromethane (20 mL) was added triethylamine (0.49 mL) followed by 2-(trimethylsilyl)ethoxymethyl chloride (0.328 g) and the resulting mixture was stirred at room temperature for 1 h. The reaction mixture was poured into water (50 mL) and extracted into ethyl acetate (3×20 mL). The combined extracts were dried (MgSO$_4$), filtered and concentrated. Chromatography on silica gel eluting with ethyl acetate/isohexane mixtures gave the sub-title compound as a white solid (0.74 g).

$^1$H NMR (CDCl$_3$) δ 8.02 (1H, dd), 7.70 (1H, dd), 7.34 (1H, t), 5.22 (2H, s), 3.96 (3H, s), 3.73 (2H, dd), 0.91-0.79 (2H, m), −0.03 (9H, s)

b) 2,3-Dichloro-N-(6-chloro-3,5-dimethoxy-2-pyrazinyl)benzenesulphonamide

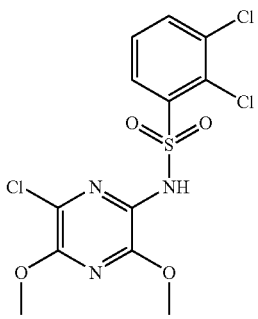

2,3-Dichloro-N-(5,6-dichloro-3-methoxy-2-pyrazinyl)-N-{[2-(trimethylsilyl)ethoxy]methyl}benzenesulfonamide (0.10 g) was dissolved in methanol (1.0 mL) and a solution of sodium methoxide in methanol (0.1 mL of a 25% solution in methanol) was added. The reaction was stirred at room temperature for 30 min and was concentrated. The residue was dissolved in trifluoroacetic acid (2.0 mL) and was stirred at room temperature for 30 min. The reaction mixture was concentrated and chromatography on silica gel eluting with ethyl acetate/isohexane mixtures gave the title compound as a white solid (0.028 g).

m/e 397 (M–1+, 100%)

$^1$H NMR (CDCl$_3$) δ 8.26 (1H, d), 7.69 (1H, d), 7.41 (1H, t), 7.41 (1H, br s), 4.02 (3H, s), 3.91 (3H, s)

MP 163-165° C.

EXAMPLE 67

2,3-Dichloro-N-[6-chloro-3-methoxy-5-(4-morpholinyl)-2-pyrazinyl]benzenesulphonamide

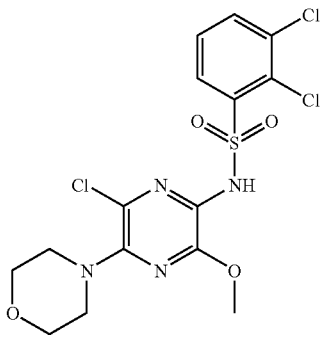

2,3-Dichloro-N-(5,6-dichloro-3-methoxy-2-pyrazinyl)-N-{[2-(trimethylsilyl)ethoxy]methyl}benzenesulphonamide (Example 66 part a) (0.10 g) was dissolved in THF (1.0 mL) and a solution of morpholine (0.05 g) in THF (0.1 mL) was added. The reaction was stirred at room temperature for 30 min and was concentrated.

The residue was dissolved in trifluoroacetic acid (2.0 mL) and dichloromethane (2.0 mL) and was stirred at room temperature for 30 min. The reaction mixture was concentrated and chromatography on silica gel eluting with ethyl acetate/isohexane mixtures gave the title compound as a white solid (0.042 g).

m/e 452 (M–1+, 100%)

$^1$H NMR (CDCl$_3$) δ 8.28 (1H, dd), 7.69 (1H, dd), 7.49 (1H, br s), 7.43 (1H, t), 3.96 (3H, s), 3.79 (4H, dd), 3.28 (4H, dd)

MP 150-151° C.

EXAMPLE 68

2,3-Dichloro-N-[6-chloro-5-(2-hydroxyethylamino)-3-methoxy-2-pyrazinyl]benzenesulphonamide

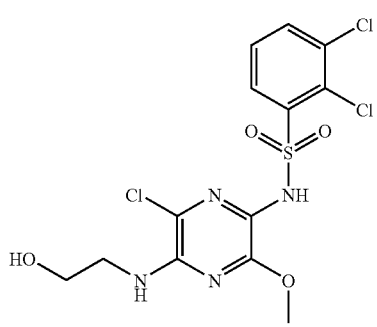

Prepared by the method of Example 67 using 2-aminoethanol (0.05 g) and 2,3-dichloro-N-(5,6-dichloro-3-methoxy-2-pyrazinyl)-N-{[2-(trimethylsilyl)ethoxy]methyl}benzenesulfonamide (0.1 g). Yield 0.015 g.

m/e 426 (M-100%)

$^1$H NMR (D6-DMSO) δ 10.31 (1H, s), 7.91 (2H, dd), 7.52 (1H, t), 6.89 (1H, br s), 4.71 (1H, t), 3.63 (3H, s), 3.53 (2H, dd), 3.40 (2H, dd)

EXAMPLE 69

2,3-Dichloro-N-[6-chloro-5-dimethylamino-3-methoxy-2-pyrazinyl]benzenesulphonamide

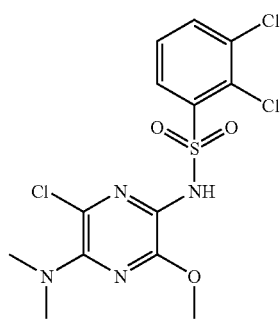

Prepared by the method of Example 67 using dimethylamine (5 mL of a 2M solution in tetrahydrofuran) and 2,3-dichloro-N-(5,6-dichloro-3-methoxy-2-pyrazinyl)-N-{[2-(trimethylsilyl)ethoxy]methyl}benzenesulfonamide (0.1 g). Yield 0.015g.

m/e 410 (M–1+, 100%)

$^1$H NMR (D6-DMSO) δ 7.99-7.93 (2H, m), 7.56 (1H, t), 3.74 (3H, s), 2.99 (6H, s)

MP 145-146° C.

EXAMPLE 70

2,3-Dichloro-N-[6-chloro-3-methoxy-5-(2-methoxyethoxy)-2-pyrazinyl]benzenesulphonamide

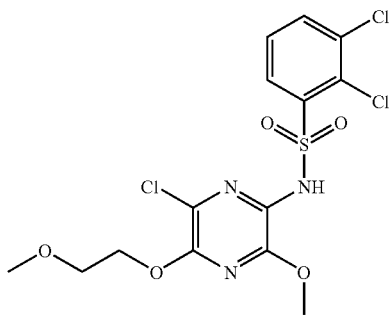

Sodium hydride (0.019g of 60% dispersion in oil) was added to a solution of 2,3-dichloro-N-(5,6-dichloro-3-methoxy-2-pyrazinyl)-N-{[2-(trimethylsilyl)ethoxy]methyl}benzenesulfonamide (0.25g) in 2-methoxyethanol (3.0 mL) at room temperature. After 16 h, the solvent was evaporated and trifluoroacetic acid (2.0 mL) added. After 1 h, the reaction mixture was concentrated and chromatography on silica gel eluting with ethyl acetate/isohexane mixtures gave the title compound as a white solid (0.08 g).

m/e 442 (M+1$^+$, 100%)

$^1$H NMR (CDCl$_3$) δ 8.24 (1H, dd), 7.70 (1H, dd), 7.41 (1H, t), 4.50-4.40 (2H, m), 3.96 (3H, s), 3.80-3.70 (2H, m), 3.42 (3H, s)

MP 193-194° C.

EXAMPLE 71

2,3-Dichloro-N-[6-chloro-5-hydroxy-3-methoxy-2-pyrazinyl]benzenesulphonamide

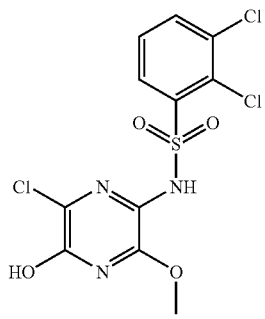

tetrabutylammonium hydroxide (0.28 g of 40% aqueous solution) was added to a solution of 2,3-dichloro-N-(5,6-dichloro-3-methoxy-2-pyrazinyl)-N-{[2-(trimethylsilyl)ethoxy]methyl}benzenesulfonamide (0.25 g) in 1,2-dimethoxyethane (3.0 mL) at room temperature. After 16 h, the solution was diluted with ethyl acetate (20 mL). The organic solution was washed with aqueous citric acid (10 mL) and brine, dried (MgSO$_4$) and evaporated. Chromatography on silica gel eluting with ethyl acetate/isohexane mixtures gave the title compound containing the SEM group, as a white solid (0.08 g). The solid was dissolved in trifluoroacetic acid (2.0 mL) and dichloromethane (2.0 mL) and stirred at room temperature for 1 h. The reaction mixture was concentrated and chromatography on silica gel eluting with ethyl acetate/isohexane mixtures gave the title compound as a white solid (0.027 g).

m/e 384 (M+1$^+$, 100%)

$^1$H NMR (CDCl$_3$) δ 12.56 (1H, s), 10.87 (1H, s), 7.96 (2H, t), 7.56(1H, t), 3.74 (3H, s)

EXAMPLE 72

2,3-Dichloro-N-[6-methoxy-5-([2,2']bipyrazinylyl)]benzenesulphonamide

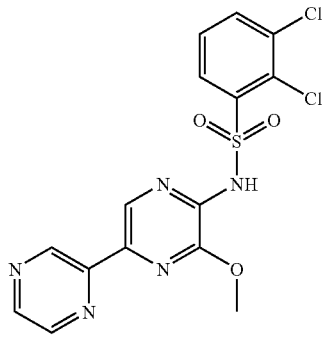

N-(5-Bromo-3-methoxy-2-pyrazinyl)-2,3-dichloro-N-[{2-(trimethylsilanyl)ethoxy}methyl]benzenesulphonamide (Example 55 part a) (0.70 g), tetrakis(triphenylphosphine)palladium(0) (0.1 g) and 2-(tributylstannanyl)pyrazine (0.50 g) in toluene (20 mL) was heated under nitrogen at 100° C. After 16 h, chromatography on silica gel eluting with ethyl acetate/isohexane mixtures gave the title compound protected with the SEM group as a white solid. The solid was dissolved in trifluoroacetic acid (2.0 mL) and dichloromethane (2.0 mL) and stirred at room temperature for 1 h. The reaction mixture was concentrated, toluene added and evaporated. The title compound crystallised from acetonitrile to give a white solid (0.38 g).

m/e 410 (M−1$^+$, 100%)

$^1$H NMR (D6 DMSO) δ 9.35 (1H, s), 8.69 (1H, d), 8.67 (1H, d), 8.40 (1H, br s), 8.14 (1H, d), 7.96 (1H, d), 7.61 (1H, t), 4.07 (3H, s)

MP 199-200° C.

EXAMPLE 73

4-[5-(2,3-Dichlorobenzenesulphonylamino)-6-methoxy-2-pyrazinyloxy]benzoic acid

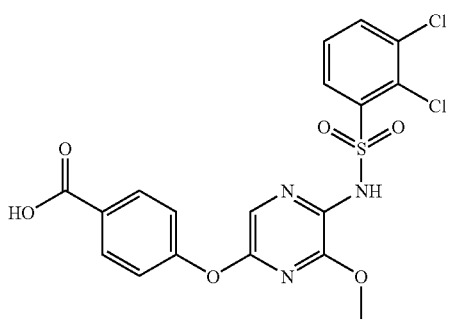

4-Hydroxybenzoic acid tert butyl ester (0.13 g), N-(5-bromo-3-methoxy-2-pyrazinyl)-2,3-dichloro-N-[{2-(trimethylsilanyl)ethoxy}methyl]benzenesulphonamide (Example 55 part a) (0.35 g) and caesium carbonate (0.42 g) in acetonitrile (10 mL) was heated at 50° C. After 12 h, the mixture was diluted with ethyl acetate, washed with water, dried (MgSO₄) and evaporated. Chromatography on silica gel eluting with ethyl acetate/isohexane mixtures gave the title compound protected with the SEM group and tert butyl group as an oil. The oil was dissolved in trifluoroacetic acid (2.0 mL) and stirred at room temperature for 3 h.

The reaction mixture was concentrated, toluene added and evaporated to give the title compound as a white solid (0.19 g).

m/e 468 (M−1⁺, 100%)

¹H NMR (CDCl₃) δ 8.28 (1H, d), 8.11 (2H, d), 7.80 (1H, br s), 7.71 (1H, d), 7.45 (2H, m), 7.12 (2H, d), 3.89 (3H, s)

MP 186-187° C.

EXAMPLE 74

2,3-Dichloro-N-(3,5-dichloro-2-pyrazinyl)benzene-sulphonamide

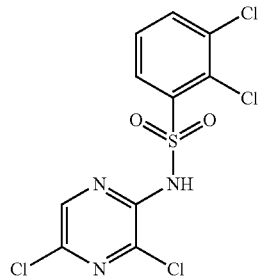

Prepared by the method of Example 1 (reaction performed at room temperature) using 3,5-dichloro-2-pyrazinamine (2.0 g) and 2,3-dichloro benzenesulphonyl chloride (2.94 g). Yield 3.0 g.

m/e 372 (M−1⁺, 100%)

¹H NMR (D6 DMSO) δ 8.29 (1H, s), 8.06 (1H, dd), 7.94 (1H, dd), 7.57 (1H, t)

MP 181-182° C.

EXAMPLE 75

2,3-Dichloro-N-{6-chloro-3-methoxy-5-([2-methoxyethyl)amino]-2-pyrazinyl}benzenesulphonamide

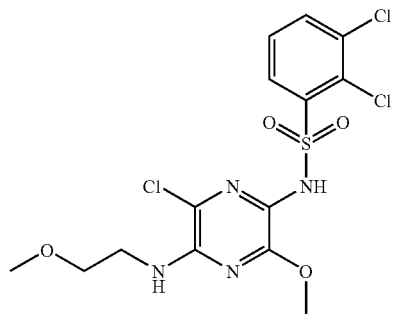

Prepared by the method of Example 67 using 2-methoxyethylamine (3 mL) and 2,3-dichloro-N-(5,6-dichloro-3-methoxy-2-pyrazinyl)-N-{[2-(trimethylsilyl)ethoxy]methyl}benzenesulphonamide (0.24 g). Yield 0.08 g.

m/e 439 (M+1⁺, 100%)

¹H NMR (D6-DMSO) δ 10.33 (1H, s), 7.92 (2H, dd), 7.52 (1H, t), 7.00 (1H, s), 3.64 (3H, s), 3.47 (4H, s), 3.24 (2H, dd)

MP 177-178° C.

EXAMPLE 76

N-{2-[3-Chloro-5-(2,3-dichlorobenzenesulphonylamino)-6-methoxy-2-pyrazinylamino]ethyl}acetamide

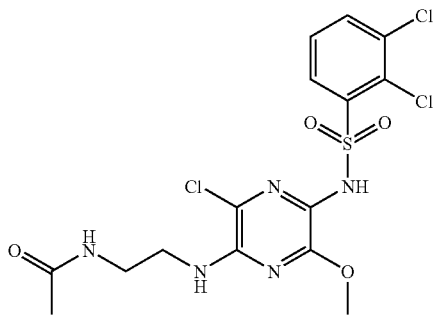

2,3-Dichloro-N-(5,6-dichloro-3-methoxy-2-pyrazinyl)-N-{[2-(trimethylsilyl)ethoxy]methyl}benzenesulphonamide (Example 66 part a) (0.26 g) was dissolved in acetonitrile (1.0 mL) and N-acetylethylenediamine (0.055 mL) and triethylamine (0.19 mL) added. After 48 h, the reaction mixture was concentrated and chromatography on silica gel eluting with ethyl acetate gave the title compound protected with the SEM group, as an oil (0.13 g). The oil was dissolved in dichloromethane (2.0 mL) and boron trifluoride etherate (0.14ml) added. After 2 h, ethyl acetate (20 mL) was added and the mixture washed with 5% aqueous citric acid (5 mL), dried (MgSO₄) and evaporated. Chromatography on silica gel eluting with ethyl acetate gave the title compound as a solid (0.031 g).

m/e 470 (M+1⁺, 100%)

¹H NMR (D6-DMSO) δ 10.32 (1H, s), 7.93-7.88 (2H, m), 7.52 (1H, t), 7.10 (1H, s), 3.65 (3H, s), 3.40-3.10 (4H, m), 1.75 (3H, s)

MP 150-152° C.

EXAMPLE 77

2,3-Dichloro-N-[5-(4-hydroxymethyl-1-piperidinyl)-3-methoxy-2-pyrazinyl]benzenesulphonamide

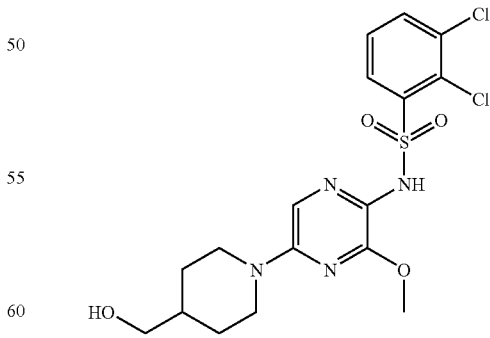

Prepared by the method of Example 55 using 4-(hydroxymethyl)piperidine (0.4 g) and N-(5-bromo-3-methoxy-2-pyrazinyl)-2,3-dichloro-N-[{2-(trimethylsilanyl)ethoxy}methyl]benzenesulphonamide (0.3 g). Yield 0.012 g.

m/e 447 (M+1⁺, 100%)

$^1$H NMR (CDCl$_3$) δ 8.14 (1H, dd), 7.65 (1H, dd), 7.33 (1H, t), 7.20 (1H, s), 4.20-4.10 (2H, m), 3.86 (3H, s), 3.60-3.50 (2H, m), 2.90-2.70 (2H, m), 1.90-1.70 (3H, m), 1.40-1.20 (3H, m)

EXAMPLE 78

2,3-Dichloro-N-[5-cyano-3-(3-pyridinylmethoxy)-2-pyrazinyl]benzenesulphonamide

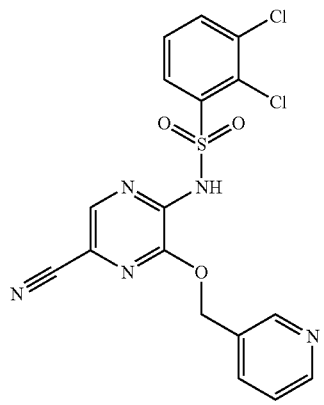

N-[5-Bromo-3-(3-pyridinylmethoxy)-2-pyrazinyl]-2,3-dichlorobenzenesulphonamide (Example 34) (0.15 g), tetrakis(triphenylphosphine)palladium(0) (0.04 g) and zinc cyanide (0.03 g) in N,N-dimethylformamide (5.0 mL) was heated at 70° C. After 5 h, the mixture was diluted with ethyl acetate (30 mL) and washed with 5% aqueous citric acid (5 mL), dried (MgSO$_4$) and evaporated. Chromatography on silica gel eluting with ethyl acetate/isohexane mixtures containing 1% acetic acid gave the title compound as a white solid (0.058 g).

m/e 436 (M+1$^+$, 100%)

$^1$H NMR (D6 DMSO) δ 8.70-7.65 (2H, m), 8.29 (1H, dd), 7.99 (1H, s), 7.78 (1H, d), 7.73 (1H, dd), 7.46 (1H, t), 7.40-7.35 (1H, m), 5.45 (2H, s)

MP 222-224° C.

EXAMPLE 79

2,3-Dichloro-N-(6-chloro-3-methoxy-5-methylamino-2-pyrazinyl)benzenesulphonamide

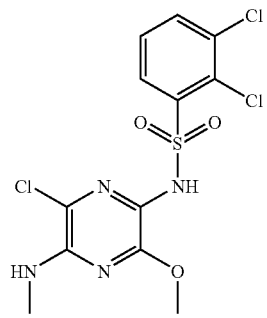

3-Dichloro-N-(5,6-dichloro-3-methoxy-2-pyrazinyl)-N-{[2-(trimethylsilyl)ethoxy]methyl}benzenesulphonamide (Example 66 part a) (0.25 g) was dissolved in methanol (1.0 mL) and methylamine (2.0 mL of 40% aqueous solution) was added. After 16 h, the solution was partitioned between water and ethyl acetate. The organic layer was dried (MgSO$_4$) and evaporated. The residue was dissolved in dichloromethane (2.0 mL) and boron trifluoride etherate (0.25 mL) added. After 1 h, ethyl acetate (20 mL) was added and the solution washed with 5% aqueous citric acid (5 mL), dried (MgSO$_4$) and evaporated. Chromatography on silica gel eluting with ethyl acetate/isohexane mixtures gave the title compound as a white solid (0.05 g).

m/e 395 (M+1$^+$, 100%)

$^1$H NMR (D6-DMSO) δ 10.27 (1H, s), 7.95-7.87 (2H, m), 7.51 (1H, dd), 7.10-7.00 (1H, m), 3.64 (3H, s), 2.84 (3H, s)

MP 185-186° C.

EXAMPLE 80

2,3-Dichloro-N-(3-methoxy-5-methylsulphanyl-2-pyrazinyl)benzenesulphonamide

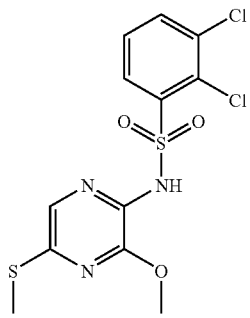

N-(5-Bromo-3-methoxy-2-pyrazinyl)-2,3-dichloro-N-{[2-(trimethylsilanyl)ethoxy]methyl}benzenesulphonamide (0.30 g) and sodium thiomethoxide (0.05 g) in acetonitrile (10 mL) was stirred at room temperature. After 2 h, the solution was evaporated. Chromatography on silica gel eluting with ethyl acetate/isohexane mixtures gave the title compound with SEM group attached. The compound was dissolved in trifluoroacetic acid (5 mL). After 2 h, toluene (20 mL) was added and the solution evaporated. Chromatography on silica gel eluting with ethyl acetate/isohexane mixtures gave the title compound as a white solid (0.16 g).

m/e 380 (M+1$^+$, 100%)

$^1$H NMR (CDCl$_3$) δ 8.25 (1H, d), 7.70 (1H, s), 7.68 (1H, d), 7.52 (1H, s), 7.39 (1H, t), 4.03 (3H, s), 2.48 (3H, s)

MP 141-142° C.

EXAMPLE 81

2,3-Dichloro-N-[5-(2,4-difluorophenyl)-3-methoxy-2-pyrazinyl]benzenesulphonamide a) 5-(2,4-difluorophenyl)-3-methoxy-2-pyrazinamine

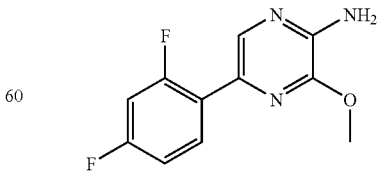

5-Bromo-3-methoxy-2-pyrazinamine (0.3 g), cesium fluoride (0.8 g), 2,4-difluorobenezeneboronic acid (0.4 g) and [1,1'-bis(diphenylphosphino)ferrocene]palladium (II) chloride (0.04 g) in methanol (20 mL) was heated at 70° C. After 6 h, the solvent was evaporated and the residue purified by chromatography on silica eluting with ethyl acetate/isohexane mixtures to give the sub-title compound (0.2 g).

b) 2,3-Dichloro-N-[5-(2,4-difluorophenyl)-3-methoxy-2-pyrazinyl]benzenesulphonamide

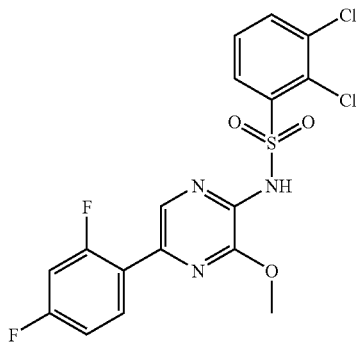

Prepared by the method of Example 1 using 5-(2,4-difluorophenyl)-3-methoxy-2-pyrazinamine (0.2 g) and 2,3-dichlorobenzenesulphonyl chloride (0.2 g). Yield 0.06 g.

m/e 444 (M−1+, 100%)

$^1$H NMR (D6-DMSO) δ 8.15 (1H, d), 8.05-7.95 (2H, m), 7.93 (1H, d), 7.60 (1H, t), 7.45-7.35 (1H, m), 7.30-7.20 (1H, m), 4.03 (3H, s)

MP 169-170° C.

EXAMPLE 82

[5-(2,3-Dichlorobenzenesulphonylamino)-6-methoxy-2-pyrazinylsulphanyl]acetic acid

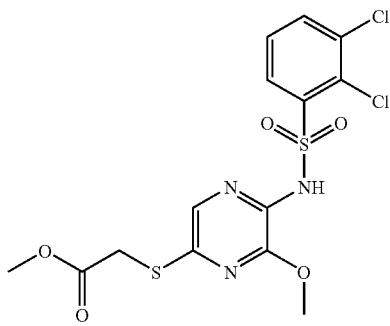

N-(5-Bromo-3-methoxy-2-pyrazinyl)-2,3-dichloro-N-[{2-(trimethylsilanyl)ethoxy}methyl]benzenesulphonamide (0.40 g), mercaptoacetic acid methyl ester (0.1 g) and caesium carbonate (0.6 g) in acetonitril (10 mL) was stirred at room temperature. After 16 h, the solution was diluted with dichloromethane, filtered and evaporated. Chromatography on silica gel eluting with ethyl acetate/isohexane mixtures gave the title compound with SEM group attached. The compound was dissolved in trifluoroacetic acid (5mL). After 2 h, toluene (20 mL) was added and the solution evaporated. Chromatography on silica gel eluting with ethyl acetate/isohexane mixtures gave the title compound as a white solid (0.15 g).

m/e 438 (M+1+, 100%)

$^1$H NMR (CDCl$_3$) δ 8.26 (1H, dd), 7.73 (1H, s), 7.68 (1H, dd), 7.59 (1H, s), 7.41 (1H, t), 3.99 (3H, s), 3.80 (2H, s), 3.71 (3H, s)

MP 152-153° C.

EXAMPLE 83

[5-(2,3-Dichlorobenzenesulphonylamino)-6-methoxy-2-pyrazinylsulphanyl]acetic acid

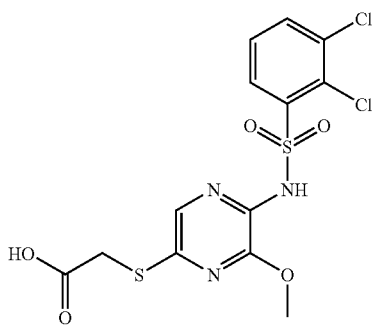

[5-(2,3-Dichlorobenzenesulphonylamino)-6-methoxy-2-pyrazinylsulphanyl]acetic acid methyl ester (Example 82) (0.1 g) and lithium hydroxide (0.04 g) in methanol (5 mL) and water (1 mL) was stirred at room temperature. After 2 h, the mixture was evaporated and saturated aqueous citric acid (5 mL) added. The white solid was collected, washed with water and dried. Yield 0.07 g.

m/e 424 (M+1+, 100%)

$^1$H NMR (CDCl$_3$) δ 8.27 (1H, dd), 7.90 (1H, br s), 7.70 (1H, dd), 7.61 (1H, s), 7.40 (1H, t), 3.98 (3H, s), 3.80 (2H, s)

MP 138-140° C.

EXAMPLE 84

2,3-Dichloro-N-[5-(2-chlorobenzylsulphanyl)-3-methoxy-2-pyrazinyl]benzenesulphonamide

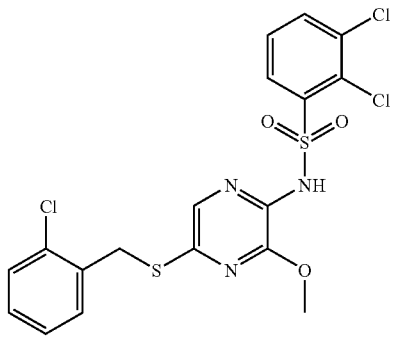

Prepared by the method of Example 82 using 2-chlorobenzylmercaptan (0.15 g) and N-(5-bromo-3-methoxy-2-pyrazinyl)-2,3-dichloro-N-[{2-(trimethylsilanyl)ethoxy}methyl]benzenesulphonamide (0.4 g). Yield 0.18 g.

m/e 492 (M+1+, 100%)

$^1$H NMR (CDCl$_3$) δ 8.26 (1H, dd), 7.73 (1H, s), 7.69 (1H, dd), 7.53 (1H, s), 7.40-7.30 (3H, m), 7.20-7.10 (2H, m), 4.39 (2H, s), 4.02 (3H, s)

MP 119-120° C.

EXAMPLE 85

2,3-Dichloro-N-[6-chloro-5-(3-hydroxy-1-azetidinyl)-3-methoxy-2-pyrazinyl]benzenesulphonamide

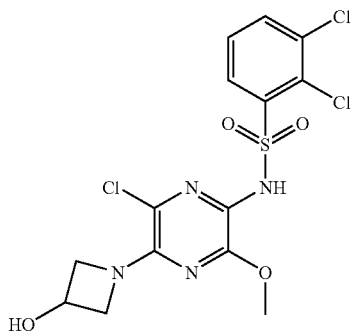

2,3-Dichloro-N-(5,6-dichloro-3-methoxy-2-pyrazinyl)-N-{[2-(trimethylsilyl)ethoxy]methyl}benzenesulphonamide (Example 66 part a) (0.20 g), azetidin-3-ol hydrochloride (0.082 g) and triethylamine (0.25 mL) in acetonitrile (3 mL) and water (0.5 mL) was stirred at room temperature. After 2 h, the mixture was evaporated and triturated with diethyl ether. The ethereal solution was evaporated and the residue dissolved in a 1 molar solution of tetrabutylammonium fluoride in THF (6 mL). After 16 h, the reaction mixture was concentrated and chromatography on silica gel eluting with ethyl acetate/isohexane mixtures gave the title compound as a white solid (0.024 g).

m/e 442 (M+1$^+$, 100%)

$^1$H NMR (D6-DMSO) δ 10.58 (1H, s), 7.92 (2H, d), 7.54 (1H, t), 5.66 (1H, s), 4.49 (1H, s), 4.36 (2H, t), 3.88 (2H, m), 3.67 (3H, s)

MP 93-95° C.

EXAMPLE 86

2,3-Dichloro-N-[5-methyl-3-(1-oxy-3-pyrazinyl-methoxy)-2-pyrazinyl]benzenesulphonamide

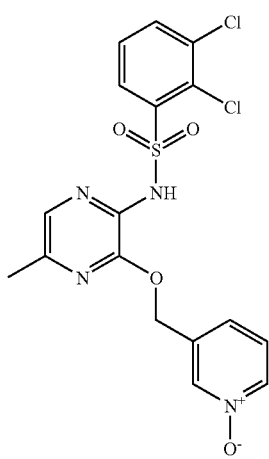

2,3-Dichloro-N-[5-methyl-3-(3-pyridinylmethoxy)-2-pyrazinyl)benzenesulphonamide (Example 24) (0.2 g) and 3-chloroperbenzoic acid (0.35 g) in dichloromethane (4 mL) was is stirred at room temperature. After 0.5 h, chromatography on silica gel eluting with 5% methanol in ethyl acetate containing 1% acetic acid gave the title compound as a white solid (0.16 g).

m/e 441 (M+1$^+$, 100%)

$^1$H NMR (D6-DMSO) δ 11.56 (1H, br s), 8.60 (1H, br s), 8.18 (1H, dt), 8.06 (1H, dd), 7.90 (1H, dd), 7.61 (1H, br s), 7.56 (1H, t), 7.50-7.40 (2H, m), 5.36 (2H, s), 2.28 (3H, s)

MP 223-228° C.

EXAMPLE 87

2,3-Dichloro-N-[5-chloro-3-(4-pyridinylmethoxy)-2-pyrazinyl]benzenesulphonamide

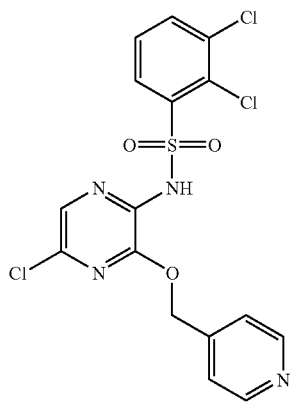

Prepared by the method of Example 31b using pyridine-4-methanol (0.4 g) and 2,3-dichloro-N-(3,5-dichloro-2-pyrazinyl)benzenesulphonamide (Example 74) (0.4 g). Yield 0.47 g.

m/e 445 (M+1$^+$, 100%)

$^1$H NMR (D6-DMSO) δ 8.63 (2H, d), 8.08 (1H, dd), 7.91 (1H, dd), 7.83 (1H, s), 7.60 (2H, d), 7.55 (1H, t), 5.47 (2H, s)

MP 226-229° C. decomposes

EXAMPLE 88

2,3-Dichloro-N-[5-chloro-3-(1-oxy4-pyridinyl-methoxy)-2-pyrazinyl]benzenesulphonamide

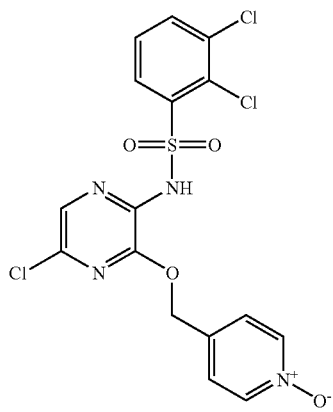

Prepared by the method of Example 86 using 2,3-dichloro-N-[5-chloro-3-(4-pyridinylmethoxy)-2-pyrazinyl]benzene-sulphonamide (Example 87) (0.1 g). Yield 0.4 g.

m/e 462 (M+1$^+$, 100%)

$^1$H NMR (D6-DMSO) δ 8.27 (2H, dt), 8.07 (1H, dd), 7.92 (1H, dd), 7.85 (1H, s), 7.60 (2H, d), 7.57 (1H, t), 5.38 (2H, s)

MP 208-211° C. decomposes

EXAMPLE 89

2,3-Dichloro-N-[5-chloro-3-(2-pyridinylmethoxy)-2-pyrazinyl]

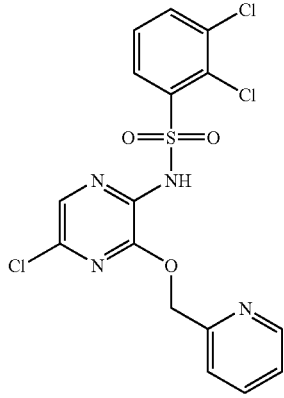

Prepared by the method of Example 31b using pyridine-2-methanol (0.2 g) and 2,3-dichloro-N-(3,5-dichloro-2-pyrazinyl)benzenesulphonamide (Example 74) (0.2 g). Yield 0.1 g.

m/e 445 (M+1$^+$, 100%)

$^1$H NMR (D6-DMSO) δ 8.58 (1H, dt), 8.08 (1H, dd), 7.92 (1H, dd), 7.80-7.90 (2H, m), 7.64 (1H, d), 7.56 (1H, t), 7.18-7.20 (1H, m), 5.47 (2H, s)

MP 147-148° C.

EXAMPLE 90

2,3-Dichloro-N-[5-chloro-3-(2-methylsulphanylethoxy)-2-pyrazinyl]benzenesulphonamide

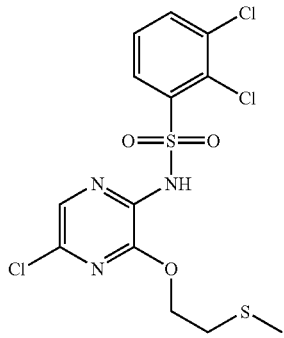

Prepared by the method of Example 31 using 2-methylsulphanylethanol (0.05 g) and 2,3-dichloro-N-(3,5-dichloro-2-pyrazinyl)benzenesulphonamide (Example 74) (0.1 g). Yield 0.06 g.

m/e 427 (M−1$^+$, 100%)

$^1$H NMR (D6-DMSO) δ 11.50-12.00 (1H, br s), 8.09 (1H, d), 7.95 (1H, d), 7.81 (1H, s), 7.60 (1H, t), 4.47 (2H, t), 2.86 (2H, t), 2.14 (3H, s)

MP 140-141° C.

EXAMPLE 91

N-(3-Butoxy-5-chloro-2-pyrazinyl)-2,3-dichlorobenzenesulphonamide

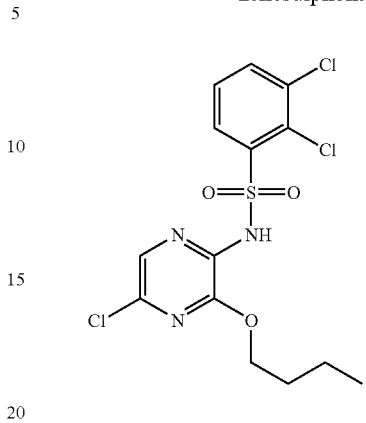

Prepared by the method of Example 31 using 1-butanol (0.05 g) and 2,3-dichloro-N-(3,5-dichloro-2-pyrazinyl)benzenesulphonamide (Example 74) (0.1 g). Yield 0.037 g.

m/e 410 (M+1$^+$, 100%)

$^1$H NMR (D6-DMSO) δ 8.08 (1H, d), 7.96 (1H, d), 7.79 (1H, s), 7.57 (1H, t), 4.29 (2H, t), 1.60-1.75 (2H, m), 1.40-1.50 (2H, m), 0.95 (3H, t)

MP 133-134° C.

EXAMPLE 92

2,3-Dichloro-N-[5-chloro-3-(2-methyl-3-pyridinylmethoxy)-2-pyrazinyl]benzenesulphonamide

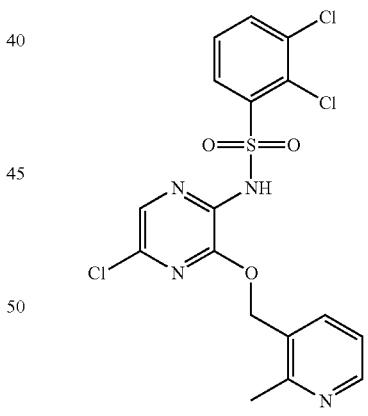

Prepared by the method of Example 31 using (2-methyl-3-pyridinyl)methanol (0.15 g) and 2,3-dichloro-N-(3,5-dichloro-2-pyrazinyl)benzenesulphonamide (Example 74) (0.15 g).

Yield 0.06g m/e 458 (M+1$^+$, 100%)

$^1$H NMR (D6-DMSO) δ 8.45 (1H, dd), 8.05 (1H, dd), 7.94 (1H, dd), 7.88 (1H, dd), 7.80 (1H, s), 7.53 (1H, t), 7.32 (1H, dd), 5.40 (2H, s), 2.56 (3H, s)

MP 214-216° C. decomposes

EXAMPLE 93

2,3-Dichloro-N-[5-chloro-3-(6-methyl-2-pyridinyl-methoxy)-2-pyrazinyl]benzenesulphonamide

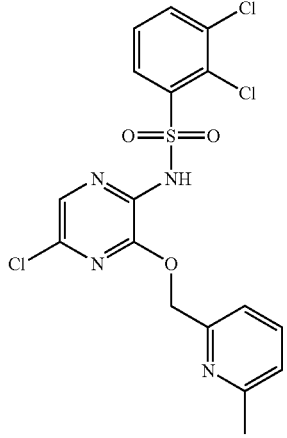

Prepared by the method of Example 31 using (6-methyl-2-pyridinyl)methanol (0.15 g) and 2,3-dichloro-N-(3,5-dichloro-2-pyrazinyl)benzenesulphonamide (Example 74) (0.15 g).

Yield 0.06 g.

m/e 461 (M+1$^+$, 100%)

$^1$H NMR (D6-DMSO) δ 8.08 (1H, dd), 7.91 (1H, dd), 7.84 (1H, s), 7.75 (1H, t), 7.55 (1H, t), 7.42 (1H, d), 7.24 (1H, d), 5.42 (2H, s), 2.52 (3H, s)

MP 158-159° C.

EXAMPLE 94

2,3-Dichloro-N-[5-chloro-3-(1-oxy-2-pyridinyl-methoxy)-2-pyrazinyl]benzenesulphonamide

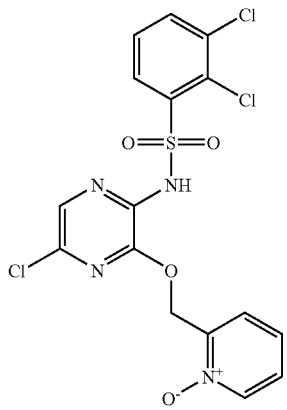

Prepared by the method of Example 86 using 2,3-dichloro-N-[5-chloro-3-(2-pyridinylmethoxy)-2-pyrazinyl]benzene-sulphonamide (Example 89) (0.2 g). Yield 0.1 g.

m/e 462 (M+1$^+$, 100%)

$^1$H NMR (D6-DMSO) δ 8.35-8.40 (1H, m), 8.09 (1H, dd), 7.80-7.90 (2H, m), 7.88 (1H, s), 7.58 (1H, t), 7.40-7.50 (2H, m), 5.51 (2H, s)

MP 222-224° C. decomposes

EXAMPLE 95

3-Chloro-N-[5-chloro-3-(3-pyridinylmethoxy)-2-pyrazinyl]-2-methylbenzenesulphonamide a) 5-Chloro-3-(3-pyridinylmethoxy)-2-pyrazinamine

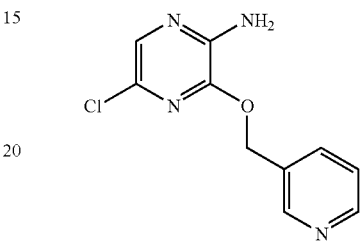

3,5-Dichloro-2-pyrazinamine (1.0 g) was added to a stirred suspension of pyridine-3-methanol (1.3 g) and sodium hydride (0.70 g of 60% dispersion in oil) in 1,2-dimethoxy-ethane (10 mL). After 0.5 h, 5% aqueous citric acid was added and the mixture extracted with ethyl acetate. Chromatography on silica gel eluting with ethyl acetate/iso-hexane mixtures gave the title compound as a white solid (0.2 g). Used directly.

b) 3-Chloro-N-[5-chloro-3-(3-pyridinylmethoxy)-2-pyrazinyl]-2-methylbenzenesulphonamide

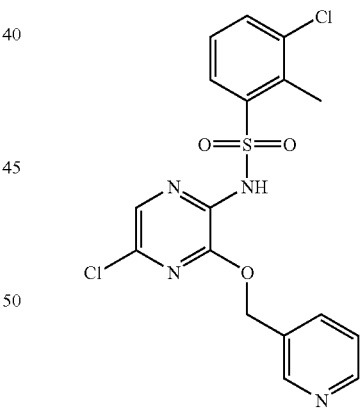

Prepared by the method of Example 1 (reaction performed at room temperature) using 5-chloro-3-(3-pyridinyl-methoxy)-2-pyrazinamine (Example 95a) (0.1 g) and 3-chloro-2-methylbenzenesulphonyl chloride (0.09 g). Yield 0.012 g.

m/e 425 (M+1$^+$, 100%)

$^1$H NMR (D6-DMSO) δ 8.78 (1H, d), 8.58 (1H, dd), 7.96 (2H, dt), 7.83 (1H, s), 7.72 (1H, d), 7.46 (1H, dd), 7.40 (1H, t), 5.44 (2H, s), 2.63 (3H, s)

MP 192-193° C.

EXAMPLE 96

3-Chloro-N-[5-chloro-3-(3-pyridinylmethoxy)-2-pyrazinyl]-2-fluorobenzenesulphonamide

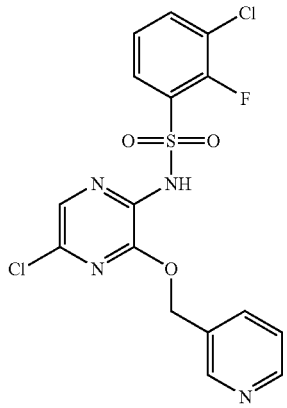

Prepared by the method of Example 1 (reaction performed at room temperature) using 5-chloro-3-(3-pyridinylmethoxy)-2-pyrazinamine (Example 95a) (0.1 g) and 3-chloro-2-fluorobenzenesulphonyl chloride (0.1 g). Yield 0.034 g.

m/e 429 (M+1$^+$, 100%)

$^1$H NMR (D6-DMSO) δ 8.78 (1H, d), 8.60 (1H, dd), 7.99 (1H, dt), 7.80-7.90 (3H, m), 7.48 (1H, dd), 7.40 (1H, t), 5.43 (2H, s)

MP 177-178° C.

EXAMPLE 97

2,3-Dichloro-N-[5-chloro-3-(4-methoxyphenylmethoxy)-2-pyrazinyl]benzenesulphonamide

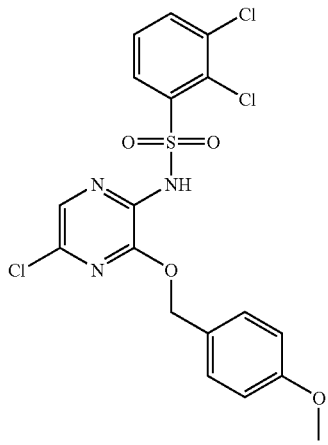

Prepared by the method of Example 31 using 4-methoxybenzylalcohol (0.3 g) and 2,3-dichloro-N-(3,5-dichloro-2-pyrazinyl)benzenesulphonamide (Example 74) (0.5 g). Yield 0.4 g.

m/e 475 (M+1$^+$, 100%)

$^1$H NMR (D6-DMSO) δ 8.05 (1H, dd), 7.91 (1H, dd), 7.81 (1H, s), 7.58 (1H, t), 7.42 (2H, d), 6.94 (2H, d), 5.32 (2H, s), 3.77 (3H, s)

MP 163-164° C.

EXAMPLE 98

N-[5-Bromo-6-chloro-2-pyrazinyl]-2,3-dichlorobenzenesulphonamide

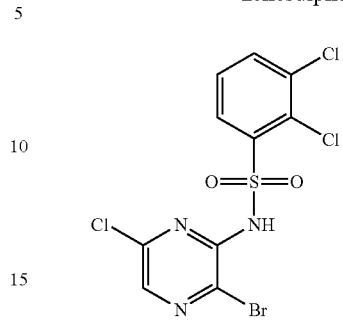

Prepared by the method of Example 1 (reaction performed at room temperature) using 3-bromo-5-chloro-2-pyrazinamine (Example 4a) (1.2 g) and 2,3-dichlorobenzenesulphonyl chloride (1.4 g). Yield 1.5 g.

m/e 418 (M+1$^+$, 100%)

$^1$H NMR (D6-DMSO) δ 8.07 (1H, dd), 7.90-7.80 (2H, m), 7.53 (1H, t)

MP 123-124° C.

EXAMPLE 99

2,3-Dichloro-N-[6-chloro-3-(3-pyridinylmethoxy)-2-pyrazinyl]benzenesulphonamide

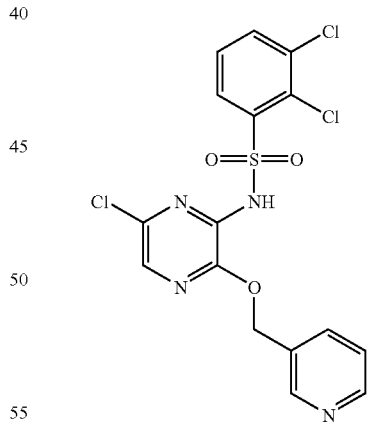

Prepared by the method of Example 31 using pyridine-3-methanol (0.22 g) and N-(3-bromo-6-chloro-2-pyrazinyl)-2,3-dichlorobenzenesulphonamide (Example 98) (0.2 g).

Yield 0.04 g.

m/e 445 (M+1$^+$, 100%)

$^1$H NMR (D6-DMSO) δ 8.77 (1H, br s), 8.59 (1H, dd), 8.12 (1H, dd), 8.00 (1H, dt), 7.92 (1H, dd), 7.84 (1H, s), 7.58 (1H, t), 7.55-7.50 (1H, m), 5.44 (2H, s)

MP 203-204° C.

EXAMPLE 100

2,3-Dichloro-N-[6-chloro-3-(2-pyridinylmethoxy)-2-pyrazinyl]benzenesulphonamide

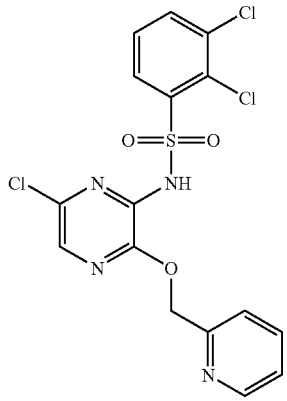

Prepared by the method of Example 31 using pyridine-2-methanol (0.22 g) and N-(3-bromo-6-chloro-2-pyrazinyl)-2,3-dichlorobenzenesulphonamide (Example 98) (0.2 g).

Yield 0.13 g.

m/e 445 (M+1$^+$, 100%)

$^1$H NMR (D6-DMSO) δ 8.56 (1H, dd), 8.15 (1H, dd), 7.94 (1H, dd), 7.90-7.80 (2H, m), 7.65-7.60 (1H, m), 7.58 (1H, s), 7.40-7.35 (1H, m), 5.48 (2H, s)

MP 201-203° C.

EXAMPLE 101

N-[5-(2-Aminoethylsulphanyl)-3-(2-pyridinylmethoxy)-2-pyrazinyl]-2,3-dichlorobenzenesulphonamide a) 2,3-Dichloro-N-[5-chloro-3-(3-pyridinylmethoxy)-2-pyrazinyl]-N-[2-trimethylsilanylethoxymethyl]benzenesulphonamide

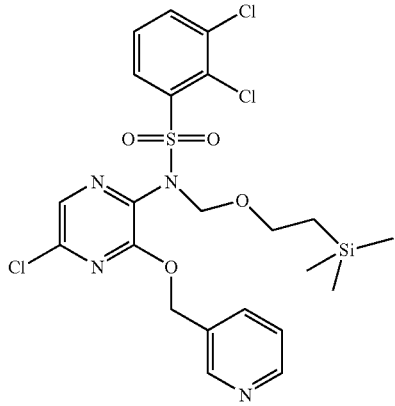

Prepared by the method of Example 66a using 2,3-dichloro-N-[5-chloro-3-(3-pyridinylmethoxy)-2-pyrazinyl]benzenesulphonamide (Example 36) (0.5 g). Yield 0.68 g. Used directly.

b) N-[5-(2-Aminoethylsulphanyl)-3-(2-pyridinylmethoxy)-2-pyrazinyl]-2,3-dichlorobenzenesulphonamide

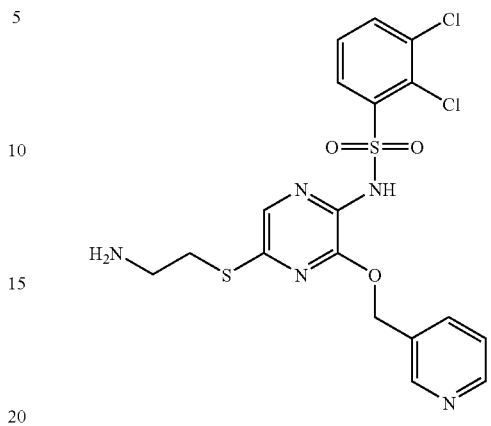

A mixture of 2,3-dichloro-N-[5-chloro-3-(3-pyridinylmethoxy)-2-pyrazinyl]-N-[2-trimethylsilanylethoxymethyl]benzenesulphonamide (Example 101a) (0.68 g), caesium carbonate (1.9 g) and 2-aminoethanethiol hydrochloride (0.2 g) in acetonitrile (5 mL) was stirred at room temperature for 5 h. Ethyl acetate was added and the mixture washed with water and brine. The organic layer was dried (MgSO$_4$) and evaporated. The residue was dissolved in trifluoracetic acid. After 1 h, toluene was added and the mixture evaporated to dryness. HCl (1M in dioxane) was added and the solid collected by filtration (0.2 g).

m/e 484 (M−1$^+$, 100%)

$^1$H NMR (D6-DMSO) δ 8.65 (1H, s), 8.52 (1H, d), 8.20-7.60 (2H, br s), 7.96 (1H, dd), 7.82 (1H, d), 7.62 (1H, d), 7.42-7.38 (1H, m), 7.35 (1H, t), 7.30 (1H, s), 5.24 (2H, s), 3.05-3.00 (2H, m), 2.85-2.80 (2H, m)

EXAMPLE 102

2,3-Dichloro-N-[5-chloro-3-(6-methoxy-3-pyridinylmethoxy)-2-pyrazinyl]benzenesulphonamide

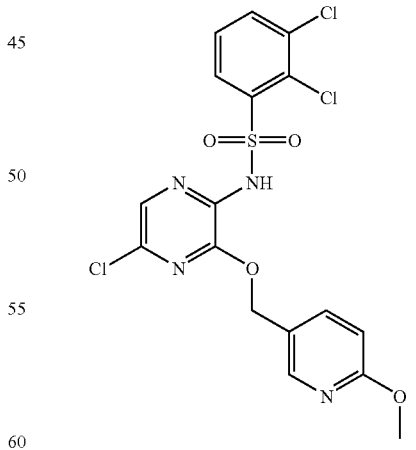

Prepared by the method of Example 31 using (6-methoxy-3-pyridinyl)methanol (0.3 g) and 2,3-dichloro-N-(3,5-dichloro-2-pyrazinyl)benzenesulphonamide (Example 74) (0.3 g).

Yield 0.15 g.

m/e 474 (M−1$^+$, 100%)

$^1$H NMR (D6-DMSO) δ 8.32 (1H, d), 8.04 (1H, dd), 7.91 (1H, dd), 7.85-7.80 (2H, m), 7.86 (1H, d), 7.55 (1H, t), 6.86 (1H, dd), 5.33 (2H, s), 3.87 (3H, s)

EXAMPLE 103

N-[3-(3-Bromophenylmethoxy)-5-chloro-2-pyrazinyl]-2,3-dichlorobenzenesulphonamide

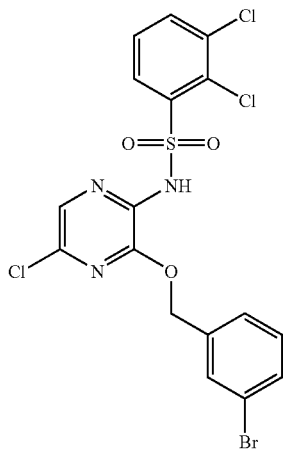

Prepared by the method of Example 31b using 3-bromobenzylalcohol (1.3 g) and 2,3-dichloro-N-(3,5-dichloro-2-pyrazinyl)benzenesulphonamide (Example 74) (1.1 g). Yield is 1.1 g.

m/e 522 (M+1$^+$, 100%)

$^1$H NMR (D6-DMSO) δ 8.07 (1H, dd), 7.92 (1H, dd), 7.85 (1H, s), 7.78 (1H, s), 7.60-7.50 (3H, m), 7.37 (1H, t), 5.40 (2H, s)

EXAMPLE 104

3-[6-Chloro-3-(2,3-dichlorobenzenesulphonylamino)-2-pyrazinyloxymethyl]benzoic acid methyl ester

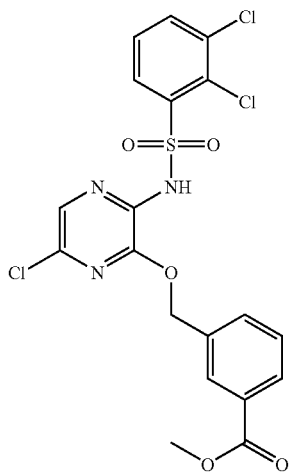

N-[3-(3-Bromophenylmethoxy)-5-chloro-2-pyrazinyl]-2,3-dichlorobenzenesulphonamide (Example 103) (1.0 g) and bis(triphenylphosphine)palladium dichloride (0.4 g) in methanol (15 mL) and triethylamine (7 mL) was heated at 100° C. under an atmosphere of carbon monoxide (6 barr). After 20 h, the mixture was filtered and evaporated. The residue was dissolved in ethyl acetate. The organic solution was washed with brine, aqueous citric acid, dried (MgSO$_4$) and evaporated. Chromatography on silica gel eluting with ethyl acetate/iso-hexane mixtures gave the title compound as a white solid (0.65 g).

m/e 503 (M+1$^+$, 100%)

$^1$H NMR (D6-DMSO) δ 8.11 (1H, s), 8.05 (1H, dd), 7.95 (1H, d), 7.90 (1H, dd), 7.84 (1H, s), 7.80 (1H, d), 7.60-7.50 (2H, m), 5.46 (2H, s), 3.88 (3H, s)

MP 175-176° C.

EXAMPLE 105

3-[6-Chloro-3-(2,3-dichlorobenzenesulphonylamino)-2-pyrazinyloxymethyl]benzoic acid

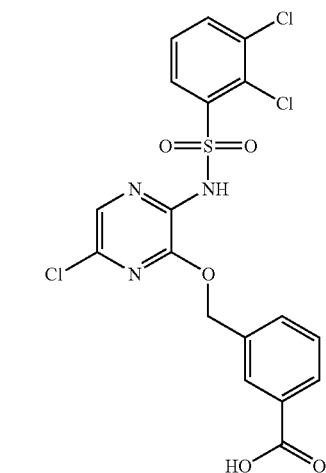

A mixture of 3-[6-chloro-3-(2,3-dichlorobenzenesulphonylamino)-2-pyrazinyloxymethyl]benzoic acid methyl ester (Example 104) (0.3 g) and lithium hydroxide hydrate (0.2 g) in water (5 mL) and methanol (5 mL) was stirred at room temperature. After 3 h, hydrochloric acid (2M) was added to acidify the mixture and the solid product was collected by filtration and dried (0.25 g).

m/e 489 (M+1$^+$, 100%)

$^1$H NMR (D6-DMSO) δ 13.10-13.00 (1H, br s), 12.00-11.80 (1H, br s), 8.10 (1H, s), 8.05 (1H, dd), 7.85-7.95 (2H, m), 7.82 (1H, s), 7.76 (1H, d), 7.54 (2H, t), 5.46 (2H, s)

MP 218-224° C. decomposes

EXAMPLE 106

2,3-Dichloro-N-[5-chloro-3-(3-hydroxymethylphenylmethoxy)-2-pyrazinyl]benzenesulphonamide a) 2,3-Dichloro-N-{5-chloro-3-[3-(tetrahydro-2-pyranyloxymethyl)phenylmethoxy]-2-pyrazinyl}benzenesulphonamide

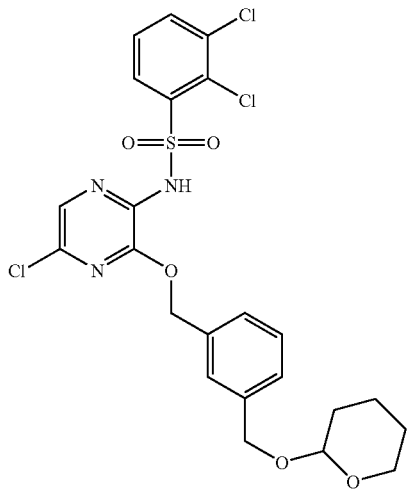

Prepared by the method of Example 31 using [3-(tetrahydro-2-pyranyloxymethyl)phenyl]methanol (1.99 g) and 2,3-dichloro-N-(3,5-dichloro-2-pyrazinyl)benzenesulphonamide (Example 74) (1.0 g). Yield 1.0 g. Used directly.

b) 2,3-Dichloro-N-[5-chloro-3-(3-hydroxymethylphenylmethoxy)-2-pyrazinyl]benzenesulphonamide

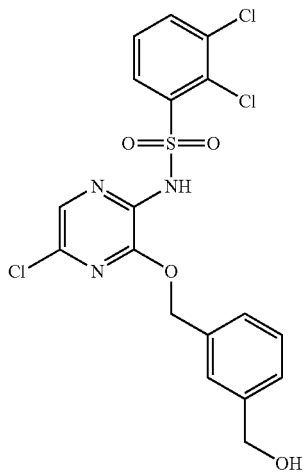

2,3-Dichloro-N-{5-chloro-3-[3-(tetrahydro-2-pyranyloxymethyl)phenylmethoxy]-2-pyrazinyl}benzenesulphonamide (Example 106a) (1.0 g) in acetic acid (40 mL), water (10 mL) and tetrahyrofuran (20 mL) was heated at 45° C. for 16 h and the solution was evaporated to dryness. Chromatography on silica gel eluting with ethyl acetate/iso-hexane mixtures gave the title compound as a white solid (0.6 g).

m/e 475 (M+1$^+$, 100%)

$^1$H NMR (D6-DMSO) δ 8.05 (1H, dd), 7.91 (1H, dd), 7.82 (1H, s), 7.55 (1H, t), 7.43 (1H, s), 7.40-7.25 (3H, m), 5.39 (2H, s), 4.52 (2H, s)

MP 162-163° C.

EXAMPLE 107

2,3-Dichloro-N-[5-chloro-3-(3-methylaminomethylphenylmethoxy)-2-pyrazinyl]benzenesulphonamide a) 2,3-Dichloro-N-[5-chloro-3-(3-formylphenylmethoxy)-2-pyrazinyl]benzenesulphonamide

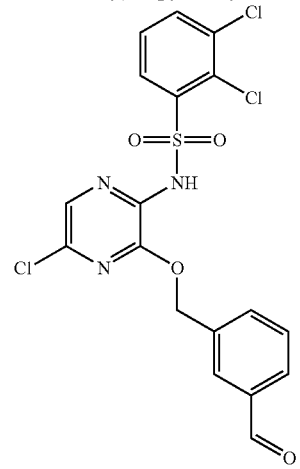

2,3-Dichloro-N-[5-chloro-3-(3-hydroxymethylphenylmethoxy)-2-pyrazinyl]benzenesulphonamide (Example 106) (0.6 g) and manganese dioxide (1.0 g) in tetrahydrofuran (5 mL) was stirred at room temperature for 16 h. The mixture was diluted with dichloromethane and filtered through celite. The solution was evaporated to dryness and the product crystallised from diethyl ether (0.4 g). Used directly.

b) 2,3-Dichloro-N-[5-chloro-3-(3-methylaminomethylphenylmethoxy)-2-pyrazinyl]benzenesulphonamide

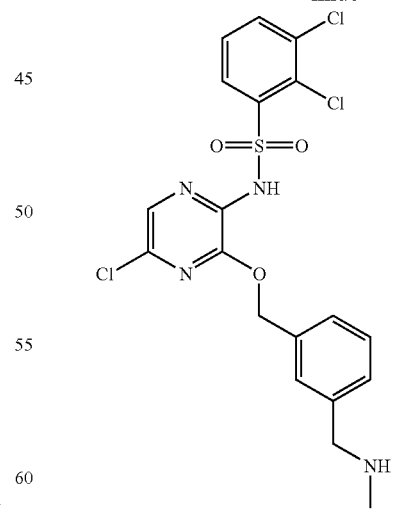

A mixture of 2,3-dichloro-N-[5-chloro-3-(3-formylphenylmethoxy)-2-pyrazinyl]benzenesulphonamide (Example 107a) (0.1 g), methylamine (2 mL of a 2M solution in tetrahydrofuran) and acetic acid (0.2 mL) in methanol (2 mL) was stirred at room temperature. After 2 h, sodium cyanoborohydride (0.03 g) was added. After 0.5 h, water (2 mL) was added and the mixture evaporated to dryness. Chromatography on silica gel eluting with methanol/dichloromethane mixtures gave the title compound as a white solid (0.035 g).

m/e 487 (M+1⁺, 100%)

$^1$H NMR (D6-DMSO) δ 8.90-8.60 (2H, br s), 8.02 (1H, d), 7.90-7.80 (1H, m), 7.80-7.60 (1H, m), 7.59 (1H, d), 7.55-7.40 (4H, m), 5.40 (2H, s), 4.08 (2H, s), 2.59 (3H, s)

MP 167-168° C.

EXAMPLE 108

2,3-Dichloro-N-[5-chloro-3-{3-([2-hydroxyethylamino]methyl)phenylmethoxy}-2-pyrazinyl]benzenesulphonamide

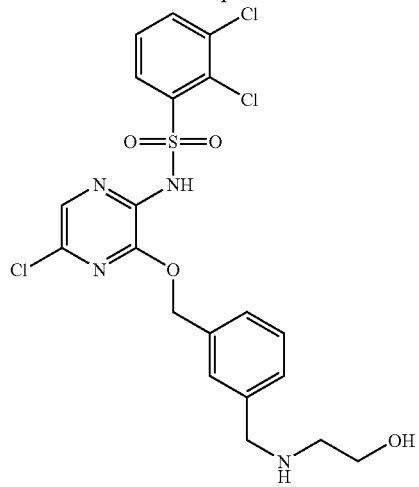

Prepared by the method of Example 107b using 2,3-dichloro-N-[5-chloro-3-(3-formylphenylmethoxy)-2-pyrazinyl]benzenesulphonamide (Example 107a) (0.1 g) and 2-aminoethanol (0.05 g). Yield 0.035 g.

m/e 517 (M+1⁺, 100%)

$^1$H NMR (D6-DMSO) δ 9.00-8.80 (2H, br s), 7.93 (1H, d), 7.80-7.20 (7H, m), 5.28 (2H, s), 5.21 (1H, t), 4.20 (2H, s), 3.80-3.60 (2H, m), 3.05-2.95 (2H, m)

MP 196-198° C.

EXAMPLE 109

2,3-Dichloro-N-[5-chloro-3-(4-hydroxymethylphenylmethoxy)-2-pyrazinyl]benzenesulphonamide

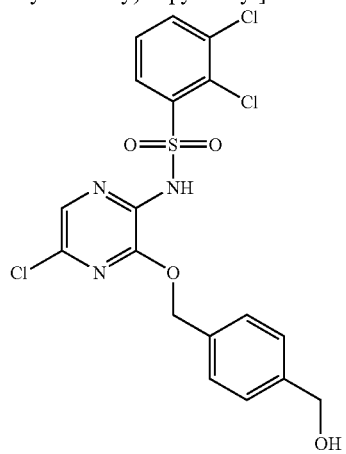

Prepared by the method of Examples 106a and 106b using [4-(tetrahydro-2-pyranyloxymethyl)phenyl]methanol (2.0 g) and 2,3-dichloro-N-(3,5-dichloro-2-pyrazinyl)benzenesulphonamide (Example 74) (1.0 g). Yield 0.7 g.

m/e 474 (M−1⁺, 100%)

$^1$H NMR (D6-DMSO) δ 8.05 (1H, dd), 7.91 (1H, dd), 7.83 (1H, s), 7.55 (1H, t), 7.46 (2H, d), 7.33 (2H, d), 5.38 (2H, s), 4.51 (2H, s)

MP 177-178° C.

EXAMPLE 110

2,3-Dichloro-N-[5-chloro-3-{4-([2-hydroxyethylamino]methyl)phenylmethoxy}-2-pyrazinyl]benzenesulphonamide a) 2,3-Dichloro-N-[5-chloro-3-(4-formylphenylmethoxy)-2-pyrazinyl]benzenesulphonamide

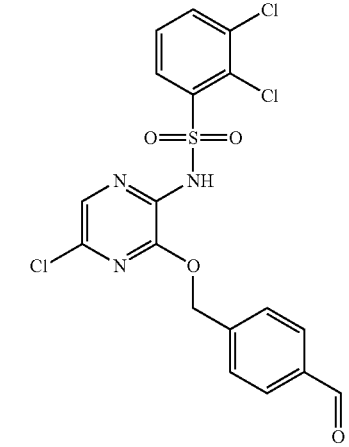

Prepared by the method of Example 107a using 2,3-dichloro-N-[5-chloro-3-(4-hydroxymethylphenylmethoxy)-2-pyrazinyl]benzenesulphonamide (Example 109) (0.65 g). Yield 0.64 g. Used directly.

b) 2,3-Dichloro-N-(5-chloro-3-{4-[(2-hydroxyethylamino)methyl]phenylmethoxy}-2-pyrazinyl]benzenesulphonamide

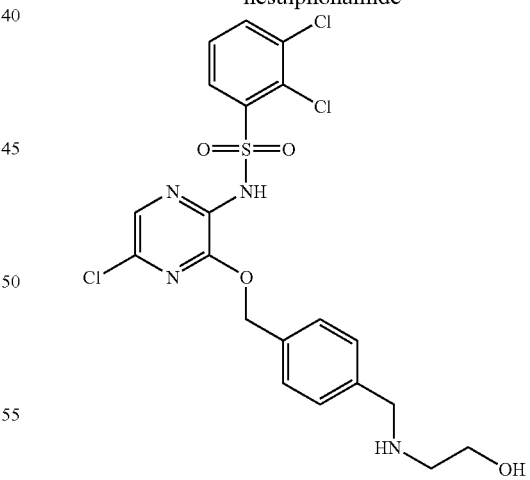

Prepared by the method of Example 107b using 2,3-dichloro-N-[5-chloro-4-(3-formylphenylmethoxy)-2-pyrazinyl]benzenesulphonamide (Example 110a) (0.1 g) and 2-aminoethanol (0.05 g). Yield 0.028 g.

m/e 517 (M+1⁺, 100%)

$^1$H NMR (D6-DMSO) δ 8.75 (2H, br s), 7.93 (1H, dd), 7.61 (1H, dd), 7.54 (4H, s), 7.35 (1H, t), 7.26 (1H, s), 5.26 (2H, s), 5.18 (1H, t), 4.18 (2H, s), 3.70-3.60 (2H, m), 3.00-2.95 (2H, m)

MP 202-205° C.

EXAMPLE 111

2,3-Dichloro-N-[3-(4-hydroxymethylphenyl-methoxy)-2-pyrazinyl]benzenesulphonamide a) 2,3-Dichloro-N-{3-[4-(tetrahydro-2-pyranyloxym-ethyl)phenylmethoxy]-2-pyrazinyl}benzenesulphonamide

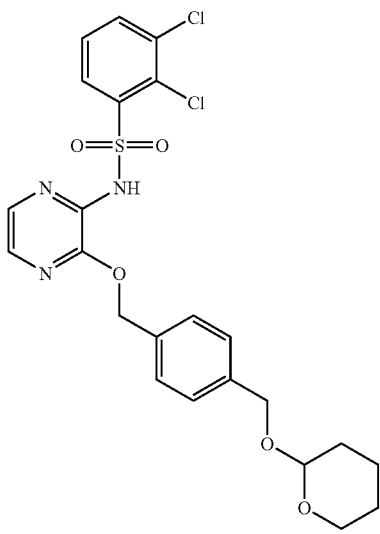

2,3-Dichloro-N-(3-chloro-2-pyrazinyl)benzenesulphona-mide (Example 28a) (0.1 g), [4-(tetrahydro-2-pyranyloxym-ethyl)phenyl]methanol (0.27 g) and potassium tert-butoxide (2 mL of a 1M solution in tetrahydrofuran) in N-methylpyr-rolidinone (1 mL) was stirred at 50° C. After 2 h, aqueous citric acid was added and the mixture extracted with ethyl acetate. The organic solution was washed with water and brine and evaporated to dryness. Used directly.

b) 2,3-Dichloro-N-[3-(4-hydroxymethylphenyl-methoxy)-2-pyrazinyl]benzenesulphonamide

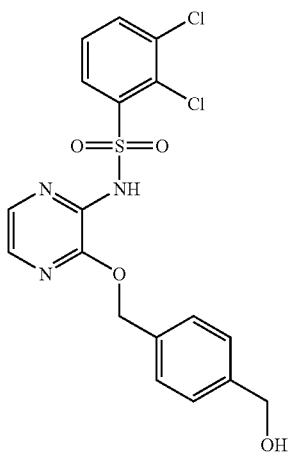

2,3-Dichloro-N-{3-[4-(tetrahydro-2-pyranyloxymethyl)phenylmethoxy]-2-pyrazinyl}benzenesulphonamide (Example 11a) in acetic acid (10 mL), water (2.5 mL) and tet-rahydrofuran (5 mL) was heated at 45° C. for 16 h and the solution was evaporated to is dryness. Chromatography on silica gel eluting with ethyl acetate/iso-hexane mixtures gave the title compound as a white solid (0.022 g).

m/e 440 (M+1+, 100%)

$^1$H NMR (D6-DMSO) 8.08 (1H, dd), 7.91 (1H, dd), 7.90-7.70 (1H, br s), 7.70-7.60 (1H, br s), 7.55 (1H, t), 7.42 (2H, d), 7.31 (2H, d), 5.39 (2H, s), 5.20-5.05 (1H, br s), 4.49 (2H, s)

MP 160-161° C.

EXAMPLE 112

2,3-Dichloro-N-[5-chloro-3-(2-hydroxymethylphe-nylmethoxy)-2-pyrazinyl]benzenesulphonamide

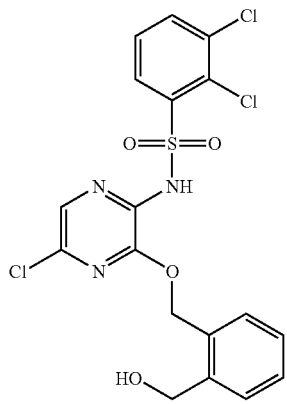

2,3-Dichloro-N-(3,5-dichloro-2-pyrazinyl)benzene-sulphonamide (Example 74). (0.15 g), (2-hydroxymeth-ylphenyl)methanol (0.27 g) and potassium tert-butoxide (3 mL of a 1M solution in tetrahydrofuran) in N-methylpyrroli-dinone (2 mL) was stirred at room temperature. After 1 h, aqueous citric acid was added and the mixture extracted with ethyl acetate. The organic solution was washed with water and brine and evaporated to dryness. Chromatography on silica gel eluting with ethyl acetate/iso-hexane mixtures gave the title compound as a white solid (0.027 g).

m/e 474 (M+1+, 100%)

$^1$H NMR (D6-DMSO) δ 8.06 (1H, dd), 7.90 (1H, dd), 7.81 (1H, s), 7.60-7.40 (3H, m), 7.37 (1H, t), 7.29 (1H, t), 5.45 (2H, s), 4.64 (2H, s)

MP 145-146° C.

EXAMPLE 113

5-(2,3-Dichlorobenzenesuphonylamino)-6-methoxy-pyrazine-2-carboxylic acid, methyl ester

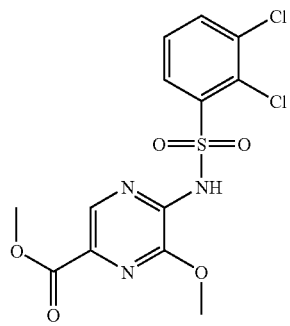

N-(5-Bromo-3-methoxy-2-pyrazinyl)-2,3-dichlorobenzenesulphonamide (Example 8) (6.5 g) and dichloro[1,1'-bis(diphenylphosphino)ferrocene]palladium(II) dichloromethane adduct (0.7 g) in methanol (30 mL) and triethylamine (10 mL) was heated at 100° C. under an atmosphere of carbon monoxide (6 bar). After 5 h, the mixture was filtered and evaporated. The residue was dissolved in ethyl acetate. The organic solution was washed with brine, aqueous citric acid, dried (MgSO$_4$) and evaporated. Chromatography on silica gel eluting with ethyl acetate/iso-hexane mixtures gave the title compound as a white solid (4.8 g).

m/e 392 (M+1$^+$, 100%)

$^1$H NMR (D6-DMSO) δ 8.13 (2H, dd), 7.95 (1H, dd), 7.60 (1H, t), 3.95 (3H, s), 3.82 (3H, s)

MP 120-121° C.

EXAMPLE 114

2,3-Dichloro-N-[5-(1-hydroxy-1-methylethyl)-3-methoxy-2-pyrazinyl]benzenesulphonamide

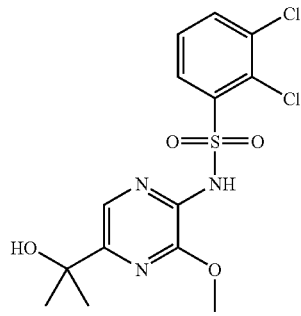

Methylmagnesium bromide (3 mL of a 3M solution in diethyl ether) was added over 3 minutes to a stirred solution of 5-(2,3-dichlorobenzenesuphonylamino)-6-methoxypyrazine-2-carboxylic acid, methyl ester (Example 113) (0.3 g) in tetrahydrofuran (10 mL) cooled in an ice/water bath. After a further 5 minutes, aqueous citric acid was added and the mixture extracted with ethyl acetate. The organic solution was evaporated to dryness. Chromatography on silica gel eluting with methanol/dichloromethane mixtures gave the title compound as a white solid (0.15 g).

m/e 392 (M+1$^+$, 100%)

$^1$H NMR (D6-DMSO) δ 11.40-11.30 (1H, br s), 8.07 (1H, dd), 7.93 (1H, d), 7.90-7.80 (1H, br s), 7.59 (1H, t), 5.10-5.05 (1H, br s), 3.88 (3H, s), 1.39 (6H, s)

MP 192-193° C.

EXAMPLE 115

N-[5-(2-Aminoethoxy)-3-methoxy-2-pyrazinyl]-2,3-dichlorobenzenesulphonamide a) 2,3-Dichloro-N-(5-chloro-3-methoxy-2-pyrazinyl)-N-{[2-(trimethylsilyl)ethoxy]methyl}benzenesulphonamide

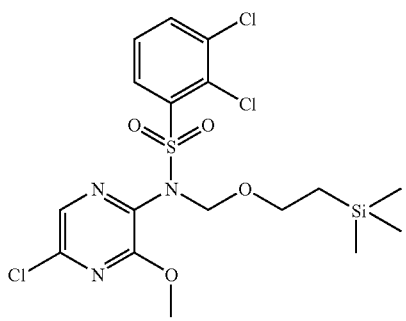

Prepared by the method of Example 66a using 2,3-dichloro-N-(5-chloro-3-methoxy-2-pyrazinyl)benzenesulphonamide (Example 5) (7.0 g). Yield 9.8 g. Used directly.

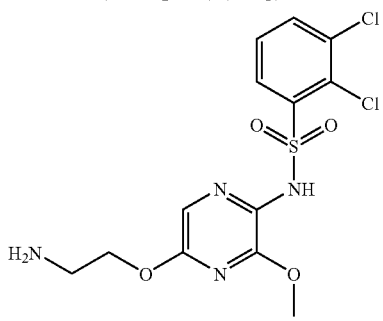

b) N-[5-(2-aminoethoxy)-3-methoxy-2-pyrazinyl]-2,3-dichlorobenzenesulphonamide 2,3-Dichloro-N-(5-chloro-3-methoxy-2-pyrazinyl)-N-{[2-(trimethylsilyl)ethoxy]methyl}benzenesulphonamide (Example 115a) (0.25 g) was added to a mixture of ethanolamine (0.05 mL) and sodium hydride (0.035 g of a 60% dispersion in oil) in 1,2-dimethoxyethane (15 mL) at room temperature. After 2 h, the mixture was partitioned between water and ethyl acetate. The organic layer was washed with brine, dried (MgSO$_4$) and evaporated to dryness. Chromatography on silica gel eluting with methanol/dichloromethane mixtures gave the title compound containing the SEM ([2-(trimethylsilyl)ethoxy]methyl) protecting group as an oil (0.14 g). Trifluoroacetic acid (1 mL) and dichloromethane (3 mL) were added. After 0.5 h at room temperature, toluene was added and the solution evaporated to dryness. HCl (4M in dioxane) was added and the mixture evaporated to dryness. The product was crystallised from diethyl ether (0.075 g).

m/e 393 (M+1$^+$, 100%)

$^1$H NMR (D6-DMSO) δ 10.90 (1H, br s), 8.07 (2H, br s), 7.99-7.92 (2H, m), 7.56 (1H, 7.49 (1H, s), 4.45 (2H, t), 3.84 (3H, s), 3.25-3.20 (2H, m)

MP 200-205° C.

EXAMPLE 116

N-{5-[(2-Aminoethyl)thio]-6-chloro-3-methoxy-2-pyrazinyl}-2,3-dichlorobenzenesulfonamide

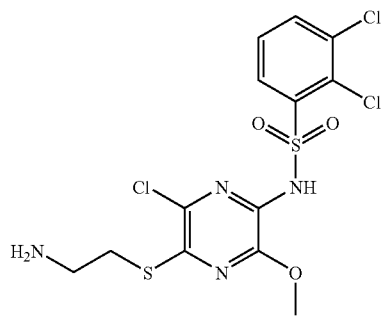

Prepared by the method of Example 101b using 2,3-dichloro-N-(5,6-dichloro-3-methoxy-2-pyrazinyl)-N-{[2-(trimethylsilyl)ethoxy]methyl}benzenesulphonamide (Example 66a) (0.27 g). Yield 0.055 g.

m/e 443 (M+1$^+$, 100%)

$^1$H NMR (D6-DMSO) δ 8.09 (1H, d), 7.90 (1H, d), 7.58 (1H, t), 3.95 (3H, s), 3.33 (2H, t), 3.14 (2H, t).

MP 185-190° C.

EXAMPLE 117

3-[(5-{[(2,3-Dichlorophenyl)sulphonyl]amino}-6-methoxy-2-pyrazinyl)thio]propanoic acid, methyl ester

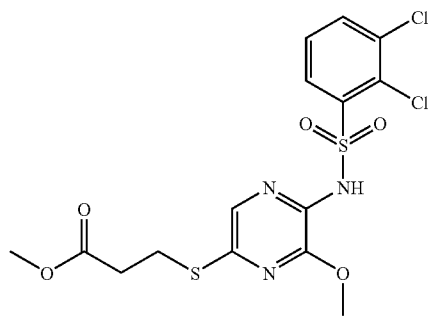

Prepared by the method of Example 101b using 2,3-dichloro-N-(5-chloro-3-methoxy-2-pyrazinyl)-N-{[2-(trimethylsilyl)ethoxy]methyl}benzenesulphonamide (Example 115a) (0.25 g) and 3-mercaptopropionic acid, methyl ester (0.06 mL). Yield 0.1 g.

m/e 452 (M+1$^+$, 100%)

$^1$H NMR (D6-DMSO) δ 11.35 (1H, br s), 8.03 (1H, d), 7.93 (1H, d), 7.66 (1H, s), 7.57 (1H, t), 3.90 (3H, s), 3.58 (3H, s), 3.29 (2H, t), 2.72 (2H, t).

MP 146-148° C.

EXAMPLE 118

2,3-Dichloro-N-[5-bromo-3-methoxy-6-methyl-2-pyrazinyl)benzenesulphonamide a) 6-Methyl-2-pyrazinamine

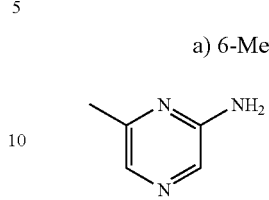

Dimethylzinc (100 mL of a 2$\underline{M}$ solution in toluene) was added dropwise over 0.5 h to a stirred solution of 6-chloro-2-pyrazinamine (12.9 g) and [1,3-bis(diphenylphosphino)propane]nickel(II) chloride (5.4 g) in dioxane (200 mL) under a nitrogen atmosphere. The reaction mixture was heated at reflux for 18 h, then cooled to room temperature and quenched cautiously with iso-propanol (30 mL) and methanol (50 mL). After removal of solvent in vacuo, the residue was partitioned between dichloromethane and aqueous ammonium chloride. The organic phase was filtered through celite, dried (MgSO$_4$), filtered and evaporated to give the crude product as an orange solid. Chromatography on silica gel eluting with ethyl acetate/methanol mixtures gave the title compound (5.1 g). Used directly.

b) 3,5-Dibromo-6-methyl-2-pyrazinamine

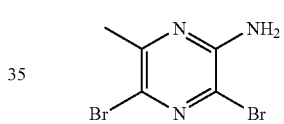

A solution of bromine (1.85 g) in chloroform (5 mL) was added dropwise to a stirred solution of 2-amino-6-methylpyrazine (Example 118a) (0.6 g) in chloroform (50 mL). The reaction mixture was stirred at room temperature for 0.5 h, then washed twice with water, dried (MgSO$_4$), filtered and evaporated to give the crude product as an orange solid. Chromatography on silica gel eluting with dichloromethane gave the title compound (0.95 g). Used directly.

c) 5-Bromo-3-methoxy-6-methyl-2-pyrazinamine

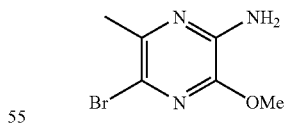

A solution of 3,5-dibromo-6-methyl-2-pyrazinamine (Example 118b) (0.9 g) was added to a solution of sodium (0.39 g) in methanol (30 mL) was heated at reflux for 18 h. After removal of solvent in vacuo, the residue was partitioned between water and dichloromethane, and the organic phase dried (MgSO$_4$), filtered and evaporated to give the title compound as a pale yellow solid (0.58 g).

m/e 218/220(M+1$^+$, 100%)

$^1$H NMR (CDCl$_3$) δ 4.70 (2H, br s), 3.97 (3H, s), 2.40 (3H, s)

d) 2,3-Dichloro-N-[5-bromo-3-methoxy-6-methyl-2-pyrazinyl)benzenesulphonamide

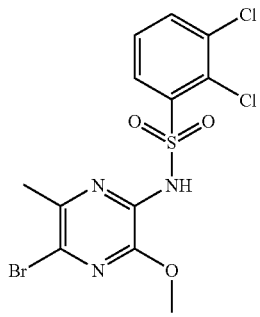

Sodium hydride (0.5 g of a 60% dispersion in oil) was added to a solution of 5-bromo-3-methoxy-6-methyl-2-pyrazinamine (Example 118c) (0.55 g) in N-methylpyrrolidinone (25 mL). The resultant dark solution was stirred at room temperature for 0.5 h before a solution of 2,3-dichlorobenzenesulphonyl chloride (0.67 g) in N-methylpyrrolidinone (5 mL) was added dropwise. The reaction mixture was stirred at room temperature for 3 h, then quenched with aqueous ammonium chloride and partitioned between ethyl acetate and aqueous ammonium chloride (×5). the organic phase was dried (MgSO$_4$), filtered and evaporated to give the crude product. Chromatography on silica gel eluting with dichloromethane/acetic acid (200:1) gave the title compound as a pale yellow solid (0.38 g).

m/e 424/426/428 (M−1$^-$, 100%)

$^1$H NMR (CDCl$_3$) δ 8.29 (1H, d), 7.69 (2H, d), 7.41 (1H, t), 4.01 (3H, s), 2.27 (3H, s)

MP 146-148° C.

EXAMPLE 119

5-(2,3-Dichlorobenzenesulphonylamino)-6-methoxy-3-methylpyrazine-2-carboxylic aicd, methyl ester

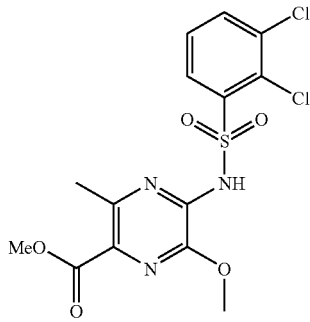

Prepared by the method of Example 113 using 2,3-dichloro-N-[5-bromo-3-methoxy-6-methylpyrazinyl)benzenesulphonamide (Example 118) (0.35 g). Yield 0.27 g.

m/e 404/406 (M−1$^-$, 100%)

$^1$H NMR (CDCl$_3$) δ 8.32 (1H, br s), 8.10 (1H, br s), 7.70 (1H, d), 7.42 (1H, t) 4.06 (3H, s), 3.90 (3H, s), 2.50 (3H, br s).

MP 149-150° C.

EXAMPLE 120

2,3-Dichloro-N-[5-(hydroxymethyl)-3-methoxy-6-methyl-2-pyrazinyl)benzenesulphonamide

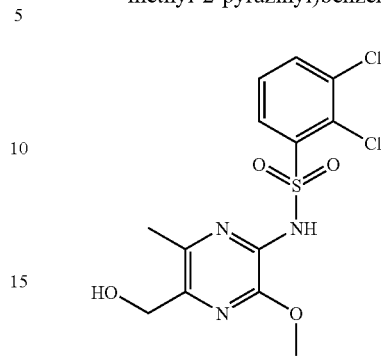

To a stirred solution of 5-(2,3-dichlorobenzenesulphonylamino)-6-methoxy-3-methylpyrazine-2-carboxylic aicd, methyl ester (Example 119) (0.19 g) in tetrahydrofuran (10 mL) under an atmosphere of nitrogen was added a solution of lithium triethylborohydride (1.7 mL of a 1M solution in tetrahydrofuran). The reaction mixture was stirred at room temperature for 1 h, before quenching with aqueous ammonium chloride and extraction into dichloromethane. The organic phase was dried (MgSO$_4$), filtered and evaporated to give the crude product as a colourless oil. Chromatography on silica gel eluting with dichloromethane/ethyl acetate/acetic acid (150:50: 1) gave the title compound as a white solid (0.38 g).

m/e 378 (M+1$^+$, 100%)

$^1$H NMR (CDCl$_3$) δ 8.31 (1H, br d), 7.77 (1H, br s), 7.68 (1H, d), 7.41 (1H, t), 4.55 (2H, d), 4.03 (3H, s), 3.12 (1H, br s), 2.13 (3H, br s).

MP 175-177° C.

EXAMPLE 121

2,3-Dichloro-N-[5,6-dichloro-3-(3-pyridinyl-methoxy)-2-pyrazinyl]benzenesulphonamide a)
5,6-Dichloro-3-(3-pyridinylmethoxy)-2-pyrazinamine

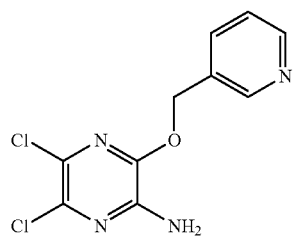

To a stirred suspension of sodium hydride (1.20 g of a 60% dispersion in oil) in dry dimethoxymethane (40 mL) was added pyridine-3-methanol (2.18 g) in 1,2-dimethoxymethane (10 mL). The resulting suspension was stirred at room temperature for 0.5 h and then 3,5,6-trichloro-2-aminopyrazine (1.2 g) was added and the mixture stirred at 70° C. for 4 h. The reaction mixture was cooled and cautiously added to water (100 mL) and neutralised with 2M hydrochloric acid. The mixture was extracted with ethyl acetate (2×50 mL), dried (MgSO$_4$), filtered and concentrated. The residue was purified by chromatography on silical gel eluting with ethyl acetate to afford the sub-titled compound as a white solid (0.29 g).

$^1$H NMR (CDCl$_3$) δ 8.73 (1H, s), 8.63 (1H, d), 7.8 (1H, d), 7.35 (1H, dd), 5.42 (2H, s), 4.92 (2H, br s).

b) 2,3-Dichloro-N-[5,6-dichloro-3-(3-pyridinylmethoxy)-2-pyrazinyl]benzenesulphonamide

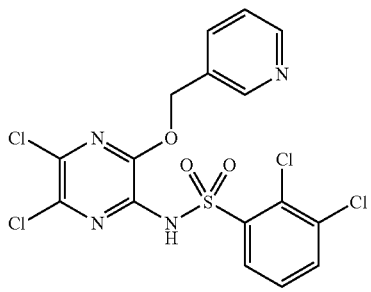

Prepared by the method of Example 1 (reaction performed at room temperature) using 5,6-dichloro-3-(3-pyridinylmethoxy)-2-pyrazinamine (Example 121a) (0.27 g) and 2,3-dichlorobenzenesulphonyl chloride (0.27 g). Yield 0.17 g.

m/e 479 (M+1$^+$, 100%)

$^1$H NMR (D6-DMSO) δ 8.8 (1H, s), 8.63 (1H, d), 8.11 (1H, d), 8.06 (1H, d), 7.58-7.52 (2H, m), 5.41 (2H, s).

EXAMPLE 122

3-Chloro-N-(5-chloro-3-methoxy-2-pyrazinyl)-2-fluorobenzenesulphonamide

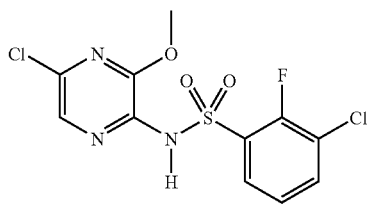

Prepared by the method of Example 1 (reaction performed at room temperature) using 5-chloro-3-methoxy-2-pyrazinamine (0.16 g) and 3-chloro-2-fluorobenzenesulphonyl chloride (0.27 g). Yield 0.22 g.

m/e 354,352 (M+1$^+$, 100%)

$^1$H NMR (D6-DMSO) δ 7.94-7.86 (2H, m), 7.82 (1H, s), 7.43 (1H, dt), 3.92 (3H, s).

MP 156-157° C.

EXAMPLE 123

3-Chloro-2-fluoro-N-[3-(3-pyridinylmethoxy)-2-pyrazinyl]benzenesulphonamide a) 3-(3-Pyridinylmethoxy)-2-pyrazinamine

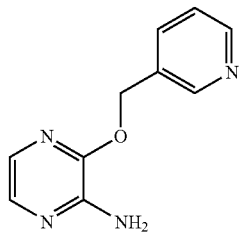

Prepared as for Example 121a using 3-chloro-2-aminopyrazine (0.5 g), pyridine-3-methanol (0.42 g) and sodium hydride (0.31 g of a 60% dispersion in oil) in N-methylpyrrolidinone (5 mL) to afford the sub-titled compound as a solid (0.62 g).

$^1$H NMR (CDCl$_3$) δ 8.73 (1H, d), 8.60 (1H, d), 7.78 (1H, d), 7.60 (1H, d), 7.42 (1H, d), 7.32 (1H, dd), 5.43 (2H, s), 4.77 (2H, br).

MP 120-122° C.

b) 3-Chloro-2-fluoro-N-[3-(3-pyridinylmethoxy)-2-pyrazinyl]benzenesulphonamide

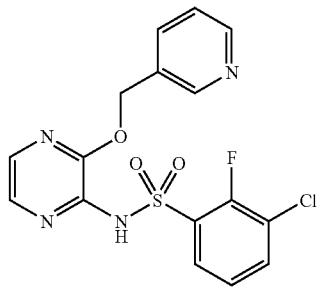

To a stirred solution of 3-(3-pyridinylmethoxy)-2-pyrazinamine (Example 122a) (0.404 g) in dichloromethane (5 mL) and pyridine (1 mL) was added iso-butylchloroformate (0.3 mL) and the resulting solution stirred for 20 hours. The reaction mixture was poured into water (20 mL) and extracted into ethyl acetate (2×20 mL). The combined extracts were dried (MgSO$_4$), filtered and concentrated to afford an oil (0.51 g) that was used without further purification. A portion of the residue (0.15 g) was dissolved in 1,2-dimethoxymethane (2 mL) and sodium hydride (0.030 g of 60% dispersion in oil) added. The resulting suspension was stirred for 15 minutes and then 3-chloro-2-fluorobenzenesulfonyl chloride (0.137 g) in dimethoxymethane (1 mL) was added. The resulting solution was stirred at room temperature for 6 h. The reaction mixture was poured into water (20 mL) and extracted into ethyl acetate (2×20 mL). The combined extracts were dried (MgSO$_4$), filtered and concentrated to afford an oil that was dissolved into methanol (5 mL) and water (2 mL) and sodium hydroxide (0.04 g) was added. The mixture was heated to 60° C. for 1 hour, cooled and was poured into water (20 mL) and extracted into ethyl acetate (2×20 ml). The combined extracts were dried (MgSO$_4$), filtered and concentrated to afford an oil that was purified by chromatography on silica gel eluting with ethyl acetate/iso-hexane mixtures followed by ethyl acetate to afford the title compound (0.067 g) as a white solid.

m/e 395, 397 (M+1⁺, 100%)

¹H NMR (CDCl₃) δ 8.69 (1H, s), 8.62 (1H, d), 8.06 (1H, t), 7.78 (1H, d), 7.68 (1H, d), 7.69-7.60 (2H, m), 7.34 (1H, dd), 7.26 (1H, dd), 5.43 (2H, s).

EXAMPLE 124

3-{[(2,3-Dichlorophenyl)sulphonyl]amino}pyrazine-2-carboxylic acid, methyl ester

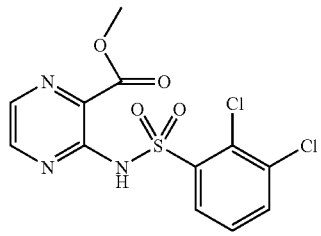

To a stirred solution of 2,3-dichlorobenzenesulphonyl chloride (0.246 g) and methyl-3-aminopyrazine-2-carboxylate (0.153 g) in 1,2-dimethoxymethane (3 mL) was added portionwise sodium hydride (0.1 g of a 60% dispersion in oil) over 1 hour. The mixture was stirred at room temperature for 20 h, was poured into water (20 mL) and extracted into ethyl acetate (2×20 mL). The combined extracts were dried (MgSO₄), filtered and concentrated to afford an oil that was purified by chromatography on silica gel eluting with dichloromethane to afford the titled compound (0.085 g) as a white solid.

m/e 362/364 (M+1⁺, 100%)

¹H NMR (CDCl₃) δ 10.97 (1H, s), 8.32 (1H, dd), 8.31 (1H, d), 8.25 (1H, d), 7.68 (1H, dd), 7.42 (1H, t), 4.08 (3H, s).

MP 177-178° C.

EXAMPLE 125

N-(5-Bromo-6-chloro-3-methoxy-2-pyrazinyl)-2,3-dichlorobenzenesulphonamide a) 3-Methoxy-5-bromo-6-chloro-2-pyrazinamine

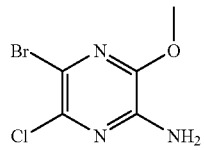

A stirred solution of 2-amino-6-chloropyrazine (2.0 g) and N-bromosuccinimide (13.71 g) in chloroform (100 mL) was heated to reflux for 20 hours. The reaction mixture was cooled and concentrated onto silica gel (20 g) and the residue loaded onto a column of silica gel (5cm×2cm) and the column was eluted with dichloromethane. Concentration afforded 3,5-dibromo-6-chloro-2-aminopyrazine that was dissolved into methanol (200 mL) and sodium methoxide (32 g of a 25% solution in methanol) added. The reaction was heated to 70° C. for 1.5 h, cooled and concentrated to approx. 50 mL capacity. The reaction mixture was poured into water (200 mL) and the sub-titled adduct (2.0 g) collected as an off-white solid.

m/e 235, 237 (M+1⁺, 100%)

b) N-(5-Bromo-6-chloro-3-methoxy-2-pyrazinyl)-2,3-dichlorobenzenesulphonamide

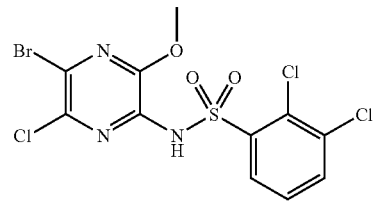

Procedure as for Example 1 (reaction performed at room temperature) using 3-methoxy-5-bromo-6-chloro-2-pyrazinamine (Example 125a) (0.5 g) and 2,3-dichlorobenzenesulphonyl chloride (2.21 g). Yield 3.2 g.

m/e 445,447 (M−1⁺, 100%)

¹H NMR (CDCl₃) δ 8.32 (1H, dd), 7.79 (1H, br), 7.72 (1H, dd), 7.45 (1H, t), 4.05 (3H, s).

MP 177-178° C.

EXAMPLE 126

3-Chloro-5-{[(2,3-dichlorophenyl)sulphonyl]amino}-6-methoxypyrazine-2-carboxylic acid, methyl ester

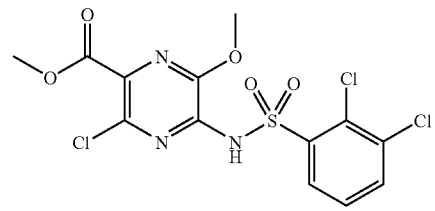

Prepared by the method of Example 113 using N-(5-bromo-6-chloro-3-methoxypyrazin-2-yl)-2,3-dichlorobenzenesulfonamide (Example 125) (1.0 g). Yield 0.92 g.

m/e 426, 428 (M−1⁺, 100%)

¹H NMR (CDCl₃) δ 8.36 (1H, dd), 8.05 (1H, br), 7.73 (1H, dd), 7.47 (1H, t), 4.09 (3H, s), 3.92 (3H, s).

MP 200-201° C.

EXAMPLE 127

2,3-Dichloro-N-[6-chloro-5-(hydroxymethyl)-3-methoxypyrazin-2-yl]benzenesulphonamide

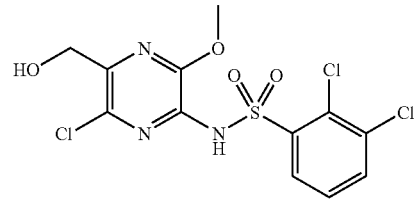

Prepared as for Example 120 using 3-chloro-5-{[(2,3-dichlorophenyl)sulphonyl]amino}-6-methoxypyrazine-2-carboxylic acid, methyl ester (Example 126) (0.105 g). Yield 0.072 g.

m/e 397, 399 (M−1⁺, 100%)

¹H NMR (CDCl₃) δ 8.34 (1H, dd), 7.84 (1H, br), 7.74 (1H, dd), 7.45 (1H, t), 4.63 (2H, d), 4.07 (3H, s), 2.83 (1H, t)

MP 145-147° C. .

EXAMPLE 128

2,3-Dichloro-N-{3-[(6-methoxy-3-pyridinyl)methoxy]-2-pyrazinyl}benzenesulphonamide

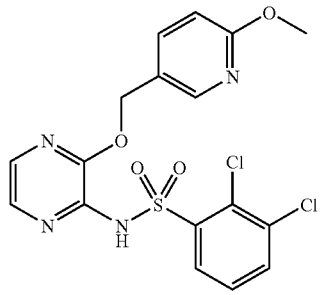

Prepared by the method of Example 28b using 2,3-dichloro-N-(3-chloro-2-pyrazinyl)benzenesulphonamide (Example 28a) (0.338 g) and (6-methoxy-3-pyridinyl)methanol (0.21 g). Yield 0.23 g.

m/e 439, 440 (M–1$^+$, 100%)

$^1$H NMR (CDCl$_3$) δ 8.28-8.26 (2H, m), 7.70-7.65 (3H, m), 7.60 (1H, br), 7.39 (1H, t), 6.80 (2H, d), 5.36 (2H, s), 3.97 (3H, s).

MP 187-188° C.

EXAMPLE 129

2,3-Dichloro-N-[6-chloro-3-methoxy-5-(methoxymethyl)-2-pyrazinyl]benzenesulphonamide

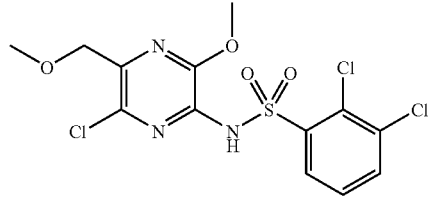

To a stirred solution of 2,3-dichloro-N-[6-chloro-5-(hydroxymethyl)-3-methoxy-2-pyrazinyl]benzenesulphonamide (Example 127) (0.1 g) in tetrahydrofuran (3 mL) was added manganese dioxide (0.131 g) and the resulting suspension was stirred for 20 h, filtered and concentrated. The residue was taken up into methanol (3 mL) and acetic acid (0.1 mL). To this solution was added ethylamine hydrochloride (0.081 g) and sodium cyanoborohydride (0.051 g). The resulting mixture was stirred for 20 h and concentrated onto silical gel (1 g) and eluting with methanol/dichloromethane mixtures to afford the titled compound (0.029 g) as a white solid.

m/e 412, 414 (M–1$^+$, 100%)

$^1$H NMR (CDCl$_3$) δ 8.35 (1H, dd), 7.72 (1H, d), 7.45 (1H, t), 4.45 (2H, s), 4.05 (3H, s), 3.43 (3H, s).

MP 193-196° C.

EXAMPLE 130

2-Chloro-N-(5-chloro-3-methoxy-2-pyrazinyl)-3-fluorobenzenesulphonamide a) N-(5-Chloro-3-methoxy-2-pyrazinyl)-3-fluorobenzenesulphonamide

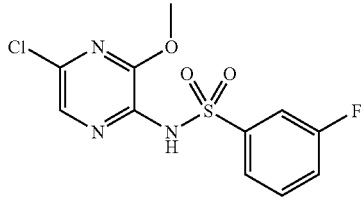

By the method outlined in Example 1 (reaction performed at room temperature) using 5-chloro-3-methoxy-2-pyrazinamine (0.798 g) and 3-fluorobenzenesulphonyl chloride (1.17 g). Yield 0.64 g.

m/e 316 (M–1$^+$, 100%)

b) 2-Chloro-N-(5-chloro-3-methoxy-2-pyrazinyl)-3-fluorobenzenesulphonamide

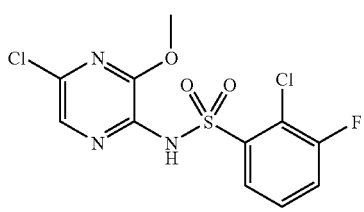

A solution of N-(5-chloro-3-methoxy-2-pyrazinyl)-3-fluorobenzenesulphonamide (Example 130a) (0.159 g) in dry tetrahydrofuran (3 mL) was added to a stirred solution of lithium di-iso-propylamide (prepared from di-iso-propylamine (0.151 g) and n-butyl lithium (2.5$\underline{M}$ in hexanes)) in tetrahydrofuran (7.0 mL) at –78° C. The resulting solution was stirred at –78° C. for 15 minutes and then hexachloroethane (0.472 g) in tetrahydrofuran (2 mL) was added and the mixture allowed to attain room temperature over a 5 hour period. The reaction was quenched by the addition of 1N hydrochloric acid (10 mL) and extracted into ethyl acetate (2×20 mL). The combined extracts were dried (MgSO$_4$), filtered and concentrated to afford an oil that was purified by chromatography on silica gel eluting with ethyl acetate/isohexane mixtures gave the titled compound (0.086 g) as a white solid.

m/e 350, 352 (M–1$^+$, 100%)

$^1$H NMR (CDCl$_3$) δ 8.16 (1H, dd), 7.81 (1H, br), 7.62 (1H, s), 7.48-7.37 (2H, m), 4.06 (3H, s)

MP 159-159.5° C.

EXAMPLE 131

2-Chloro-3-fluoro-N-(3-methoxy-2-pyrazinyl)benzenesulphonamide a) 3-Fluoro-N-(3-methoxy-2-pyrazinyl)benzenesulphonamide

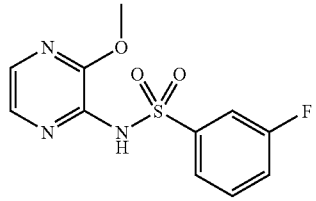

By the method outlined in Example 1 (reaction performed at room temperature) using 3-chloro-2-pyrazinamine (1.29 g), 3-fluorobenzenesulphonyl chloride (2.13 g). The crude adduct was reacted with a solution of sodium methoxide (10 mL of a 25% solution in methanol) in methanol (20 mL) to afford the sub-titled compound (2.36 g) as a solid.

m/e 284 (M+1$^+$, 100%)

MP 142-143° C.

b) 2-Chloro-3-fluoro-N-(3-methoxy-2-pyrazinyl)benzenesulphonamide

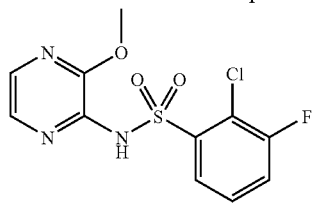

Prepared as for Example 130, 3-fluoro-N-(3-methoxy-2-pyrazinyl)benzenesulphonamide (Example 131a) (0.283 g), lithium di-iso-propylamide (prepared from di-iso-propylamine (0.30 g) and n-butyl lithium (0.96 mL of a 2.5$\underline{M}$ solution in hexanes)) and hexachloroethane (0.994 g) in anhydrous tetrahydrofuran (20 mL) afforded the titled compound (0.092 g) as a white solid after re-crystallisation from tert-butyl methylether.

m/e 318, 320 (M–1$^+$, 100%)

$^1$H NMR (CD$_3$OD) δ 8.11-8.08 (2H, m), 7.57 (1H, d), 7.57-7.50 (3H, m), 4.0 (3H, s).

MP 144-145° C.

EXAMPLE 132

2-Chloro-3-methoxy-N-(3-methoxy-2-pyrazinyl)benzenesulphonamide a) 3-Methoxy-N-(3-methoxy-2-pyrazinyl)benzenesulphonamide

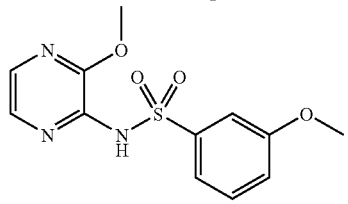

By the method outlined in Example 1 (reaction performed at room temperature) using 3-chloro-2-aminopyrazine (0.83 g), 3-methoxybenzenesulfonyl chloride (1.44 g). The crude adduct was reacted with a solution of sodium methoxide (10 mL of a 25% solution in methanol) in methanol (20 mL) to afford the sub-titled compound (1.41 g) as a solid.

m/e 296 (M+1$^+$, 100%)

MP 133-134° C.

b) 2-Chloro-3-methoxy-N-(3-methoxypyrazin-2-yl)benzenesulphonamide

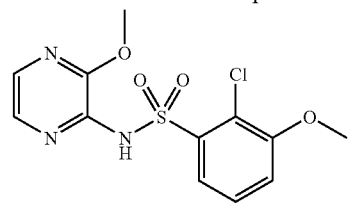

Prepared as for Example 130, 3-methoxy-N-(3-methoxy-2-pyrazinyl)benzenesulphonamide (Example 132a) (0.295 g), lithium di-iso-propylamide (prepared from di-iso-propylamine (0.30 g) and n-butyl lithium (0.96 mL of a 2.5$\underline{M}$ solution in hexanes)) and hexachloroethane (0.994 g) in anhydrous tetrahydrofuran (20 mL) afforded the titled compound (0.152 g) as a white solid after re-crystallisation from tert-butyl methylether.

m/e 328, 329 (M–1$^+$, 100%)

$^1$H NMR (CDCl$_3$) δ 7.97 (1H, d), 7.92 (1H, br), 7.65 (1H, d), 7.60 (1H, d), 7.41 (1H, t), 7.15 (1H, t), 3.99 (3H, s), 3.91 (3H, s).

MP 151-152° C.

EXAMPLE 133

N-[5-Bromo-3-[(2S)-2-pyrrolidinylmethoxy]-2-pyrazinyl]-2,3-dichlorobenzenesulphonamide

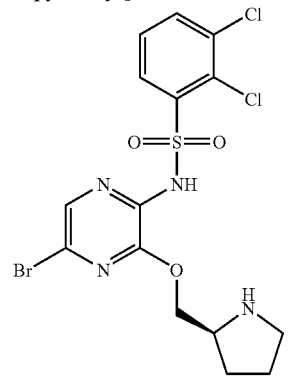

Sodium hydride (0.026 g of a 60% dispersion in oil) was added to a mixture of 2,3-dichloro-N-(3,5-dibromo-2-pyrazinyl)benzenesulphonamide (Example 31a) (0.1 g) and 2-hydroxymethylpyrrolidine-1-carboxylic acid tert-butyl ester (0.088 g) in 1,2-dimethoxyethane (2 mL). After 0.5 h, the reaction mixture was partitioned between 2N hydrochloric acid and ethyl acetate. The organic solution was dried (MgSO$_4$) and evaporated. Chromatography on silica gel eluting with ethyl acetate/iso-hexane mixtures gave the title compound protected with the BOC (tert-butoxycarbonyl) group (0.11 g) as an oil. This product was dissolved in dichloromethane (6 mL) and trifluoroacetic acid (2 mL). After 2 h, toluene was added and the solution evaporated to dryness. Crystallisation from diethyl ether gave the product as a white solid (0.083 g).

m/e 482 (M+1⁺, 100%)

¹H NMR (D6-DMSO) δ 8.99 (1H, br), 8.65 (1H, br s), 8.13 (1H,d), 7.95 (1H, d), 7.84.(1H, s), 7.59 (1H, t), 4.57(1H, dd), 4.39 (1H, t), 4.0 (1H, br s), 3.3 (2H, d), 2.20-2.05 (1H, m), 2.05-1.90 (2H, m), 1.85-1.75 (1H, m).

MP 199-200° C.

EXAMPLE 134

5-(2,3-Dichlorobenzenesulphonylamino)-6-(3-pyridinylmethoxy)pyrazine-2-carboxylic acid, methyl ester

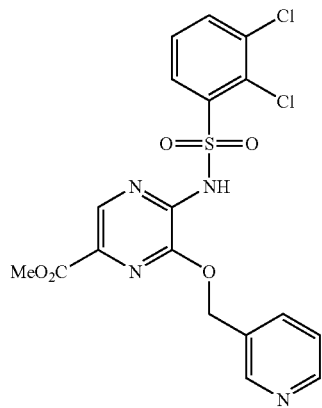

Prepared as for Example 113 using N-[5-bromo-3-(3-pyridinylmethoxy)-2-pyrazinyl]-2,3-dichlorobenzenesulphonamide (Example 34) (0.2 g) and bis(triphenylphosphine) palladium(II) dichloride (0.1 g). Yield 0.14 g.

m/e 469(M+1⁺, 100%)

¹H NMR (D6-DMSO) δ 8.83 (1H, s), 8.61 (1H, d), 8.15-8.05 (3H,m), 7.90 (1H, d), 7.60-7.50 (2H, m), 5.48 (2H, s), 3.82(3H, s).

MP 209-210° C.

EXAMPLE 135

5-{[(2,3-Dichlorophenyl)sulphonyl]amino}-6-(3-pyridinylmethoxy)-2-pyrazinecarboxamide

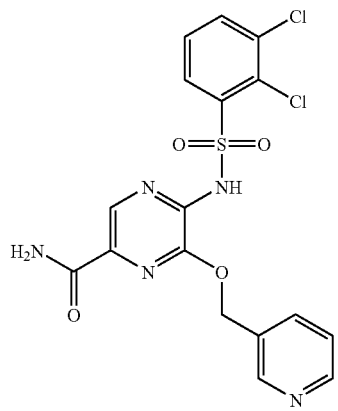

5-(2,3-Dichlorobenzenesulphonylamino)-6-(3-pyridinylmethoxy)pyrazine-2-carboxylic acid, methyl ester (Example 134) (0.05 g) was heated at 60° C. in 7M ammonia in methanol for 4 days. The solution was evaporated to dryness and the product crystallised from methyl acetate. Yield 0.027 g.

m/e 453(M−1⁺, 100%)

¹H NMR (D6-DMSO) δ 8.72 (1H, s), 8.52 (1H, d), 7.99 (1H,d), 7.90 (1H, d), 7.83 (1H, s), 7.66 (1H, d), 7.56 (1H, s), 7.45-7.35 (2H, m), 5.49 (2H, s).

MP 174-178° C.

EXAMPLE 136

2,3-Dichloro-N-[5-(4-pyridinyl)-3-(3-pyridinylmethoxy)-2-pyrazinyl]benzenesulphonaminde a) [5-Bromo-3-(3-pyridinylmethoxy)-2-pyrazinyl]
[(2,3-dichlorophenyl)sulphonyl]carbamic acid, 2-methylpropyl ester

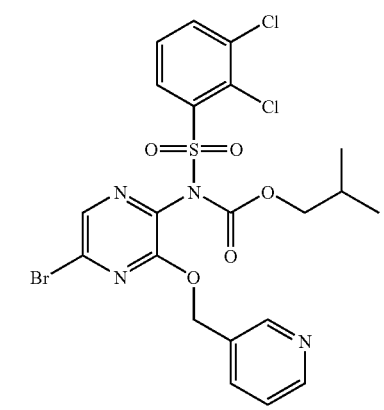

Sodium hydride (0.045 g of a 60% dispersion in oil) was added to N-[5-bromo-3-(3-pyridinylmethoxy)-2-pyrazinyl]-2,3-dichlorobenzenesulphonamide (Example 34) (0.5 g) in 1,2-dimethoxyethane (3 mL). Iso-butylchloroformate (0.15 mL) was added. After 2 h, the mixture was partitioned between water and ethyl acetate. The organic layer was dried (Na₂SO₄) and evaproated to yield the product (0.65 g). Used directly.

b) 2,3-Dichloro-N-[5-(4-pyridinyl)-3-(3-pyridinylmethoxy)-2-pyrazinyl]benzenesulphonamide

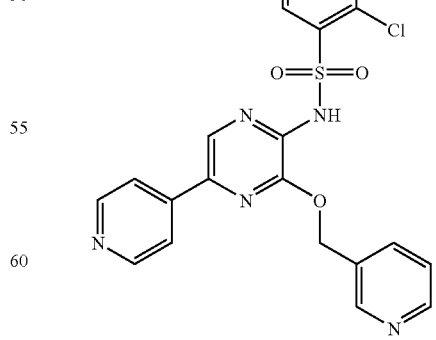

[5-Bromo-3-(3-pyridinylmethoxy)-2-pyrazinyl][(2,3-dichlorophenyl)sulphonyl]carbamic acid, 2-methylpropyl ester (Example 136a) (0.11 g), 4-tributylstannanylpyridine (0.067 g) and tetrakis(triphenylphosphine)palladium(0) (0.05 g) in toluene (3 mL) was heated at 95° C. for 16 h. Chromatography on silica gel eluting with ethyl acetate/ethanol mixtures gave the title compound protected with the 2-methylpropylcarbonyl group (0.09 g). The compound was heated at 60° C. in methanol (2 mL) and 1M sodium hydroxide (0.36 mL) for 1 h. The solution was evaporated. Purification was by reverse phase preparative high pressure liquid chromatography. Yield 0.015 g.

m/e 488(M+1$^+$, 100%)

$^1$H NMR (D6-DMSO) δ 9.05 (1H, s), 8.85 (2H, d), 8.78 (1H, d), 8.62 (1H, s), 8.44-8.39 (3H, m), 8.17 (1H, dd), 7.96 (1H,dd), 7.87-7.80 (1H, m), 7.64-7.57 (1H, m), 5.74 (2H, s)

MP 210° C. (dec.)

EXAMPLE 137

2,3-Dichloro-N-[5-(hydroxymethyl)-3-(3-pyridinylmethoxy)-2-pyrazinyl]benzenesulphonamide

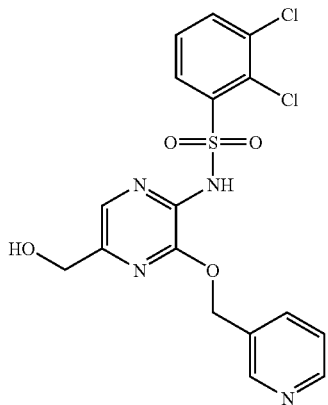

Lithium aluminium hydride (0.85 mL of a 1M solution in tetrahydrofuran) was added dropwise to 5-(2,3-dichlorobenzenesulphonylamino)-6-(3-pyridinylmethoxy)pyrazine-2-carboxylic acid, methyl ester (Example 134) (0.2 g) in tetrahydrofuran (10 mL) cooled to –65° C. The reaction mixture was allowed to warm to room temperature and stirred for 1h. Aqueous acetic acid was added and the mixture extracted with ethyl acetate. The organic solution was dried (MgSO$_4$) and evaporated. Chromatography on silica gel eluting with ethyl acetate/methanol mixtures gave the title compound (0.08 g).

m/e 441(M+1$^+$, 100%)

$^1$H NMR (D6-DMSO) δ 8.73 (1H, s), 8.55 (1H, d), 8.06 (1H, dd), 7.95-7.85 (2H, m), 7.65 (1H, s), 7.56 (1H, t), 7.64-7.57 (1H, m), 5.41 (2H, s), 5.36 (1H, t), 4.41 (2H, d)

EXAMPLE 138

2,3-Dichloro-N-[5-(hydroxymethyl)-3-methoxy)-2-pyrazinyl]benzenesulphonamide

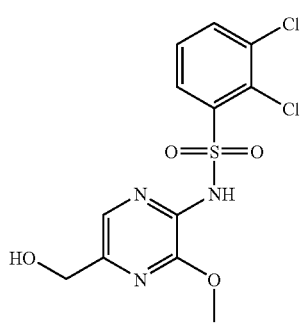

Prepared as for Example 120 using 5-(2,3-dichlorobenzenesuphonylamino)-6-methoxypyrazine-2-carboxylic acid, methyl ester (Example 113) (0.84 g). Yield 0.5 g.

m/e 364(M+1$^+$, 100%)

$^1$H NMR (D6-DMSO) δ 8.21 (1H, dd), 7.79 (1H, dd), 7.59 (1H, s), 7.51 (1H, t), 4.50 (2H, 5 s), 4.01 (3H, s).

MP 160-161° C.

EXAMPLE 139

N-(5-Allyloxy-3-methoxy-2-pyrazinyl)-2,3-dichlorobenzenesulphonamide

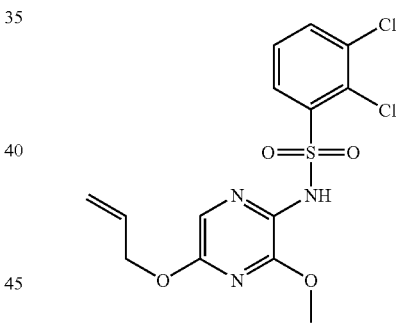

Procedure as for Example 115 using N-(5-chloro-3-methoxy-2-pyrazinyl)-2,3-dichloro-N-({2-[(trimethylsilyl)oxylethoxy}methyl)benzenesulphonamide (Example 115a) (0.25 g), allyl alcohol (0.06 g) and sodium hydride (0.035 g of a 60% dispersion in oil) in N,N-dimethylformamide (5 mL) stirred at room temperature for 5 days. Purification was by is silica gel chromatography eluting with ethyl acetate/iso-hexane mixtures to give the title compound with SEM attached. Yield 0.18 g. This compound was dissolved in dichloromethane (4 mL) and trifluoroacetic acid (1 mL). After 2 h, toluene was added and the mixture evaporated to dryness. Purification was by silica gel chromatography eluting with ethyl acetate/iso-hexane mixtures to give the tide compound. Crystallised for diethyl ether/iso-hexane mixtures. Yield 0.026 g.

m/e 390 (M+1$^+$, 100%)

$^1$H NMR (D6-DMSO) δ 10.81 (1H, s), 8.0-7.9 (2H, m), 7.53 (1H, t), 7.49 (1H, s), 6.07-7.02 (1H, m), 5.38 (1H, dd), 5.26 (1H, dd), 4.80 (2H, d), 3.82 (3H, s)

MP 120-121° C.

EXAMPLE 140

2,3-Dichloro-N-{3-methoxy-5-[(pyrazinyloxy)methyl]-2-pyrazinyl}benzenesulphonamide

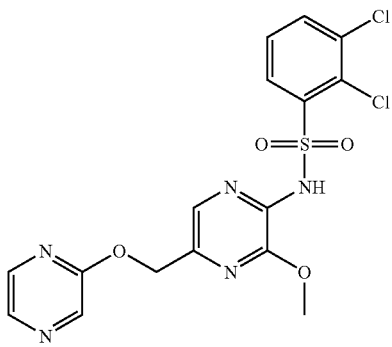

Sodium hydride (0.022 g of a 60% dispersion in oil) was added to 2,3-dichloro-N-[5-(hydroxymethyl)-3-methoxy-2-pyrazinyl]benzenesulphonamide (Example 138) (0.05 g) in N-methylpyrrolidinone (2 mL). After 0.5 h, chloropyrazine (0.013 mL) was added and the mixture heated at 60° C. for 3 h. Aqueous acetic acid was added and the mixture extracted with ethyl acetate. The organic solution was dried (Na$_2$SO$_4$) and evaporated. Chromatography on silica gel eluting with ethyl acetate/iso-hexane mixtures gave the title compound (0.012 g).

m/e 442(M+1$^+$, 100%)

$^1$H NMR (D6-DMSO) δ 8.36 (1H, s), 8.23 (2H, d), 8.06 (1H, d), 7.87 (1H, d), 7.68 (1H, s), 7.54 (1H, t), 5.26 (2H, s), 3.86 (3H, s).

MP 155° C. (dec).

EXAMPLE 141

2,3-Dichloro-N-[5-(3-hydroxy-1-propynyl)-3-methoxy-2-pyrazinyl]benzenesulphonamide

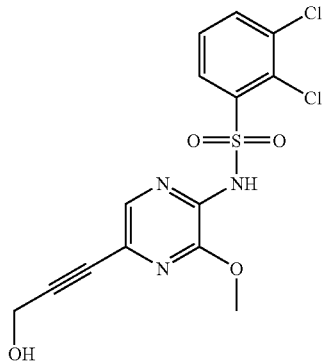

A mixture of N-(5-bromo-3-methoxy-2-pyrazinyl)-2,3-dichloro-N-[{2-(trimethylsilanyl)ethoxy}methyl]benzenesulphonamide (Example 55a) (0.52 g), propargyl alcohol (0.223 mL), copper(I)iodide (0.05 g) and bis(triphenylphosphine)palladium(II) chloride (0.1 g) in triethylamine (3 mL) was stirred at room temperature and under nitrogen for 16 h. The solvent was evaporated. Chromatography on silica gel eluting with ethyl acetate/iso-hexane mixtures gave the title compound containing the SEM ([2-(trimethylsilyl)ethoxy]methyl) protecting group (0.38 g). 0.074 g of this compound was dissolved in dichloromethane (2 mL) and trifluoroacetic acid (2 mL). After 1 h the solvent was evaporated. Chromatography on silica gel eluting with ethyl acetate/iso-hexane mixtures gave the title compound (0.043 g).

m/e 386(M−1$^+$, 100%)

$^1$H NMR (D6-DMSO) δ 8.07 (1H, d), 7.93 (1H, d), 7.72 (1H, s), 7.58 (1H, t), 4.29 (2H, s) 3.90 (3H, s).

EXAMPLE 142

N-{3-[(5-Bromo-3-pyridinyl)methoxy]-5-chloro-2-pyrazinyl}-2,3-dichlorobenzenesulphonamide

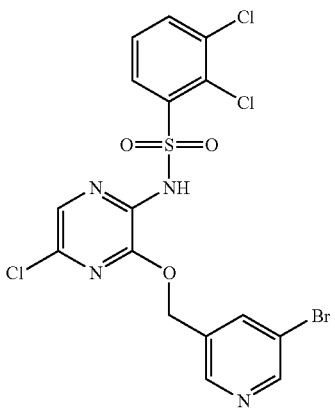

Prepared by the method of Example 31 using (5-bromo-3-pyridinyl)methanol (0.2 g) and 2,3-dichloro-N-(3,5-dichloro-2-pyrazinyl)benzenesulphonamide (Example 74) (0.25 g).

Yield 0.17 g.

m/e 523(M−1$^+$, 100%)

$^1$H NMR (D6-DMSO) δ 8.77 (1H, d), 8.71 (1H, d), 8.28 (1H, s), 8.07 (1H, dd), 7.92 (1H, d), 7.85 (1H, s), 7.55 (1H, t), 5.43 (2H, s). MP 199-201° C.

EXAMPLE 143

2,3-Dichloro-N-[5-chloro-3-{[6-(hydroxymethyl)-2-pyridinyl]methoxy}-2-pyrazinyl]benzenesulphonamide

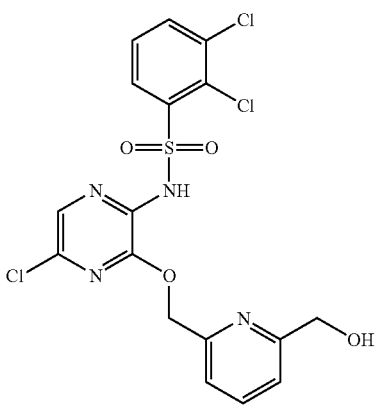

Prepared by the method of Example 31 using 2,6-bis(hydroxymethyl)pyridine (0.11 g) and 2,3-dichloro-N-(3,5- dichloro-2-pyrazinyl)benzenesulphonamide (Example 74) (0.11 g) in N-methylpyrrolidinone (2 mL). Yield 0.043 g.

m/e 475(M+1+, 100%)

$^1$H NMR (D6-DMSO) δ 7.97 (1H, d), 7.83 (1H, t), 7.68 (1H, d), 7.43-7.35 (4H, m), 5.44 (1H, s), 5.32 (2H, s), 4.58 (2H, s).

MP 220° C.

EXAMPLE 144

2,3-Dichloro-N-{5-chloro-3-[(2-methyl-4-oxazolyl)methoxy]-2-pyrazinyl}benzenesulphonamide

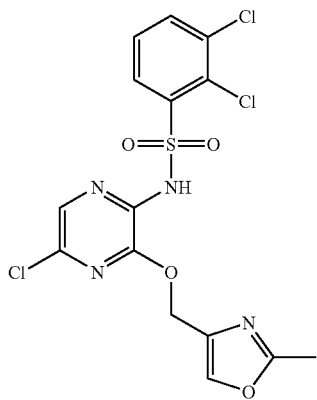

Prepared by the method of Example 31b using (2-methyl-4-oxazolyl)methanol (0.08 g) and 2,3-dichloro-N-(3,5-dichloro-2-pyrazinyl)benzenesulphonamide (Example 74) (0.26 g).

Yield 0.083 g.

m/e 449(M+1+, 100%)

$^1$H NMR (D6-DMSO) δ 8.09 (1H, s), 8.03 (1H, dd), 7.94 (1H, dd), 7.85 (1H, s), 7.55 (1H, t), 5.23 (2H, s), 2.45 (3H, s)

MP 172-173° C.

EXAMPLE 145

2,3-Dichloro-N-{3-[(2-methyl4-oxazolyl)methoxy]-2-pyrazinyl}benzenesulphonamide

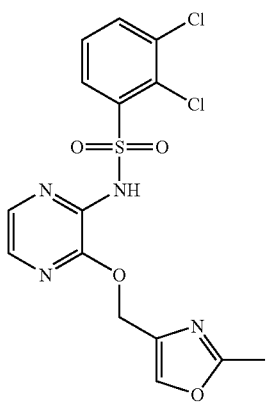

Prepared by the method of Example 28 using (2-methyl-4-oxazolyl)methanol (0.3 g) and 2,3-dichloro-N-(3-chloro-2-pyrazinyl)benzenesulphonamide (0.89 g). Yield 0.035 g.

m/e412(M-1+, 100%)

$^1$H NMR (D6-DMSO) δ 8.06 (2H, dd), 7.92 (1H, dd), 7.85 (1H, br s), 7.70 (1H, br s), 7.56 (1H, t), 5.23 (2H, s), 2.41 (3H, s).

MP 207-209° C.

Examples 146-165 were prepared using the following procedure To a solution of N-(3,5-dibromo-2-pyrazinyl)-2,3-dichlorobenzenesulphonamide (Example 31) (0.003 g) and primary alcohol (0.026 mL of a 0.5M solution in N-methylpyrrolidinone) in N-methylpyrrolidinone (0.1 mL) was added potassium tert-butoxide (0.050 mL of a 1M solution in tetrahydrofuran). The solution was allowed to stand for 24 hours. The reaction mixture was diluted with acetic acid (0.010 mL) and water (0.10 mL) and the solvents were evaporated. The residue was redissolved in dimethylsulphoxide (0.5 mL) and purified by mass directed high pressure liquid chromatography. The solvent was evaporated to afford a solid.

EXAMPLE 146

N-[5-Bromo-3-(phenylmethoxy)-2-pyrazinyl]-2,3-dichlorobenzenesulphonamide

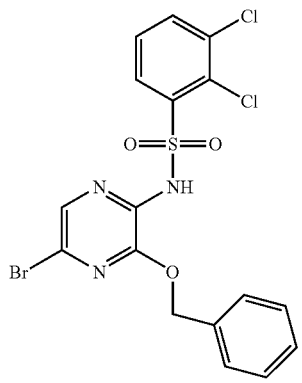

m/e 489(M+1+, 100%)

EXAMPLE 147

N-[5-Bromo-3-(2-cyclopropylethoxy)pyrazinyl]-2,3-dichlorobenzenesulphonamide

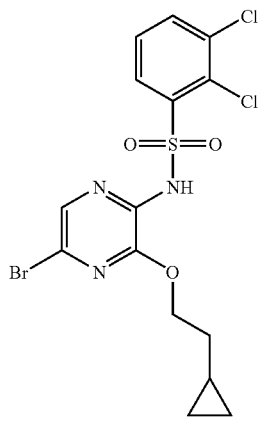

m/e 467(M+1+, 100%)

EXAMPLE 148

N-[5-Bromo-3-(3-thienylmethoxy)pyrazinyl]-2,3-dichlorobenzenesulphonamde

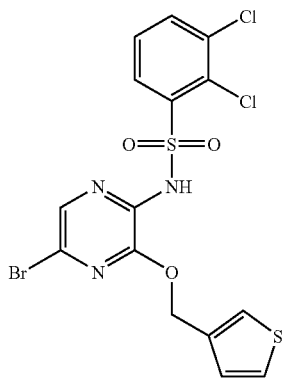

m/e 495(M+1$^+$, 100%)

EXAMPLE 149

N-{5-Bromo-3-[(2-methyl-3-furanyl)methoxy]-2-pyrazinyl}-2,3-dichlorobenzenesulphonamide

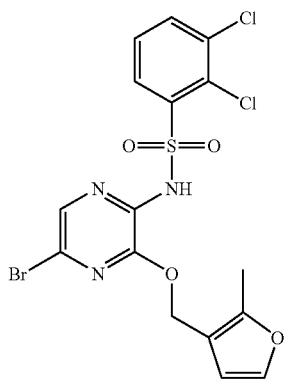

m/e 493(M+1$^+$, 100%)

EXAMPLE 150

N-{5-Bromo-3-[(3-furanyl)methoxy]-2-pyrazinyl}-2,3-dichlorobenzenesulphonamide

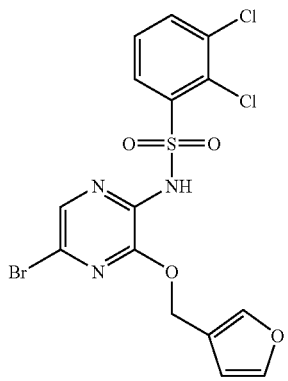

m/e 479(M+1$^+$, 100%)

EXAMPLE 151

N-{5-Bromo-3-[(4-fluorophenyl)methoxy]-2-pyrazinyl}-2,3-dichlorobenzenesulphonamide

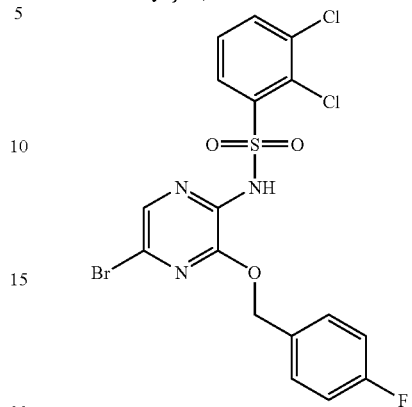

m/e 507(M+1$^+$, 100%)

EXAMPLE 152

N-{5-Bromo-3-[(3-fluorophenyl)methoxy]-2-pyrazinyl}-2,3-dichlorobenzenesulphonamide

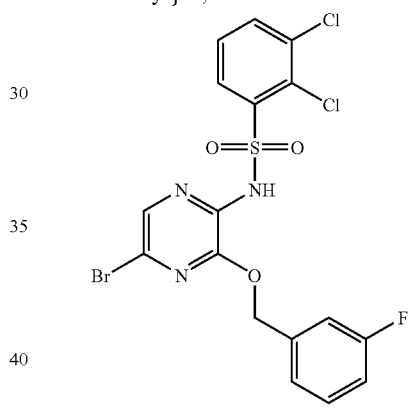

m/e 507(M+1$^+$, 100%)

EXAMPLE 153

N-{5-Bromo-3-[3-(2-pyridinyl)propoxy]-2-pyrazinyl}-2,3-dichlorobenzenesulphonamide

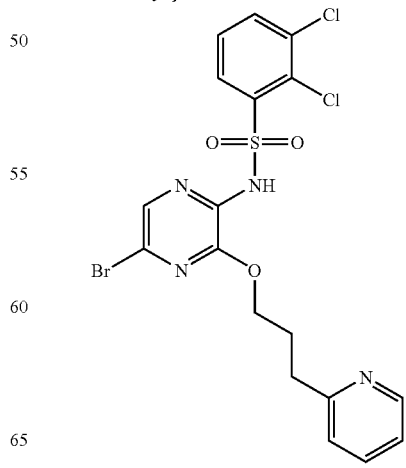

m/e 518(M+1$^+$, 100%)

EXAMPLE 154

N-[5-Bromo-3-(pentyloxy)-2-pyrazinyl]-2,3-dichlorobenzenesulphonamide

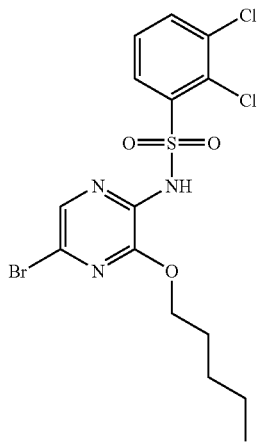

m/e 469(M+1$^+$, 100%)

EXAMPLE 155

N-[5-Bromo-3-(propyloxy)-2-pyrazinyl]-2,3-dichlorobenzenesulphonamide

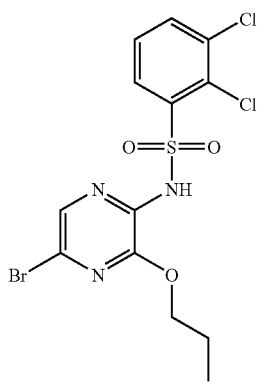

m/e 441(M+1$^+$, 100%)

EXAMPLE 156

N-[5-Bromo-3-(2-methoxyethoxy)-2-pyrazinyl]-2,3-dichlorobenzenesulphonamide

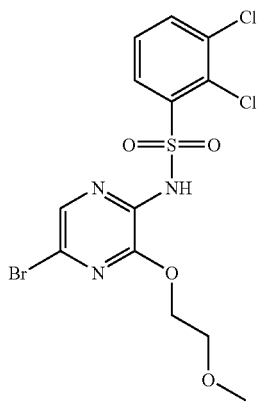

m/e 457(M+1$^+$, 100%)

EXAMPLE 157

N-[5-Bromo-3-(2-ethoxyethoxy)-2-pyrazinyl]-2,3-dichlorobenzenesulphonamide

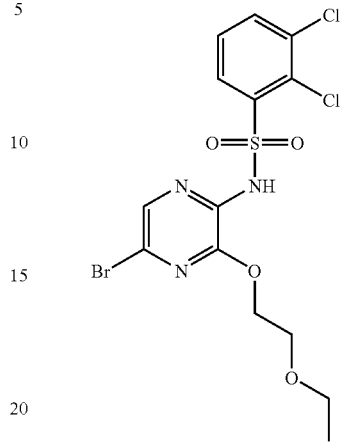

m/e 471(M+1$^+$, 100%)

EXAMPLE 158

N-[5-Bromo-3-(2-fluoroethoxy)-2-pyrazinyl]-2,3-dichlorobenzenesulphonamide

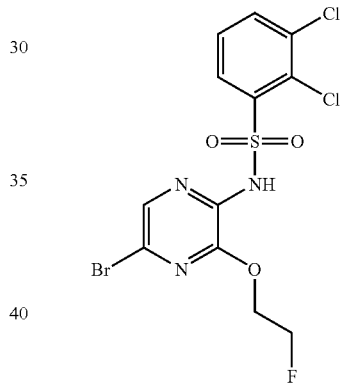

m/e 445(M+1$^+$, 100%)

EXAMPLE 159

N-{5-Bromo-3-[2-(1H-imidazol-1-yl)ethoxy]-2-pyrazinyl}-2,3-dichlorobenzenesulphonamide

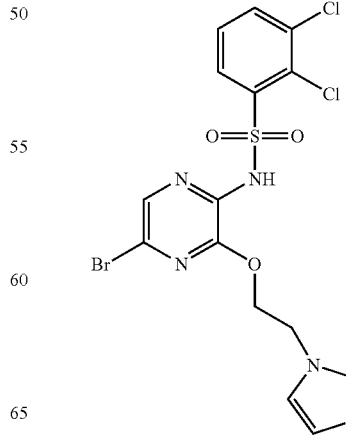

m/e 493(M+1$^+$, 100%)

EXAMPLE 160

N-{5-Bromo-3-[3-(3-pyridinyl)propoxy]-2-pyrazinyl}-2,3-dichlorobenzenesulphonamide

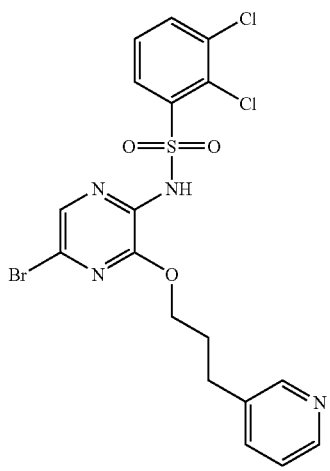

m/e 516(M−1⁺, 100%)

EXAMPLE 161

N-[5-Bromo-3-[2-(methylamino)ethoxy]-2-pyrazinyl]-2,3-dichlorobenzenesulphonamide

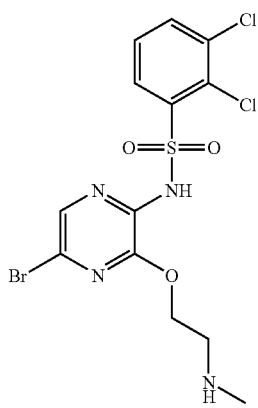

m/e 456(M+1⁺, 100%)

EXAMPLE 162

N-{5-Bromo-3-[3-(4-hydroxyphenyl)propoxy]-2-pyrazinyl}-2,3-dichlorobenzenesulphonamide

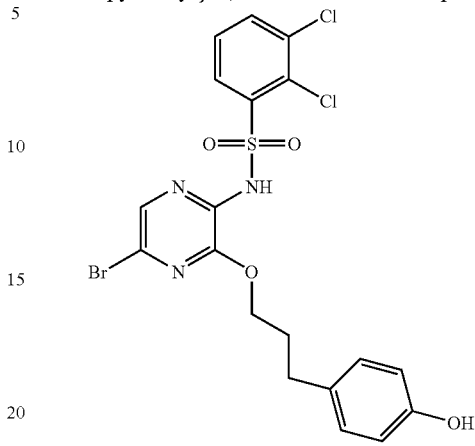

m/e 533(M+1⁺, 100%)

EXAMPLE 163

N-[5-Bromo-3-(2-phenoxyethoxy)-2-pyrazinyl]-2,3-dichlorobenzenesulphonamide

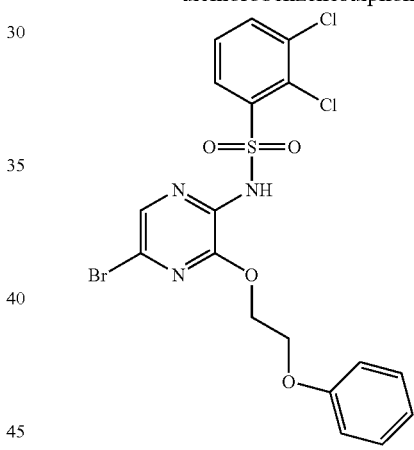

m/e 517(M−1⁺, 100%)

EXAMPLE 164

N-[5-Bromo-3-(cyclopropylmethoxy)-2-pyrazinyl]-2,3-dichlorobenzenesulphonamide

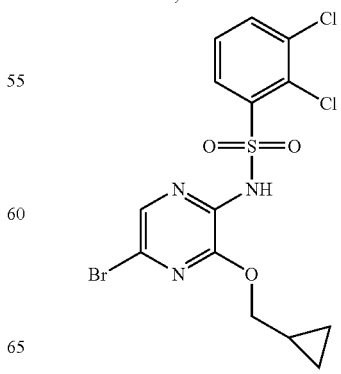

m/e 453(M+1⁺, 100%)

EXAMPLE 165

N-[5-Bromo-3-(3-phenoxypropoxy)-2-pyrazinyl]-2,3-dichlorobenzenesulphonamide

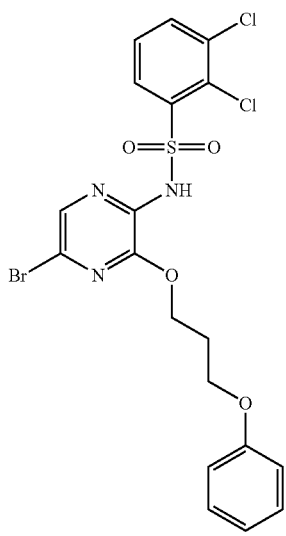

m/e 531(M−1+, 100%)

EXAMPLE 166

2,3-Dichloro-N-(5-ethoxy-3-methoxy-2-pyrazinyl)benzenesulphonamide

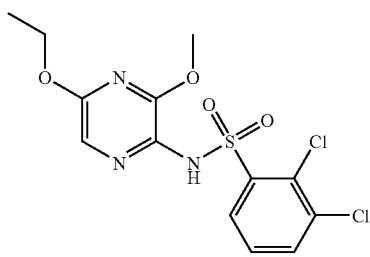

Prepared as for Example 56 using N-(5-bromo-3-methoxy-2-pyrazinyl)-2,3-dichloro-N-[{2-(trimethylsilanyl)ethoxy}methyl]benzenesulphonamide (Example 55a) (0.3 g) and sodium ethoxide (5 mL of a 0.5M solution in ethanol). Yield 0.1 g.

m/e 378 (M+1,100%)

$^1$H NMR (CDCl$_3$) δ 8.22 (1H, d), 7.65 (1H, d), 7.49 (1H, s), 7.34 (1H, t), 7.30 (1H, s), 4.24 (2H, q), 3.95 (3H, s), 1.36 (3H, t)

MP 96-97° C.

EXAMPLE 167

2,3-Dichloro-N-[3-methoxy-5-([1,2,4]-1-triazolyl)-2-pyrazinyl]benzenesulphonamide

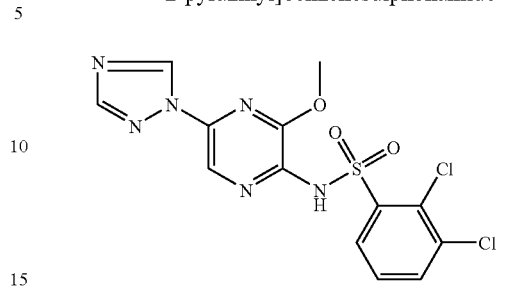

Prepared as for Example 101b (reaction heated at 50° C.) using N-(5-bromo-3-methoxy-2-pyrazinyl)-2,3-dichloro-N-[{2-(trimethylsilanyl)ethoxy}methyl]benzenesulphonamide (Example 55a) (0.25 g) and [1,2,4]triazole (0.1 g). The intermediate product containing the SEM (2-[trimethylsilyl]ethoxymethyl) group was purified by silica gel chromatography eluting with ethyl acetate/iso-hexane mixtures. Deprotection as for Example 101b gave the title compound. Yield 0.035 g.

m/e 401 (M+1+, 100%)

$^1$H NMR (CDCl$_3$) δ 8.92 (1H .s), 8.34 (1H, d), 8.24 (1H, s), 8.08 (1H, s), 8.01 (1H, br s), 7.72 (1H, d), 7.43 (1H, t), 4.14 (3H, t)

MP 248-249° C.

EXAMPLE 168

2-[5-(2,3-Dichlorobenzenesulphonylamino)-6methoxy-2-pyrazinylsulphanyl]-N-methylacetamide

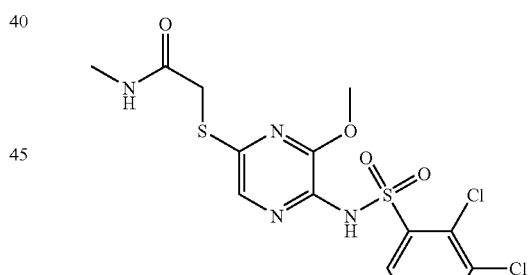

Prepared as for Example 101b using N-(5-bromo-3-methoxy-2-pyrazinyl)-2,3-dichloro-N-[{2-(trimethylsilanyl)ethoxy}methyl]benzenesulphonamide (Example 55a) (0.4 g) and 2-mercapto-N-methylacetamide (0.1 g). The intermediate product containing the SEM (2-[trimethylsilyl]ethoxymethyl) group was purified by silica gel chromatography eluting with ethyl acetate/iso-hexane mixtures. Deprotection as for Example 101b gave the title compound. Yield 0.05 g.

m/e 437 (M+1+, 100%)

$^1$H NMR (CDCl$_3$) δ 8.25 (1H, dd), 7.76 (1H, s), 7.68 (1H, dd), 7.58 (1H, s), 7.40 (1H, t), 6.62 (1H, br s), 3.99 (3H, s), 3.69 (2H, s), 2.86 (3H, d)

MP 150-152° C.

EXAMPLE 169

2-[5-(2,3-Dichlorobenzenesulphonylamino)-6-methoxy-2-pyrazinylsulphanyl]acetamide

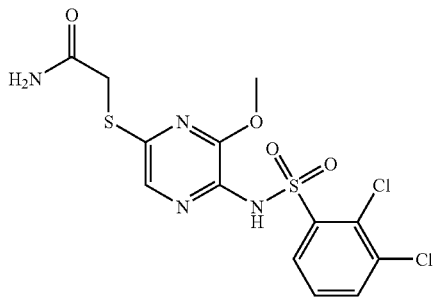

Prepared as for Example 101b using N-(5-bromo-3-methoxy-2-pyrazinyl)-2,3-dichloro-N-[{2-(trimethylsilanyl)ethoxy}methyl]benzenesulphonamide (Example 55a) (0.2 g) and 2-mercaptoacetamide (0.05 g). The intermediate product containing the SEM group was purified by silica gel chromatography eluting with ethyl acetate/iso-hexane mixtures. Deprotection as for Example 101b gave the title compound. Yield 0.03 g.

m/e 423 (M+1$^+$, 100%)

$^1$H NMR (CDCl$_3$) δ 7.98 (1H, dd), 7.75 (1H, d), 7.46-7.42 (3H, m), 7.06 (1H, s), 3.83 (3H, s), 2.59 (2H, s)

MP 163-164° C.

EXAMPLE 170

2,3-Dichloro-N-[5-(4-fluorobenzylsulphanyl)-3-methoxy-2-pyrazinyl]benzenesulphonamide

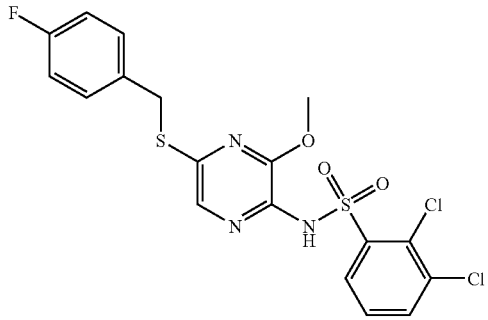

Prepared as for Example 101b using N-(5-bromo-3-methoxy-2-pyrazinyl)-2,3-dichloro-N-{[2-(trimethylsilanyl)ethoxy]methyl}benzenesulphonamide (Example 55a) (0.4 g) and (4-fluorophenyl)methanethiol (0.13 g). The intermediate product containing the SEM group was purified by silica gel chromatography eluting with ethyl acetate/iso-hexane mixtures. Deprotection as for Example 101b gave the title compound. Yield 0.2 g m/e 474 (M+1$^+$, 100%)

$^1$H NMR (CDCl$_3$) δ 8.25 (1H, dd), 7.73 (1H, s), 7.67 (1H, dd), 7.51 (1H, s), 7.38 (1H, t), 7.27 (2H, m), 6.92 (2H, m), 4.24 (2H, s), 4.01 (3H, s)

MP 119-120° C.

EXAMPLE 171

2,3-Dichloro-N-[5-cyanomethylsulphanyl-3-methoxy-2-pyrazinyl]benzenesulphonamide

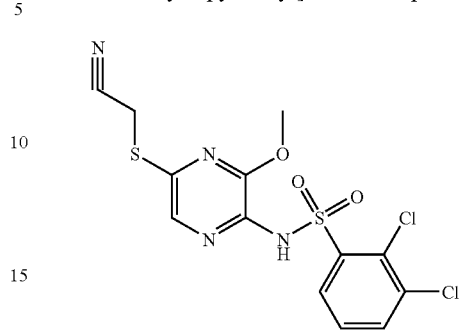

See example 172 for preparation.

m/e 403 (M-1$^+$, 100%)

$^1$H NMR (CDCl$_3$) δ 8.28 (1H, dd), 7.84 (1H, s), 7.69 (1H, dd), 7.63 (1H, s), 7.38 (1H, t), 4.11 (3H, s), 3.78 (2H, s)

MP 158-159° C.

EXAMPLE 172

2,3-Dichloro-N-[3-methoxy-5-([1,2,4]-3-oxadiazolylmethylsulphanyl)-2-pyrazinyl]benzenesulphonamide

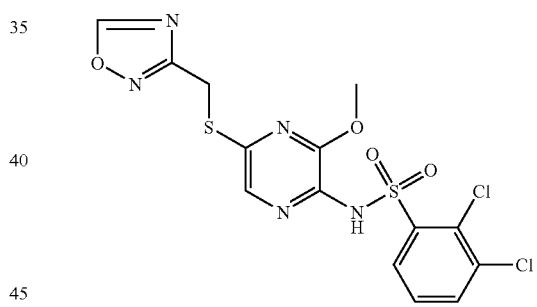

Prepared as for Example 101b using N-(5-bromo-3-methoxy-2-pyrazinyl)-2,3-dichloro-N-[{2-(trimethylsilanyl)ethoxy}methyl]benzenesulphonamide (Example 55a) (0.4 g), [1,2,4]-3-oxadiazolylmethanethiol (0.15 g) and cesium carbonate (0.5 g) at room temperature for 16 h. The intermediate products containing the SEM (2-[trimethylsilyl]ethoxymethyl) group was purified by silica gel chromatography eluting with ethyl acetate/iso-hexane mixtures. Deprotection as for Example 101b gave the title compound (0.09 g) and 2,3-dichloro-N-[5-cyanomethylsulphanyl-3-methoxy-2-pyrazinyl]benzenesulphonamide (Example 171) (0.1 g) which were separated by silica gel chromatography eluting with dichloromethane.

m/e 448 (M+1$^+$, 100%)

$^1$H NMR (CDCl$_3$) δ 8.64 (1H, s), 8.26 (1H, dd), 7.76 (1H, s), 7.67 (1H, dd), 7.57 (1H, s), 7.37 (1H, t), 4.39 (2H, s), 4.04 (3H, s)

MP 154-156° C.

EXAMPLE 173

N-[5-(2-Aminoethylsulphanyl)-3-methoxy-2-pyrazinyl]-2,3-dichlorobenzenesulphonamide

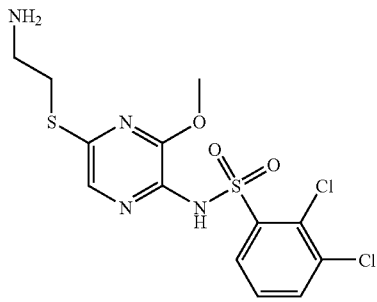

Prepared as for Example 101b using N-(5-bromo-3-methoxy-2-pyrazinyl)-2,3-dichloro-N-[{2-(trimethylsilanyl)ethoxy}methyl]benzenesulphonamide (Example 55a) (0.45 g) and 2-amninoethanethiol hydrochloride (0.2 g). Yield 0.03 g m/e 409 (M+1$^+$, 100%)

$^1$H NMR (D6-DMSO) δ 8.02 (1H, dd), 7.94 (1H, dd), 7.87 (1H, s), 7.70 (1H, s), 7.58 (1H, t), 3.93 (3H, s), 3.48 (2H, br s), 3.28 (2H, t), 3.10-3.03 (2H, m)

MP 189-190° C.

EXAMPLE 174

2,3-Dichloro-N-[3-methoxy-5-(5-methyl-3-isoxazolylmethoxy))-2-pyrazinyl]benzenesulphonamide

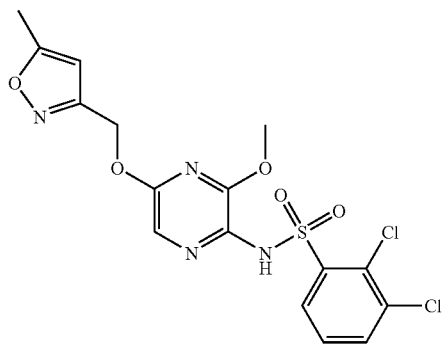

Prepared as for Example 115b using N-(5-bromo-3-methoxy-2-pyrazinyl)-2,3-dichloro-N-[{2-(trimethylsilanyl)ethoxy}methyl]benzenesulphonamide (Example 55a) (0.3 g) and (5-methyl-3-oxazolyl)methanol (0.13 g). The intermediate product containing the SEM (2-[trimethylsilyl]ethoxymethyl) group was purified by silica gel chromatography eluting with ethyl acetate/iso-hexane mixtures. Deprotection as for Example 115b gave the title compound. Yield 0.2 g m/e 445 (M+1$^+$, 100%)

$^1$H NMR (CDCl$_3$) δ 8.22 (1H, dd), 7.66 (1H, dd), 7.59 (1H, s), 7.38 (2H, t), 6.01 (1H, t), 5.31 (2H, s), 3.97 (3H, s), 2.43 (3H, s)

MP 142-143° C.

EXAMPLE 175

2,3-Dichloro-N-[5-(5-dimethylaminomethyl-2-furanylmethoxy)-3-methoxy-2-pyrazinyl]benzenesulphonamide

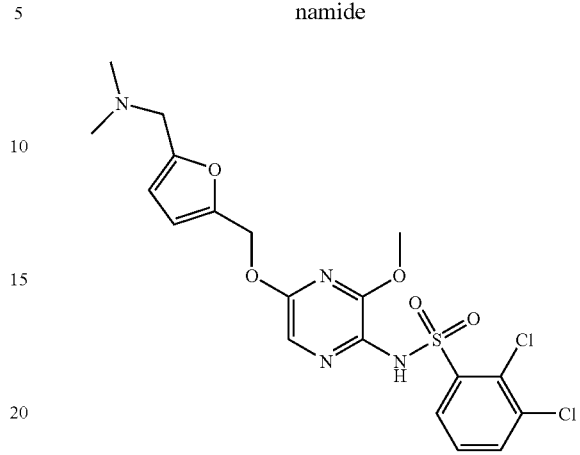

Prepared as for Example 115b using N-(5-bromo-3-methoxy-2-pyrazinyl)-2,3-dichloro-N-[{2-(trimethylsilanyl)ethoxy}methyl]benzenesulphonamide (Example 55a) (0.3 g) and (5-dimethylaminomethyl-2-furanyl)methanol (0.2 g). After removal of the SEM (2-[trimethylsilyl]ethoxymethyl) group the title compound was purified by silica gel chromatography eluting with methanol/dichloromethane mixtures Yield 0.23 g m/e 487 (M+1$^+$, 100%)

$^1$H NMR (CDCl$_3$) δ 8.21 (1H, dd), 7.66 (1H, dd), 7.37 (2H. t), 6.39 (2H, s), 5.20 (2H, s), 4.00 (3H, s), 3.84 (2H, s), 2.51 (6H, s)

MP 114-115° C.

EXAMPLE 176

N-[5-Bromo-3-(5-dimethylaminomethyl-2-furanylmethoxy)-2-pyrazinyl]-2,3-dichloro-benzenesulphonamide

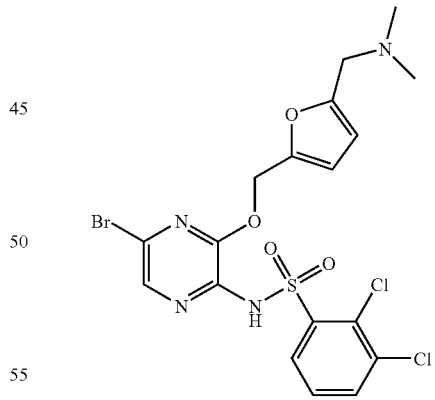

Prepared by the method of Example 31 using (5-dimethylaminomethyl-2-furanyl)methanol (0.2 g) and 2,3-dichloro-N-(3,5-dibromo-2-pyrazinyl)benzenesulphonamide (Example 31a) (0.2 g). Purified by silica gel chromatography eluting with methanol/dichloromethane mixtures and recrystallised from acetonitrile. Yield 0.058 g.

m/e 535 (M+1$^+$, 100%)

$^1$H NMR (D6-DMSO) δ 7.92 (1H, dd), 7.63 (1H, dd), 7.36 (2H, t), 6.71 (1H, d), 6.68 (1H, d), 5.22 (2H, s), 4.37 (2H, d), 2.75 (6H, s)

MP 206-207° C.

EXAMPLE 177

2,3-Dichloro-N-[5-(2-hydroxyethylsulphanyl)-3-methoxy-2-pyrazinyl]benzenesulphonamide

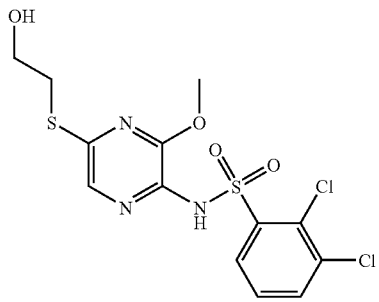

Prepared as for Example 101b using N-(5-bromo-3-methoxy-2-pyrazinyl)-2,3-dichloro-N-[{2-(trimethylsilanyl)ethoxy}methyl]benzenesulphonamide (Example 55a) (0.2 g) and 2-mercaptoethanol (0.2 g). After removal of the SEM (2-[trimethylsilyl]ethoxymethyl) group the title compound was purified by silica gel chromatography eluting with methanol/dichloromethane mixtures. Yield 0.015 g m/e 410 (M+1$^+$, 100%)

$^1$H NMR (CDCl$_3$) δ 8.27 (1H, dd), 7.78 (1H, s), 7.67 (1H, dd), 7.61 (1H, s), 7.39 (1H. t), 4.04 (3H, s), 3.83 (2H, t), 3.24 (2H, t)

MP 180-181° C.

EXAMPLE 178

2,3-Dichloro-N-{5-[2-(ethylureido)ethylsulphanyl]-3-methoxy-2-pyrazinyl}benzenesulphonamide

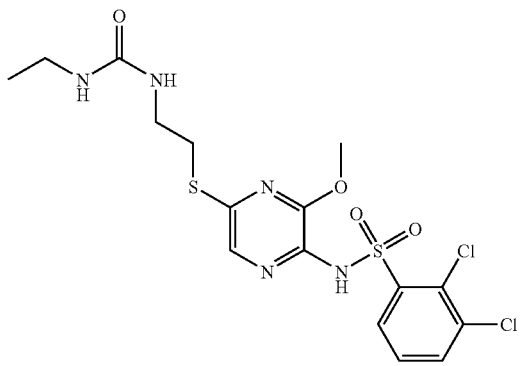

Ethylisocyanate (0.016 g) was added to N-[5-(2-aminoethylsulphanyl)-3-methoxy-2-pyrazinyl]-2,3-dichloro-benzenesulphonamide (Example 173) (0.08 g) in dichloromethane (5 mL). After 1 h, the reaction mixture was evaporated to dryness. Purified by silica gel chromatography eluting with methanol/dichloromethane mixtures. Yield 0.015 g.

m/e 480(M+1$^+$, 100%)

$^1$H NMR (CDCl$_3$) δ 8.27 (1H, dd), 7.69 (1H, dd), 7.56 (1H, s), 7.39 (1H, t), 4.60 (1H, br s), 4.18 (1H, br s), 4.04 (3H, s), 3.40-3.30 (2H, m), 3.30-3.2 (2H, m), 3.25-3.20 (2H, m), 1.15 (3H, t)

EXAMPLE 179

2,3-Dichloro-N-[3-(5-dimethylaminomethyl-2-furanylmethoxy)-2-pyrazinyl]benzenesulphonamide

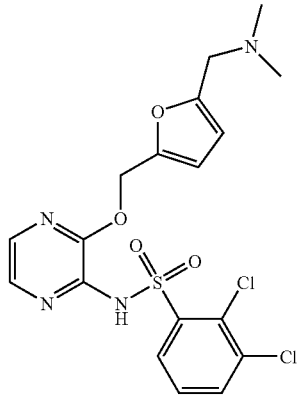

Prepared by the method of Example 28 using (5-dimethylaminomethyl-2-furanyl)methanol (0.2 g) and 2,3-dichloro-N-(3-chloro-2-pyrazinyl)benzenesulphonamide (Example 28) (0.4 g). Purified by silica gel chromatography eluting with methanol/dichloromethane mixtures. Yield 0.2 g.

m/e 455 (M–1$^+$, 100%)

$^1$H NMR (D6-DMSO) δ 7.96 (1H, dd), 7.66 (1H, dd), 7.40 (1H, t), 7.30 (1H, d), 7.24 (1H, d), 6.65 (1H, s), 6.64 (1H, d), 5.23 (2H, s), 4.25 (2H, s), 2.66 (6H, s)

EXAMPLE 180

2,3-Dichloro-N-[6-chloro-3-(5-dimethylaminomethyl-2-furanylmethoxy)-2-pyrazinyl]benzenesulphonamide

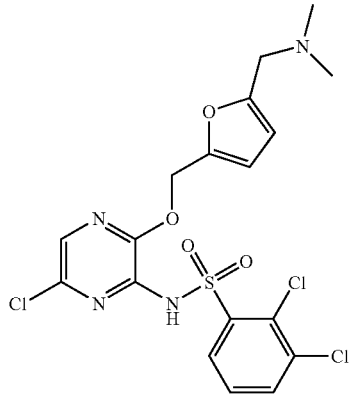

Prepared by the method of Example 31 using (5-dimethylaminomethyl-2-furanyl)methanol (0.2 g) and N-(3-bromo-6-chloro-2-pyrazinyl)-2,3-dichlorobenzenesulphonamide (Example 98) (0.3 g). Purified by silica gel chromatography eluting with methanol/dichloromethane mixtures. Yield 0.11 g.

m/e 491 (M+1$^+$, 100%)

$^1$H NMR (D6-DMSO) δ 8.01 (1H, dd), 7.66 (1H, dd), 7.39 (1H, t), 7.11 (1H, s), 6.69 (1H, d), 6.67 (1H, d), 5.20 (2H, s), 4.39 (2H, s), 2.76 (6H, s)

MP 209-210° C.

EXAMPLE 181

2,3-Dichloro-N-[6-chloro-3-(5-methylaminomethyl-2-furanylmethoxy)-2-pyrazinyl]benzenesulphonamide

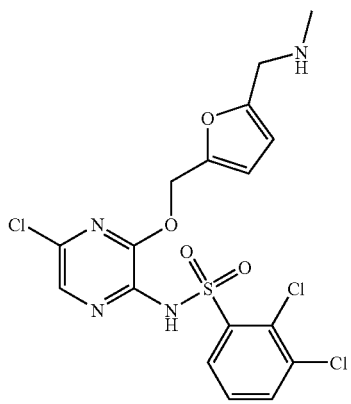

Prepared by the method of Example 31 using (5-methylaminomethyl-2-furanyl)methanol (0.3 g) and 2,3-dichloro-N-(3,5-dichloro-2-pyrazinyl)benzenesulphonamide (Example 74) (0.4 g). Purified by silica gel chromatography eluting with methanol/dichloromethane mixtures. Yield 0.03 g.

m/e 477 (M+1$^+$, 100%)

$^1$H NMR (D6-DMSO) δ 8.98 (2H, br), 7.92 (1H, d), 7.63 (1H, d), 7.35 (1H, t), 7.29 (1H, s), 6.67 (1H, d), 6.64 (1H, d), 5.20 (2H, s), 4.25 (2H, s), 2.59 (3H, s)

MP 211-212° C.

EXAMPLE 182

2,3-Dichloro-N-[5-chloro-3-(5-dimethylaninomethyl-2-furanylmethoxy)-2-pyrazinyl]benzenesulphonamide

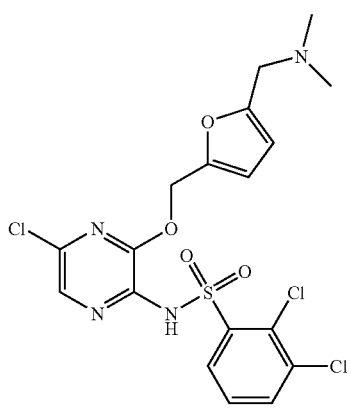

Prepared by the method of Example 31 using (5-dimethylaminomethyl-2-furanyl)methanol (0.3 g) and 2,3-dichloro-N-(3,5-dichloro-2-pyrazinyl)benzenesulphonamide (Example 74) (0.4 g). Purified by silica gel chromatography eluting with methanol/dichloromethane mixtures. Yield 0.30 g.

m/e 491 (M+1$^+$, 100%)

$^1$H NMR (D6-DMSO) δ 7.93 (1H, dd), 7.65 (1H, dd), 7.36 (1H, t), 7.32 (1H, s), 6.71 (1H, d), 6.69 (1H, d), 5.23 (2H, s), 4.38 (2H, s), 2.75 (6H, s)

MP 209-210° C.

EXAMPLE 183

2,3-Dichloro-N-[3-(5-methylaminomethyl-2-furanylmethoxy)-2-pyrazinyl]benzenesulphonamide

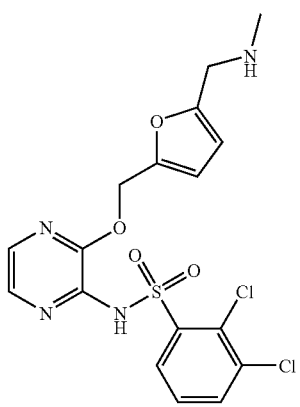

Prepared by the method of Example 28 using (5-methylaminomethyl-2-furanyl)methanol (0.2 g) and 2,3-dichloro-N-(3-chloro-2-pyrazinyl)benzenesulphonamide (Example 28) (0.4 g). Purified by silica gel chromatography eluting with methanol/dichloromethane mixtures. Yield 0.12 g.

m/e 443 (M+1$^+$, 100%)

$^1$H NMR (D6-DMSO) δ 8.99 (2H, br s), 7.95 (1H, d), 7.62 (1H, d), 7.35 (1H, t), 7.24 (1H, d), 7.15 (1H, d), 6,88 (1H, d), 6.63 (1H, d), 5.20 (2H, s), 4.24 (2H, s), 2.58 (3H, s)

MP 198-199° C.

EXAMPLE 184

N-(5-Bromo-3-methoxypyrazinyl)-2-cyanobenzenesulphonamide

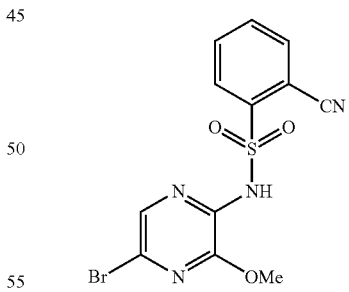

Prepared by the method of Example 1 (reaction performed at room temperature) using 5-bromo-3-methoxy-2-pyrazinamine (0.2 g) and 2-cyanobenzenesulphonyl chloride (0.24 g).

Yield 0.059 g.

m/e 369/370 (M+1$^+$), 307/309 (100%)

$^1$H NMR (D6-DMSO) δ 8.14 (1H, d), 8.09 (1H, d), 7.93-7.82 (3H, m), 3.93 (3H, s).

MP 190-191.5° C.

EXAMPLE 185

N-(5-Bromo-3-methoxypyrazinyl)-2,3-dichloro-4-fluorobenzenesulphonamide a) 2,3-Dichloro-4-fluorobenzenesulphonyl chloride

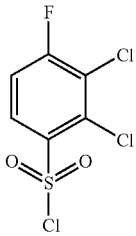

Chlorosulphonic acid (12.1 mL) was added dropwise to a solution of 2,3-dichloro-4-fluorobenzene (5.0 g) in dichloromethane (12 mL) at −40° C. The solution was allowed to slowly warm to room temperature and was stirred for 3 days. The solution was poured onto crushed ice/water, extracted into dichloromethane and concentrated under reduced pressure. Purified by silica gel chromatography eluting with dichloromethane/iso-hexane mixtures. Yield 4.2 g m/e 262/264 (M$^+$), 163 (100%).

b) N-(5-Bromo-3-methoxypyrazinyl)-2,3-dichloro-4-fluorobenzenesulphonamide

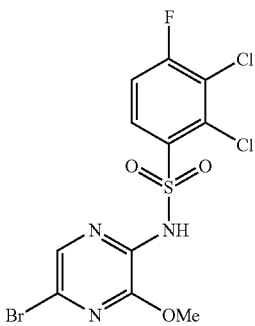

Prepared by the method of Example 1 (reaction performed at room temperature) using 5-bromo-3-methoxy-2-pyrazinamine (0.2 g) and 2,3-dichloro-4-fluorobenzenesulphonyl chloride (Example 185a) (0.31 g). Yield 0.042 g.

m/e 430 (M−1$^-$,100%)

$^1$H NMR (D6-DMSO) δ 8.16-8.12 (1H, m), 7.81 (1H, s), 7.68-7.64 (1H, m), 3.92 (3H, s).

MP 208-211° C.

EXAMPLE 186

2,3-Dichloro-N-[3-methoxy-5-(4-morpholinylmethyl)-2-pyrazinyl]benzenesulphonamide a) 2,3-Dichloro-N-(5-formyl-3-methoxy-2-pyrazinyl)benzenesulphonamide

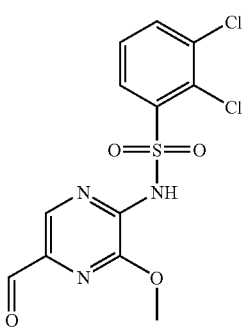

Prepared as for Example 107a using 2,3-dichloro-N-[5-(hydroxymethyl)-3-methoxy-2-pyrazinyl]benzenesulphonamide (Example 138) (0.6 g). Yield 0.53 g. Used directly.

b) 2,3-Dichloro-N-[3-methoxy-5-(4-morpholinylmethyl)-2-pyrazinyl]benzenesulphonamide

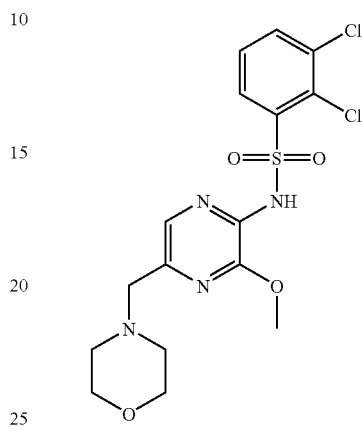

Prepared as for Example 107b using 2,3-dichloro-N-(5-formyl-3-methoxy-2-pyrazinyl)benzenesulphonamide (Example 186a) (0.26 g) and morpholine (3.7 mL). Yield 0.057 g.

m/e 433 (M+1$^+$, 100%)

$^1$H NMR (D6-DMSO) δ 8.12 (1H, d), 7.94(1H, d), 7.59 (1H, t), 4.20 (2H, s), 3.96 (3H, s), 3.85-3.65 (5H, m)

EXAMPLE 187

N-(3-Allyloxy-5-chloro-2-pyrazinyl)-2,3-dichlorobenzenesulphonamide

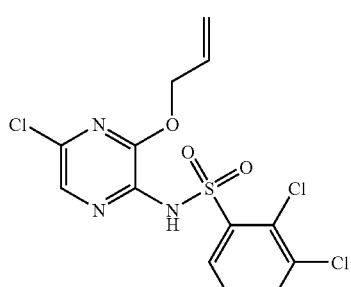

Prepared by the method of Example 31 using allyl alcohol (10 mL) as solvent and 2,3-dichloro-N-(3,5-dichloro-2-pyrazinyl)benzenesulphonamide (Example 74) (0.35 g). Yield 0.32 g.

m/e 393 (M−1$^+$, 100%)

$^1$H NMR (D6-DMSO) δ 11.80 (1H, br s), 8.08 (1H, dd), 7.96 (1H, dd), 7.82 (1H, dd), 7.58 (1H, t), 6.10-6.00 (1H, m), 5.49 (1H, dddd), 5.29 (1H, dddd), 4.86 (2H, dddd)

MP 145-146° C.

EXAMPLE 188

2,3-Dichloro-N-[5-chloro-3-(2-propynyloxy)-2-pyrazinyl]benzenesulphonamide

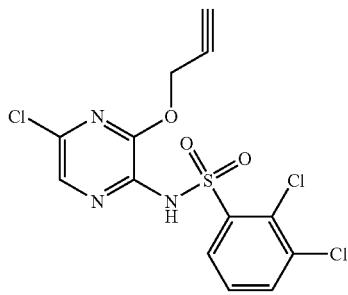

Prepared by the method of Example 31 using propargyl alcohol (0.3 g) and 2,3-dichloro-N-(3,5-dichloro-2-pyrazinyl)benzenesulphonamide (Example 74) (0.35 g). Yield 0.2 g.

m/e 390 (M–1+, 100%)

$^1$H NMR (D6-DMSO) δ 8.08 (1H, dd), 7.95 (1H, dd), 7.86 (1H, s), 7.58 (1H, t), 5.02 (2H, d), 3.65 (1H, t)

MP 138-139° C.

EXAMPLE 189

2,3-Dichloro-N-[3-(2-propynyloxy)-2-pyrazinyl)benzenesulphonamide

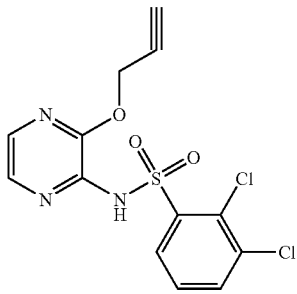

Prepared by the method of Example 28 using propargyl alcohol as solvent (3 mL), 2,3-dichloro-N-(3-chloro-2-pyrazinyl)benzenesulphonamide (Example 28) (0.3 g) and sodium hydride (0.2 g of a 60% dispersion in oil) at room temperature for 16 h. Yield 0.27 g.

m/e 356 (M–1+, 100%)

$^1$H NMR (D6-DMSO) δ 11.67 (1H, br s), 8.10 (1H, dd), 7.94 (1H, dd), 7.85 (1H, br), 7.72 (1H, br), 7.59 (1H, t), 5.01 (2H, d), 3.56 (1H, t)

MP 153-154° C.

EXAMPLE 190

2,3-Dichloro-N-(5-cyano-3-methoxy-2-pyrazinyl)benzenesulphonamide

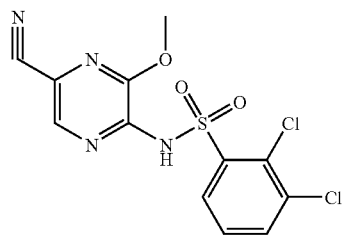

Prepared as for Example 78 using N-(5-bromo-3-methoxy-2-pyrazinyl)-2,3-dichlorobenzenesulphonamide (Example 8) (0.1 g). Yield 0.034 g.

m/e 357 (M–1+, 100%)

$^1$H NMR (D6-DMSO) δ 8.15 (1H, s), 8.14 (1H, dd), 7.95 (1H, dd), 7.59 (1H, t), 3.96 (3H, s)

MP 239-240° C.

EXAMPLE 191

2,3-Dichloro-N-{3-methoxy-5-[(2S)-pyrrolidin-2-ylmethoxy]-2-pyrazinyl}benzenesulfonamide hydrochloride

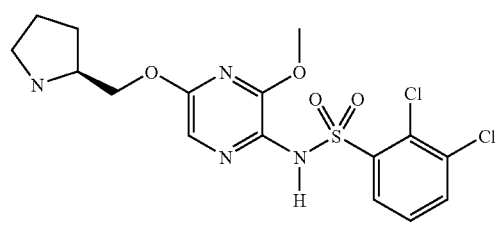

Procedure as for Example 115 using N-(5-bromo-3-methoxy-2-pyrazinyl)-2,3-dichloro-N-({2-[(trimethylsilyl)oxy]ethoxy}methyl)benzenesulphonamide (Example 55a) (0.5 g), tert-butyl (2S)-2-hydroxymethyl)pyrrolidine-1-carboxylate (0.603 g) and sodium hydride (0.12 g of a 60% dispersion in oil) in N-methylpyrrolidinone (20 mL). The adduct was deprotected with HCl (4M in dioxane) to afford the titled adduct (0.241 g) as a white solid.

m/e 433, 435 (M-HCl+1+, 100%)

$^1$H NMR (D6-DMSO) δ 10.92 (1H, s), 9.45 (1H, br), 8.93 (1H, br), 7.98 (1H, d), 7.93 (1H, d), 7.57(1H, d), 7.52 (1H, d), 4.53 (1H, dd), 4.37 (1H, dd), 3.94-3.86 (1H, m), 3.85 (3H, s), 3.22-3.18 (2H, m), 2.13-2.08 (1H, m), 1.99-1.86 (2H, m), 1.76-1.67 (1H, m).

EXAMPLE 192

2,3-Dichloro-N-{6-chloro-3-methoxy-5-[(2R)-2-pyrrolidinylmethoxy]-2-pyrazinyl}benzenesulphonamide Hydrochloride

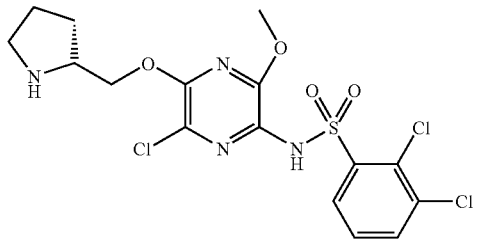

Procedure as for Example 115 using 2,3-dichloro-N-(5,6-dichloro-3-methoxy-2-pyrazinyl)-N-{[2-(trimethylsilyl)ethoxy]methyl}benzenesulphonamide (Example 66a) (0.29 g), tert-butyl (2S)-2-(hydroxymethyl)pyrrolidine-1-carboxylate (0.15 g) and sodium hydride (0.04 g of a 60% dispersion in oil) in N-methylpyrrolidinone (20 mL). The adduct was deprotected with HCl (4$\underline{M}$ in dioxane) to afford the titled adduct (0.2 g) as a white solid.

m/e 464 (M+H$^+$, 100%)

$^1$H NMR (D6-DMSO) δ 11.24 (1H, br s), 9.46 (1H, br s), 8.99 (1H, br s), 8.01 (1H, d), 7.96 (1H, d), 7.59 (1H, m), 4.61 (1H, dd), 4.46 (1H, dd), 3.95 (1H, br s), 3.85 (3H, s), 3.19 (2H, br s), 2.16-2.07 (1H, br s), 2.03-1.94 (1H, br s), 1.92-1.85 (1H, br s), 1.81-1.72 (1H, br s).

MP 200-204° C.

EXAMPLE 193

2,3-Dichloro-N-[3-methoxy-5-(2-pyridinylmethoxy)-2-pyrazinyl]benzenesulphonamide Hydrochloride

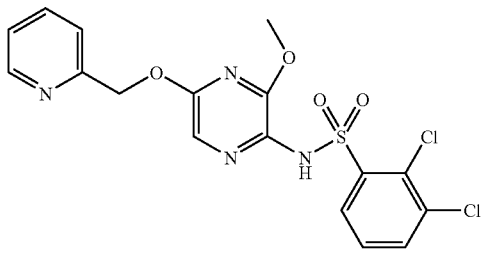

Procedure as for Example 115 using N-(5-chloro-3-methoxy-2-pyrazinyl)-2,3-dichloro-N-({2-[(trimethylsilyl)oxy]ethoxy}methyl)benzenesulphonamide (Example 115a) (0.5 g), pyridine-3-methanol (0.11 g) and sodium hydride (0.05 g of a 60% dispersion in oil) in N-methylpyrrolidinone (5 mL). Yield 0.23 g.

m/e 438 (M-1$^+$, 100%)

$^1$H NMR (D6-DMSO) δ 10.9 (1H, br s), 8.7 (1H, br s), 8.12 (1H, t), 7.99-7.92 (2H, m), 7.74 (1H, d), 7.61 (1H, s), 7.63-7.53 (2H, m), 5.54 (2H, s), 3.73 (3H, s).

MP 180-183° C.

EXAMPLE 194

2,3-Dichloro-N-(3-methoxy-6-methyl-2-pyrazinyl)benzenesulphonamide a) 3-Methoxy-6-methyl-2-pyrazinamine

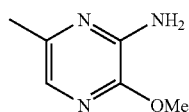

To a solution of 5-bromo-3-methoxy-6-methyl-2-pyrazinamine (Example 118c) (0.8 g) and ammonium formate (0.4 g) in methanol (20 mL) was added palladium on carbon (0.2 g) and the reaction mixture heated at reflux for 5h. After cooling to room temperature, the reaction mixture was filtered through a plug of celite, and the filtrate evaporated. The residue was partitioned between dichloromethane and water, and the organic phase dried (MgSO$_4$), filtered and evaporated to give the title compound as a white solid (0.44 g).

$^1$H NMR (D6-DMSO) δ 7.10 (1H, s), 6.15 (2H, br s), 3.83 (3H, s), 2.14 (3H, s)

b) 2,3-Dichloro-N-(3-methoxy-6-methyl-2-pyrazinyl)benzenesulphonamide

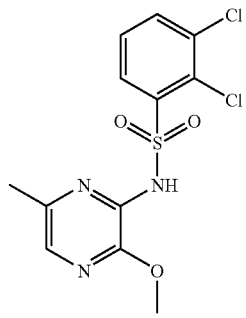

A solution of 3-methoxy-6-methyl-2-pyrazinamine (Example 194a) (0.050 g) and 2,3-dichlorobenzenesulphonyl chloride (0.098 g) in pyridine (0.3 mL) was stirred at room temperature for 18 h. Solvent was evaporated to give a residue which was purified by chromatography on silica gel eluting with dichloromethane/ethyl acetate/acetic acid (200:4:1) giving the title compound as a pale orange solid (0.071 g).

m/e 348/350 (M+H$^+$, 100%)

$^1$H NMR (D6-DMSO) δ 11.44 (1H, br s), 8.14 (1H, dd), 7.92 (1H, dd), 7.65 (1H, br s), 7.61 (1H, t), 3.85 (3H, s), 2.07 (3H, br s).

MP 50-60° C.

EXAMPLE 195

2,3-Dichloro-N-[3-methoxy-5-(1H-1,2,4-triazol-1-ylmethyl)-2-pyrazinyl]benzenesulphonamide a) 2,3-Dichloro-N-[5-(hydroxymethyl)-3-methoxy-2-pyrazinyl]-N-{[2-(trimethylsilyl)ethoxy]methyl}benzenesulphonamide

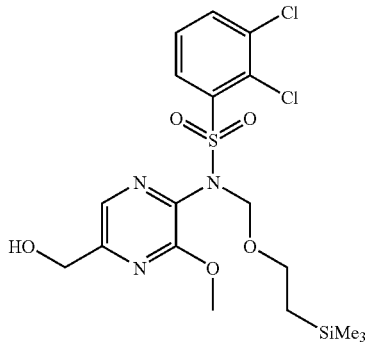

To a suspension of 2,3-dichloro-N-[5-(hydroxymethyl)-3-methoxy-2-pyrazinyl]-benzenesulphonamide (1.0 g) in dichloromethane (100 mL) was added diisopropylethylamine (0.57 mL) and 2-(trimethylsilyl)ethoxymethyl chloride (0.58 mL). The reaction mixture was stirred at room temperature for 0.5 h, then washed with water. The organic phase was dried ($MgSO_4$), filtered and evaporated to give a yellow oil. This was purified by chromatography on silica gel eluting with dichloromethane/ethyl acetate mixtures to give the title compound as a colourless oil (0.8 g).

$^1$H NMR ($CDCl_3$) δ 8.04 (1H, s), 7.99 (1H, d), 7.66 (1H, d), 7.28 (1H, t), 5.27 (2H, s), 4.74 (2H, d), 3.90 (3H, s), 3.78 (2H, m), 2.58 (1H, t), 0.85 (2H, m), 0.00 (9H, s).

b) 2,3-Dichloro-N-[3-methoxy-5-(1H-1,2,4-triazol-1-ylmethyl)-2-pyrazinyl]benzenesulphonamide

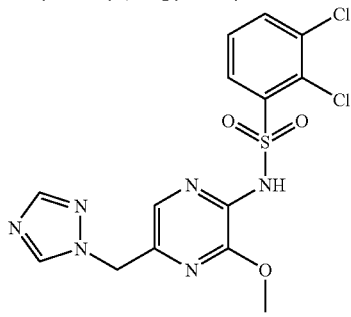

To a solution of 2,3-dichloro-N-[5-(hydroxymethyl)-3-methoxy-2-pyrazinyl]-N-{[2-(trimethylsilyl)ethoxy]methyl}benzenesulphonamide (Example 195a) (0.1 g) and triethylamine (0.056 mL) in dichloromethane (5 mL) at 0° C. was added methanesulphonyl chloride (0.019 mL) and the reaction mixture stirred at 0° C. for 1 h and room temperature for 1h. The solution was filtered through a plug of silica washing with ethyl acetate and concentrated in vacuo to give a colourless oil (0.082 g). This was dissolved in N,N-dimethylformamide (0.5 mL) and 1,2,4-triazole (0.013 g) and sodium carbonate (0.026 g) added. The reaction mixture was heated at 60° C. for 18 h, then partitioned between ethyl acetate and saturated aqueous ammonium chloride (5×). The organic phase was dried ($MgSO_4$), filtered and evaporated. The residue was dissolved in trifluoroacetic acid (2 mL) and dichloromethane (2 mL). After 20 min, removal of solvent in vacuo gave a residue which was purified by chromatography on silica gel eluting with ethyl acetate/acetic acid mixtures to give the title compound a pale yellow sollid (0.011 g).

m/e 413/415 (M−H$^-$, 100%)

$^1$H NMR ($CDCl_3$) δ 8.27 (2H, m), 8.0 (1H, br s), 7.94 (1H, s), 7.68 (1H, d), 7.58 (1H, br s), 7.41 (1H, t), 5.25 (2H, s), 3.97 (3H, s).

MP 95-105° C.

EXAMPLE 196

N-(3-(5-Aminomethyl-2-furanylmethoxy)-5-chloro-2-pyrazinyl)-2,3-dichloro-benzenesulphonamide

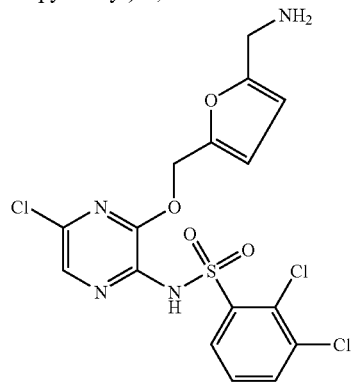

Prepared by the method of Example 31 using (5-aminomethyl-2-furanyl)methanol (0.2 g) and 2,3-dichloro-N-(3,5-dichloro-2-pyrazinyl)benzenesulphonamide (Example 74) (0.3 g). Purified by silica gel chromatography eluting with methanol/dichloromethane mixtures.

Yield 0.1 g.

m/e 463 (M+1$^+$, 100%)

$^1$H NMR (D6-DMSO) δ 8.25 (2H, br s), 7.92 (1H, dd), 7.61 (1H, dd), 7.35 (1H, t), 7.27 (1H, s), 6.66 (1H, d), 6.57 (1H, d), 5.19 (2H, s), 4.14 (2H, s)

MP 201-202° C.

EXAMPLE 197

N-(3-(5-Aminomethyl-2-furanylmethoxy)-2-pyrazinyl)-2,3-dichlorobenzenesulphonamide

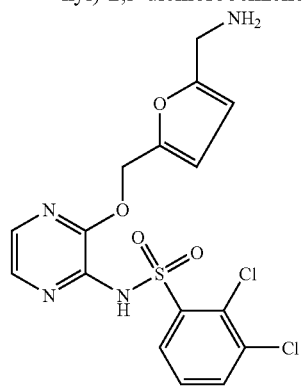

Prepared by the method of Example 28 using (5-aminomethyl-2-furanyl)methanol (0.2 g) and 2,3-dichloro-N-(3-chloro-2-pyrazinyl)benzenesulphonamide (Example 28) (0.3 g). Purified by silica gel chromatography eluting with methanol/dichloromethane mixtures. Yield 0.2 g m/e 427 (M−1$^+$, 100%).

¹H NMR (D6-DMSO) δ 8.40 (2H, br s), 7.96 (1H, dd), 7.60 (1H, dd), 7.35 (1H, t), 7.24 (1H, d), 7.15 (1H, d), 6.64 (1H, d), 6.57 (1H, d), 5.20 (2H, s), 4.13 (2H, s)

MP 199-201° C.

EXAMPLE 198

2,3-Dichloro-N-[3-methoxy-5-(2-propyn-1-yloxy)-2-pyrazinyl]benzenesulphonamide

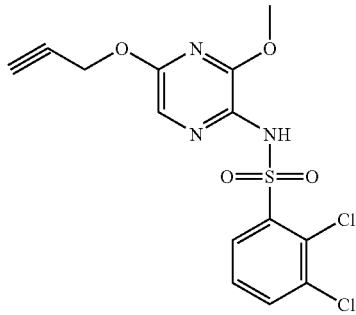

Procedure as for Example 115 using 2,3-dichloro-N-(5-chloro-3-methoxy-2-pyrazinyl)-N-({2-[(trimethylsilyl)oxy]ethoxy}methyl)benzenesulphonamide (Example 115a) (0.25 g), propargyl alcohol (0.025 mL) and sodium hydride (0.035 g of a 60% dispersion in oil) in N,N-dimethylformamide (5 mL). Yield 0.05 g.

m/e 388 (M+1$^+$, 100%)

¹H NMR (D6-DMSO) δ 10.90 (1H, s), 7.98-7.94 (2H, m), 7.55 (1H, t), 7.51 (1H, s), 4.97 (2H, d), 3.85 (3H, s), 3.56 (1H, t)

MP 110-112° C.

EXAMPLE 199

{[5-(2,3-Dichlorophenylsulfonylamino)-6-methoxy-2-pyrazinyl]oxy}acetic acid, methyl ester

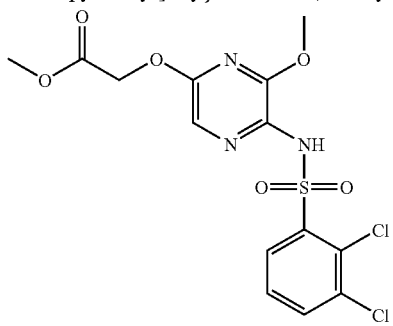

Procedure as for Example 115 using 2,3-dichloro-N-(5-chloro-3-methoxy-2-pyrazinyl)-N-({2-[(trimethylsilyl)oxy]ethoxy}methyl)benzenesulphonamide (Example 115a) (0.26 g), methyl glycolate (0.075 mL) and sodium hydride (0.035 g of a 60% dispersion in oil) in N,N-dimethylformamide (5 mL). Yield 0.1 g m/e 422 (M+1$^+$, 100%)

¹H NMR (D6-DMSO) δ 10.89 (1H, s), 7.99-7.92 (2H, m), 7.58-7.53 (2H, m), 4.92 (2H, s), 3.75 (3H, s), 3.68 (3H, s).

MP 185-190° C.

EXAMPLE 200

N-[5-(2,3-Dichlorophenylsulphonylamino)-6-methoxy-2-pyrazinyl]-2-hydroxyacetamide

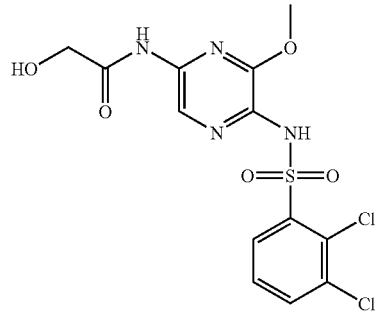

Procedure as for Example 115 using 2,3-dichloro-N-(5-chloro-3-methoxy-2-pyrazinyl)-N-({2-[(trimethylsilyl)oxy]ethoxy}methyl)benzenesulphonamide (Example 115a) (0.25 g), glycolamide (0.066 g) and sodium hydride (0.035 g of a 60% dispersion in oil) in N,N-dimethylformamide (5 mL). Yield 0.075 g.

m/e 407 (M+1$^+$, 100%)

¹H NMR (D6-DMSO) δ 11.23 (1H, br s), 9.77 (1H, s), 8.36 (1H, s), 8.05 (1H, dd), 7.94 (1H, dd), 7.58 (1H, t), 4.04 (2H, s), 3.86 (3H, s).

MP 153-155° C.

EXAMPLE 201

6-(2,3-Dichlorophenylsulphonylamino)-5-methoxy-2-pyrazinecarboxylic acid, methyl ester a) 6-chloro-3-methoxy-2-pyrazinamine

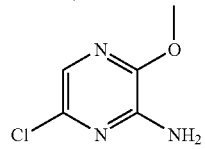

A mixture of 5-bromo-6-chloro-3-methoxy-2-pyrazinamine (Example 125a) (0.6 g), triethylamine (0.72 mL), 10% palladium on carbon (0.05 g) and ethyl acetate (50 mL) were hydrogenated at 0.5 bar until reaction was complete as judged by hydrogen uptake. The reaction mixture was filtered and washed with water (25 mL), dried (MgSO$_4$), filtered and evaporated to afford the sub-titled compound (0.33 g). Used Directly.

b) 6-Amino-5-methoxypyrazine-2-carboxylic acid methyl ester

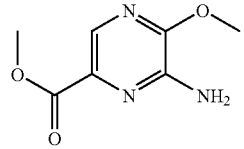

Prepared as for Example 113 using 6-chloro-3-methoxy-2-pyrazinamine (Example 201a) (0.35 g) heated at 120° C. for 3 h. Yield 0.3 g.

m/e 184 (M+1$^+$, 100%)

c) 6-(2,3-Dichlorophenylsulphonylamino)-5-methoxy-2-pyrazinecarboxylic acid, methyl ester

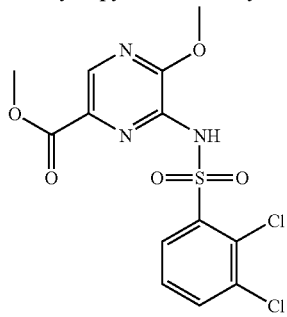

Prepared by the method of Example 1 (reaction performed at room temperature) using 6-amino-5-methoxypyrazine-2-carboxylic acid methyl ester (Example 201b) (0.3 g) and 2,3-dichlorobenzenesulphonyl chloride (0.4 g). Yield 0.15 g.
m/e 392 (M+1$^+$, 100%)
$^1$H NMR (D6-DMSO) δ 8.39 (1H, s), 8.25 (1H, dd), 7.93 (1H, dd), 7.65 (1H, t), 3.99 (3H, s), 3.77 (3H, s)
MP 90-92° C.

EXAMPLE 202

2,3-Dichloro-N-[6-(hydroxymethyl)-3-methoxy-2-pyrazinyl]benzenesulphonamide

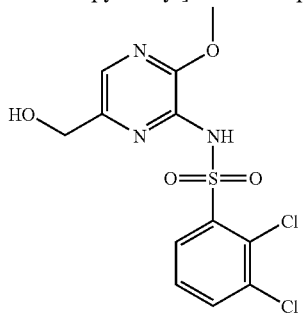

Prepared as for example 120 using 6-(2,3-dichlorophenylsulphonylamino)-5-methoxy-2-pyrazinecarboxylic acid, methyl ester (Example 201) (0.12 g). Yield 0.03 g.
m/e 364 (M+1$^+$, 100%)
$^1$H NMR (6-DMSO) δ 11.5 (1H, br s), 8.13 (1H, dd), 7.92 (1H, dd), 7.77 (1H, br s), 7.59 (1H, t), 5.25 (1H, br s), 4.19 (2H, s), 3.87 (3H, s).
MP 153-155° C.

EXAMPLE 203

2,3-Dichloro-N-(5-methanesulphonyl-3-methoxy-2-pyrazinyl)benzenesulphonamide

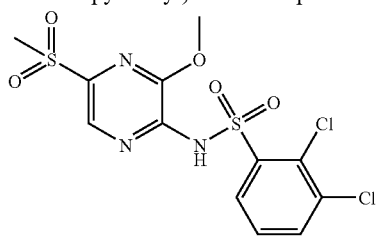

Oxone (potassium peroxymonosulphate) (0.6 g) was added to 2,3-dichloro-N-(3-methoxy-5-methylsulphanyl-2-pyrazinyl)benzenesulphonamide (Example 80) (0.3 g) in methanol (40 mL) and water (10 mL) and the mixture heated at 50° C. for 4 h. After cooling, the mixture was filtered and evaporated. Purified by silica gel chromatography eluting with ethyl acetate/iso-hexane mixtures containing 1% acetic acid to give the title compound.
Yield 0.2 g.
m/e 411 (M-1$^+$, 100%)
$^1$H NMR (CDCl$_3$) δ 8.33 (1H, s), 8.30 (1H, s), 8.23 (1H, br s), 7.72 (1H, dd), 7.47 (1H, t), 4.14 (3H, s), 3.11 (3H, s)
MP 237-238° C.

EXAMPLE 204

2-[5-(2,3-Dichlorobenzenesulphonylamino)-6-methoxy-2-pyrazinyloxy]-N,N-diethyl-acetamide

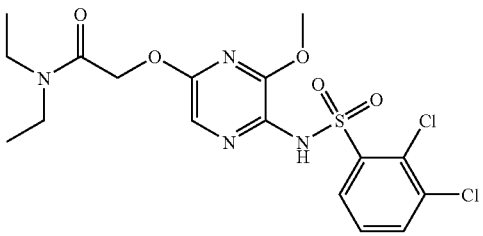

Prepared as for Example 115b using N-(5-bromo-3-methoxy-2-pyrazinyl)-2,3-dichloro-N-[{2-(trimethylsilanyl)ethoxy}methyl]benzenesulphonamide (Example 55a) (0.35 g) and N,N-diethyl-2-hydroxyacetamide (0.13 g). Yield 0.2 g
m/e 463 (M+1$^+$, 100%)
$^1$H NMR (CDCl$_3$) δ 8.22 (1H, dd), 7.68 (1H, dd), 7.52 (1H, s), 7.46 (1H, s), 7.37 (1H, t), 4.88 (2H, s), 3.92 (3H, s), 3.38 (2H, q), 3.30 (2H, q), 1.20 (3H, t), 1.11 (3H, t)
MP 117-118° C.

EXAMPLE 205

2,3-Dichloro-N-{5-[2-(dimethylamino)ethylsulphanyl]-3-methoxy-2-pyrazinyl}benzenesulphonamide

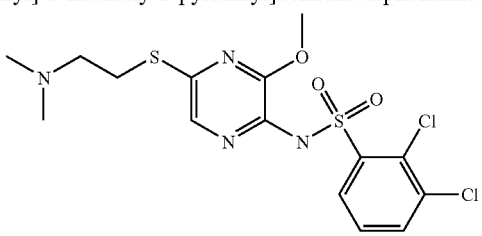

Prepared as for Example 101b using N-(5-bromo-3-methoxy-2-pyrazinyl)-2,3-dichloro-N-{[2-(trimethylsilanyl)ethoxy]methyl}benzenesulphonamide (Example 55a) (0.3 g) and 2-(dimethylamino)ethanthiol hydrochloride (0.2 g). Yield 0.25 g.
m/e 435(M-1$^+$, 100%)
$^1$H NMR (D6-DMSO) δ 8.05 (1H, dd), 7.95 (1H, dd), 7.71 (1H, s), 7.58 (1H, t), 3.98 (3H, s), 3.47 (2H, m), 3.28 (2H, m), 2.77 (6H, s)
MP 117-118° C.

EXAMPLE 206

2,3-Dichloro-N-(5-difluoromethyl-3-methoxy-2-pyrazinyl)benzenesulphonamide

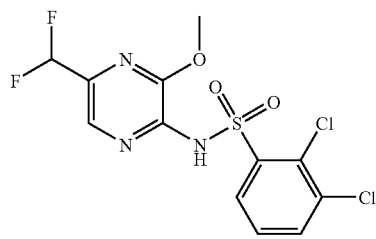

(Diethylamino)sulphur trifluoride (DAST) (0.15 g) and 2,3-dichloro-N-(5-formyl-3-methoxy-2-pyrazinyl)benzenesulphonamide (Example 186a) (0.3 g) in dichloromethane (20 mL) was stirred at room temperature for 4 h and then evaporated. Purified by silica gel chromatography eluting with ethyl acetate/iso-hexane mixtures to give the title compound.

Yield 0.06 g.

m/e 382(M−1+, 100%)

$^1$H NMR (D6-DMSO) δ 8.14 (1H, dd), 7.96 (1H, dd), 7.84 (1H, s), 7.60 (1H, t), 6.80 (1H, t), 3.95 (3H, s)

MP 117-118° C.

EXAMPLE 207

2,3-Dichloro-4-fluoro-N-(3-methoxy-2-pyrazinyl)benzenesulphonamide

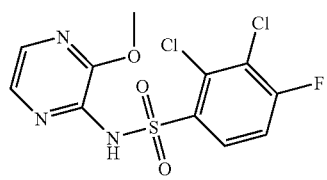

Sodium hydride (0.4 g of a 60% dispersion in oil) was added to a solution of 3-methoxy-2-pyrazinamine (0.25 g) in N-methylpyrrolidinone (10 mL). After 0.5 h, 2,3-dichloro-4-fluorobenzenesulphonyl chloride (Example 185a) (0.63 g) was added. After 16 h at room temperature the reaction mixture was quenched with 2M aqueous HCl, extracted with ethyl acetate, dried (MgSO$_4$) and evaporated. Purification was by silica gel chromatography eluting with ethyl acetate/iso-hexane mixtures. Yield 0.16 g.

m/e 350/352 (M−1−, 100%)

$^1$H NMR (D$_6$-DMSO) δ 8.16 (1H, dd), 7.78 (1H, br s), 7.68 (1H, t), 7.62 (1H, br s), 3.9 (3H, s)

MP 192-194° C.

EXAMPLE 208

2,3-Dichloro-N-{5-chloro-3-[1-(cyclopropyl)ethoxy-2-pyrazinyl}benzenesulphonamide

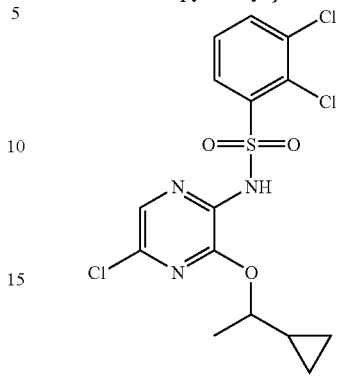

Prepared by the method of Example 31b using 1-(cyclopropyl)ethanol (0.1 g) and 2,3-dichloro-N-(3,5-dichloro-2-pyrazinyl)benzenesulphonamide (Example 74) (0.1 g). Yield 0.04 g.

m/e 422 (M+1+, 100%)

$^1$H NMR (D6-DMSO) δ 11.70-11.50 (1H, br s), 8.07 (1H, dd), 7.94 (1H, dd), 7.77 (1H, s), 7.59 (1H, t), 4.60-4.50 (1H, m), 1.33 (3H, d), 1.1-1.0 (1H, m), 0.6-0.3 (4H, m)

MP 161-162° C.

EXAMPLE 209

2,3-Dichloro-N-[5-chloro-3-(5-formyl-2-furanylmethoxy)-2-pyrazinyl]benzenesulphonamide a) [5-(1,3-Dimethyl-2-imidazolidinyl)-2-faranyl]methanol

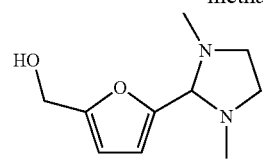

5-hydroxymethylfuran-2-carbaldehyde (5.0 g) and N,N'-dimethylethane-1,2-diamine (3.8 g) in toluene (100 mL) was heated under reflux using a Dean and Stark apparatus. After 12 h, the toluene was evaporated to give an oil. Yield 8.3 g. Used directly.

b) 2,3-Dichloro-N-[5-chloro-3-(5-formyl-2-furanylmethoxy)-2-pyrazinyl]benzenesulphonamide

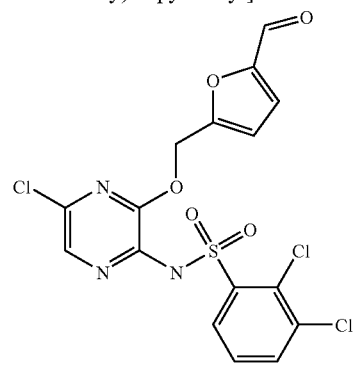

Prepared by the method of Example 31b (reaction heated at 60° C. for 4 h) using [5-(1,3-dimethyl-2-imidazolidinyl)-2- furanyl]methanol (2.3 g) and 2,3-dichloro-N-(3,5-dichloro-2-pyrazinyl)benzenesulphonamide (Example 74) (3.0 g). The reaction was quenched with 2M hydrochloric acid and left for 16 h. The solid product was collected. Purified by silica gel chromatography eluting with ethyl acetate/iso-hexane mixtures to give the title compound.

Yield 2.5 g.

m/e 460 (M+1⁺, 100%)

¹H NMR (D6-DMSO) δ 9.64 (1H, s), 8.06 (1H, dd), 7.94 (1H, dd), 7.87 (1H, s), 7.57 (2H, d+t), 6.93 (1H, d), 5.47 (2H, d)

EXAMPLE 210

2,3-Dichloro-N-[5-chloro-3-(5-cyclopropylaminomethyl-2-furanylmethoxy)-2-pyrazinyl]-benzenesulphonamide

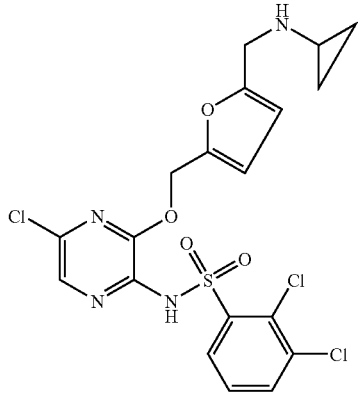

Prepared by the method of Example 107b using 2,3-dichloro-N-[5-chloro-3-(5-formyl-2-furanylmethoxy)-2-pyrazinyl]benzenesulphonamide (Example 209) (0.3 g) and cyclopropylamine (0.1 g). Yield 0.1 g.

m/e 503 (M−1⁺, 100%)

¹H NMR (D6-DMSO) δ 7.93 (1H, dd), 7.63 (1H, dd), 7.36 (1H, t), 7.30 (1H, s), 6.66 (1H, d), 6.63 (1H, d), 5.21 (2H, s), 4.34 (2H, s), 2.71 (1H, m), 0.76 (4H, m)

MP 175-176° C.

EXAMPLE 211

N-[5,6-bis-(Hydroxymethyl)-3-methoxy-2-pyrazinyl]-2,3-dichlorobenzenesulphonamide a) 2,3-Dichloro-N-(5,6-dicyano-3-methoxy-2-pyrazinyl)benzenesulphonamide

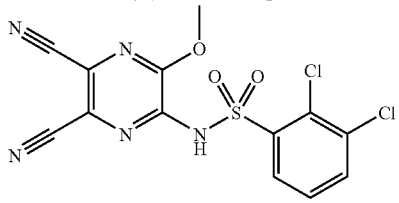

Prepared by the method outlined in Example 1 using 5-amino-6-chloro-2,3-dicyanopyrazine (1.8 g) and 2,3-dichlorobenzenesulfonyl chloride (2.7 g). The adduct was reacted by the method outlined in example 31b using sodium methoxide to afford the sub-titled compound that was used directly.

m/e 382, 383 (M−1⁺, 100%)

b) 5-{[(2,3-Dichlorophenyl)sulphonyl]amino}-6-methoxypyrazine-2,3-dicarboxylic acid, dimethyl ester

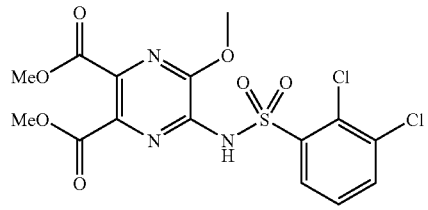

The crude product from above (Example 211a) was dissolved in 10% aqueous sodium hydroxide solution and heated under reflux for 10 hours. The reaction mixture was cooled, concentrated and the residue was treated with thionyl chloride (30 mL) and refluxed for 1 hour, cooled and concentrated, azeotroping with dry toluene. The resulting residue was dissolved in methanol (30 mL) and allowed to stand for 10 hours and concentrated to afford the sub-titled compound that was used directly.

m/e 448, 450 (M−1⁺, 100%)

c) N-[5,6-bis-(Hydroxymethyl)-3-methoxy-2-pyrazinyl]-2,3-dichlorobenzenesulphonamide

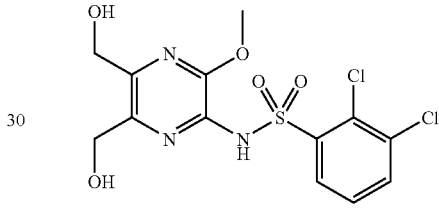

To a solution of 5-{[(2,3-dichlorophenyl)sulphonyl]amino}-6-methoxypyrazine-2,3-dicarboxylic acid, dimethyl ester (Example 211b, 0.5 g) dissolved in anhydrous tetrahydrofuran (20 mL) at 0° C. was added a solution of lithium triethylborohydride (Super is hydride®) (5.55 mL of a 1M solution in tetrahydrofuran) and the resulting solution was stirred for 1 hour. The reaction was quenched by the addition of 1N hydrochloric acid (10 mL) and extracted into ethyl acetate (2×20 mL). The combined extracts were dried (MgSO₄), filtered and concentrated to afford an oil that was purified by chromatography on silica gel eluting with ethyl acetate/dichloromethane mixtures to afford the titled compound (0.201 g) as a foam.

m/e 392, 394 (M−1⁺, 100%)

¹H NMR (CDCl₃) δ 8.30 (1H, d); 7.91 (1H, br s), 7.71 (1H, d), 7.46 (1H, t), 4.59 (2H, s), 4.50 (2H, s), 4.0 (3H, s)

EXAMPLE 212

N-[3-[(2-amino-4-oxazolyl)methoxy]-5-chloro-2-pyrazinyl]-2,3-dichlorobenzenesulphonamide a) (4-Hydroxymethyl-2-oxazolyl)carbamic acid tert-butyl ester

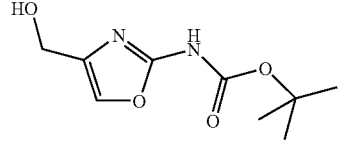

Prepared by the method of Example 120 using 2-{bis[(1,1-dimethylethoxy)carbonyl]amino}-4-oxazolcarboxylic acid, ethyl ester (0.65 g) and sodium triethylborohydride (5.5 mL of a 1M solution in tetrahydrofuran). Yield 0.24 g. Used directly.

b) N-[3-[(2-amino-4-oxazolyl)methoxy]-5-chloro-2-pyrazinyl]-2,3-dichlorobenzenesulphonamide

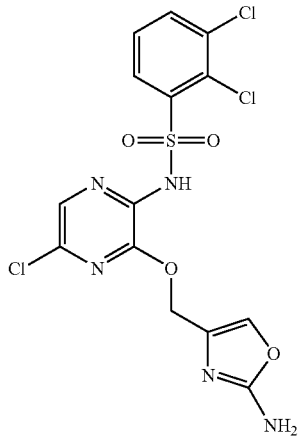

Prepared by the method of Example 112 using (4-hydroxymethyl-2-oxazolyl)carbamic acid tert-butyl ester (Example 212a) (0.12 g) and 2,3-dichloro-N-(3,5-dichloro-2-pyrazinyl)benzenesulphonamide (Example 74) (0.21 g). Purification was by silica gel chromatography eluting with ethyl acetate/iso-hexane mixtures to give the title compound with the BOC (tert-butyl carbonyl) attached (0.11 g). This compound was dissolved in trifluoroacetic acid (1.5 mL) and dichloromethane (1.5 mL). After 2 h, the solution was evaporated. Purification was by silica gel chromatography eluting with ethyl acetate/iso-hexane mixtures to give the title compound. Yield 0.08 g.

m/e 450 (M+1$^+$, 100%)

$^1$H NMR (D6-DMSO) δ 8.04 (1H, dd), 7.91 (1H, dd), 7.80 (1H,s), 7.55 (1H, t), 7.49 (1H, s), 6.71 (2H, br s), 5.10(2H, s).

MP 137° C.

Pharmacological Analysis

FMAT Whole Cell Binding Assay

Cells

CHO—K1 cells stably expressing the human recombinant CCR4 receptor (Euroscreen; Brussels, Belgium) were cultured in NUT.MIX.F__12(HAM) medium with glutamax-1, containing 10% (v/v) foetal bovine serum and 400 μg ml$^{-1}$ geneticin.

Cells were harvested at approximately 70% confluence by treatment with a cell dissociation buffer, and seeded at 5×10$^3$ cells/100 μl culture medium into wells of a black Costar clear-bottomed 96-well microtitre plates. Plates were incubated overnight at 37° C. in 5% $CO_2$ and used the following day.

Assay

Before use, the cell plates were washed twice with 100 μl Hanks balanced salt solution (HBSS). To each well was then added 65 μl of HBSS, 10 μL of 10% DMSO in HBSS±test compound and then 25 μL of 2.8 nM FB-MDC (Applied Biosystems). This fluorescent probe was prepared from a 10 μM stock in 0.08% (v/v) TFA/16% (v/v) acetonitrile, diluted into HBSS.

After two hours incubation in the dark at room temperature, the plates were analysed in an FMAT8100 reader (Applied Biosystems) to measure fluorescence that was associated with binding of FB-MDC to the cells. Compound activity was determined as an pIC$_{50}$ [log(concentration of compound that results in 50% inhibition)], comparing fluorescence in control and background wells.

Typical Data

Fluorescence (ctrl)=1200

Fluorescence (bkg)=0

The compounds of the examples all have a pIC$_{50}$ of greater than 5.0.

Data for specific compounds is given below.

|  |  | Mean |
|---|---|---|
| Example 112 | pIC$_{50}$ | 9.5 |
| Example 119 | pIC$_{50}$ | 7.2 |
| Example 186 | pIC$_{50}$ | 6.2 |

The invention claimed is:

1. A compound of formula (I) or a pharmaceutically acceptable salt thereof:

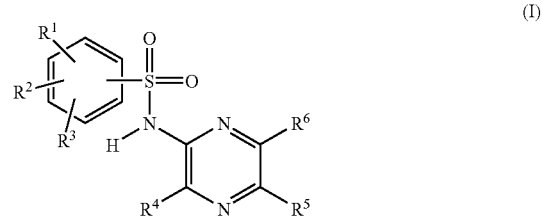

(I)

in which:

R$^1$, R$^2$ and R$^3$ are independently hydrogen, chlorine, fluorine, or cyano;

R$^4$ is halogen, $CO_2R^{12}$ or $C_{1-6}$ alkoxy where the alkyl group may be substituted with 1-3 fluorine atoms or a cyano group;

R$^5$ and R$^6$ are independently hydrogen, cyano, halogen, $CO_2R^{12}$, $CONR^{14}R^{15}$; $C_{1-6}$ alkyl optionally substituted by hydroxy, $NR^{14}R^{15}$, or 1-3 fluorines;

$C_{3-6}$ alkynyl or $C_{3-6}$ alkenyl optionally branched and optionally substituted with 1-3 groups selected from hydroxy, cyano, halogen and =O;

X—R$^{12}$; X—(CH$_2$)nCO$_2$R$^{12}$; X—(CH$_2$)nCONR$^{14}$R$^{15}$; X—(CH$_2$)nCN; X—(CH$_2$)qOR$^{12}$; (CH$_2$)nOR$^{12}$;

X—(CH$_2$)qNHC(O)NHR$^{12}$; X—(CH$_2$)qNHC(O)R$^{12}$;

X—(CH$_2$)qNHS(O)$_2$R$^{12}$; X—C$_{3-6}$alkenyl; X—C$_{3-6}$alkynyl;

n is 1,2, 3, 4 or 5;

q is 2, 3,4, 5 or 6;

X is NR$^{13}$, O, S, S(O), S(O)$_2$;

R$^{12}$ and R$^{13}$ are independently hydrogen or C$_{1-6}$ alkyl where the alkyl group may be substituted with 1-3 fluorine atoms; and R$^{14}$ and R$^{15}$ are independently hydrogen, C$_{1-6}$ alkyl, or (CH$_2$)qOH.

2. A compound according to claim 1 in which R$^1$ and R$^2$ are chloro at the 2- and 3-positions of the phenyl ring and R$^3$ is hydrogen.

3. A compound according to claim 1 or 2 in which R$^4$ is C$_{1-6}$ alkoxy.

4. A compound according to claim 1 in which $R^5$ is hydrogen, halogen, -$C_{1-6}$ alkyl, $CH_2OH$, cyano or 2-aminoethanethiol.

5. A compound according to claim 1 in which $R^6$ is hydrogen, $C_{1-6}$ alkyl, $CH_2OH$ or halogen.

6. A compound according to claim 1 in which is:
2,3-Dichloro-N-(3-methoxy-5-methyl-2-pyrazinyl)-benzenesulphonamide
N-(6-Chloro-3-methoxy-2-pyrazinyl)-2,3,4-tifluorobenzenesulphonamide 3-Chloro-N-(6-chloro-3-methoxy-2-pyrazinyl)-2-methylbenzenesulphonamide
2,3-Dichloro-N-(6-chloro-3-methoxy-2-pyrazinyl)benzenesulphonamide
2,3-Dichloro-N-(5-chloro-3-methoxy-2-pyrazinyl)benzenesulphonamide
N-(5-Bromo-3-methoxy-2-pyrazinyl)-2,5-dichlorobenzenesulphonamide
N-(5-Bromo-3-methoxy-2-pyrazinyl)-3,5-dichlorobenzenesulphonamide
N-(5-Bromo-3-methoxy-2-pyrazinyl)-2,3-dichlorobenzenesulphonamide
N-(5-Bromo-3-methoxy-2-pyrazinyl)-2,4-dichlorobenzenesulphonamide
N-(5-Bromo-3-methoxy-2-pyrazinyl)-3,4-dichlorobenzenesulphonamide
N-(5-Bromo-3-methoxy-2-pyrazinyl)-4-chlorobenzenesulphonamide
N-(5-Bromo-3-methoxy-2-pyrazinyl)-3-chlorobenzenesulphonamide
N-(3-Methoxy-5-methyl-2-pyrazinyl)-2-fluorobenzenesulphonamide
N-(3-Methoxy-5-methyl-2-pyrazinyl)benzenesulphonamide
N-(3-Methoxy-5-methyl-2-pyrazinyl)-3-fluorobenzenesulphonamide
2-[[(3-Methoxy-5-methyl-2-pyrazinyl)amino]sulphonyl]benzonitrile
N-(5-Bromo-3-methoxy-2-pyrazinyl)benzenesulphonamide
2-Chloro-N-(6-chloro-3-methoxy-2-pyrazinyl)benezenesulphonamide
4-Chloro-N-(6-chloro-3-methoxy-2-pyrazinyl)benezenesulphonamide
N-(6-Chloro-3-methoxy-2-pyrazinyl)-2,4-dichlorobenezenesulphonamide
N-(6-Chloro-3-methoxy-2-pyrazinyl)-3,4-dichlorobenezenesulphonamide
2-Chloro-N-(3-methoxy-5-methyl-2-pyrazinyl)benezenesulphonamide
3-Chloro-N-(3-methoxy-5-methyl-2-pyrazinyl)benezenesulphonamide
4-Chloro-N-(3-methoxy-5-methyl-2-pyrazinyl)benezenesulphonamide
2,4-Dichloro-N-(3-methoxy-5-methyl-2-pyrazinyl)benezenesulphonamide
3,4-Dichloro-N-(3-methoxy-5-methyl-2-pyrazinyl)benezenesulphonamide
2-Chloro-N-(5-chloro-3-methoxy-2-pyrazinyl)benezenesulphonamide
3-Chloro-N-(5-chloro-3-methoxy-2-pyrazinyl)benezenesulphonamide
4-Chloro-N-(5-chloro-3-methoxy-2-pyrazinyl)benezenesulphonamide
N-(5-Chloro-3-methoxy-2-pyrazinyl)-2,4-dichlorobenezenesulphonamide
2,3-Dichloro-N-[3,5-dimethoxy-2-pyrazinyl]benzenesulphonamide
3-Chloro-N-(5,6-dichloro-3-methoxy-2-pyrazinyl)-2-methylbenzenesulphonamide
2,3-Dichloro-N-(5,6-dichloro-3-methoxy-2-pyrazinyl)benzenesulphonamide
2-Chloro-N-(5,6-dichloro-3-methoxy-2-pyrazinyl)benzenesulphonamide
3-Chloro-N-(5,6-dichloro-3-methoxy-2-pyrazinyl)benzenesulphonamide
4-Chloro-N-(5,6-dichloro-3-methoxy-2-pyrazinyl)benzenesulphonamide
2,4-Dichloro-N-(5,6-dichloro-3-methoxy-2-pyrazinyl)benzenesulphonamide
3,4-Dichloro-N-(5,6-dichloro-3-methoxy-2-pyrazinyl)benzenesulphonamide
2,3-Dichloro-N-(3-methoxy-5,6-dimethyl-2-pyrazinyl)benzenesulphonamide
2,3-Dichloro-N-(6-chloro-3,5-dimethoxy-2-pyrazinyl)benzenesulphonamide
2,3-Dichloro-N-[6-chloro-5-(2-hydroxyethylamino)-3-methoxy-2-pyrazinyl]benzenesulphonamide
2,3-Dichloro-N-[6-chloro-5-dimethylamino-3-methoxy-2-pyrazinyl]benzenesulphonamide
2,3-Dichloro-N-[6-chloro-3-methoxy-5-(2-methoxyethoxy)-2-pyrazinyl]benzenesulphonamide
2,3-Dichloro-N-[6-chloro-5-hydroxy-3-methoxy-2-pyrazinyl]benzenesulphonamide
2,3-Dichloro-N-(3,5-dichloro-2-pyrazinyl)benzenesulphonamide
2,3-Dichloro-N-{6-chloro-3-methoxy-5-([2-methoxyethyl)amino]-2-pyrazinyl}benzenesulphonamide
N-{2-[3-Chloro-5-(2,3-dichlorobenzenesulphonylamino)-6-methoxy-2-pyrazinylamino]ethyl}acetamide
2,3-Dichloro-N-(6-chloro-3-methoxy-5-methylamino-2-pyrazinyl)benzenesulphonamide
2,3-Dichloro-N-(3-methoxy-5-methylsulphanyl-2-pyrazinyl)benzenesulphonamide
-[5-(2,3-Dichlorobenzenesulphonylamino)-6-methoxy-2-pyrazinylsulphanyl]acetic acid methyl ester
[5-(2,3-Dichlorobenzenesulphonylamino)-6-methoxy-2-pyrazinylsulphanyl]acetic acid
2,3-Dichloro-N-[5-chloro-3-(2-methylsulphanylethoxy)-2-pyrazinyl]benzenesulphonamide
N-(3-Butoxy-5-chloro-2-pyrazinyl)-2,3-dichlorobenzenesulphonamide
N-[5-Bromo-6-chloro-2-pyrazinyl]-2,3-dichlorobenzenesulphonamide
5-(2,3-Dichlorobenzenesulphonylamino)-6-methoxypyrazine-2-carboxylic acid, methyl ester
2,3-Dichloro-N-[5-(1-hydroxy-1-methylethyl)-3-methoxy-2-pyrazinyl]benzenesulphonamide
N-[5-(2-Aminoethoxy)-3-methoxy-2-pyrazinyl]-2,3-dichlorobenzenesulphonamide
N-{5-[(2-Aminoethyl)thio]-6-chloro-3-methoxy-2-pyrazinyl}-2,3-dichlorobenzenesulfonamide
3-[(5-{[(2,3-Dichlorophenyl)sulphonyl]amino}-6-methoxy-2-pyrazinyl)thio]propanoic acid, methyl ester
2,3-Dichloro-N-[5-bromo-3-methoxy-6-methyl-2-pyrazinyl)benzenesulphonamide
5-(2,3-Dichlorobenzenesulphonylamino)-6-methoxy-3-methylpyrazine-2-carboxylic acid, methyl ester
2,3-Dichloro-N-[5-(hydroxymethyl)-3-methoxy-6-methyl-2-pyrazinyl)benzenesulphonamide
3-Chloro-N-(5-chloro-3-methoxy-2-pyrazinyl)-2-fluorobenzenesulphonamide
3-{[(2,3-Dichlorophenyl)sulphonyl]amino}pyrazine-2-carboxylic acid, methyl ester N-(5-Bromo-6-chloro-3-methoxy-2-pyrazinyl)-2,3-dichlorobenzenesulphonamide
3-Chloro-5-{[(2,3-dichlorophenyl)sulphonyl]amino}-6-methoxypyrazine-2-carboxylic acid, methyl ester
2,3-Dichloro-N-[6-chloro-5-(hydroxymethyl)-3-methoxypyrazin-2-yl]benzenesulphonamide
2,3-Dichloro-N-[6-chloro-3-methoxy-5-(methoxymethyl)-2-pyrazinyl]benzenesulphonamide
2-Chloro-N-(5-chloro-3-methoxy-2-pyrazinyl)-3-fluorobenzenesulphonamide
2-Chloro-3-fluoro-N-(3-methoxy-2-pyrazinyl)benzenesulphonamide
2,3-Dichloro-N-[5-(hydroxymethyl)-3-methoxy)-2-pyrazinyl]benzenesulphonamide
N-(5-Allyloxy-3-methoxy-2-pyrazinyl)-2,3-dichlorobenzenesulphonamide
2,3-Dichloro-N-[5-(3-hydroxy-1-propynyl)-3-methoxy-2-pyrazinyl]benzenesulphonamide
N-[5-Bromo-3-(pentyloxy)-2-pyrazinyl]-2,3-dichlorobenzenesulphonamide
N-[5-Bromo-3-(propyloxy)-2-pyrazinyl]-2,3-dichlorobenzenesulphonamide
N-[5-Bromo-3-(2-methoxyethoxy)-2-pyrazinyl]-2,3-dichlorobenzenesulphonamide
N-[5-Bromo-3-(2-ethoxyethoxy)-2-pyrazinyl]-2,3-dichlorobenzenesulphonamide
N-[5-Bromo-3-(2-fluoroethoxy)-2-pyrazinyl]-2,3-dichlorobenzenesulphonamide
N-[5-Bromo-3-[2-(methylamino)ethoxy]-2-pyrazinyl]-2,3-dichlorobenzenesulphonamide
2,3-Dichloro-N-(5-ethoxy-3-methoxy-2-pyrazinyl)benzenesulphonamide
2-[5-(2,3-Dichlorobenzenesulphonylamino)-6-methoxy-2-pyrazinylsulphanyl]-N-methylacetamide
2-[5-(2,3-Dichlorobenzenesulphonylamino)-6-methoxy-2-pyrazinylsulphanyl]acetamide
2,3-Dichloro-N-[5-cyanomethylsulphanyl-3-methoxy-2-pyrazinyl]benzenesulphonamide
N-[5-(2-Aminoethylsulphanyl)-3-methoxy-2-pyrazinyl]-2,3-dichlorobenzenesulphonamide
2,3-Dichloro-N-[5-(2-hydroxyethylsulphanyl)-3-methoxy-2-pyrazinyl]benzenesulphonamide
2,3-Dichloro-N-{5-[2-(ethylureido)ethylsulphanyl]-3-methoxy-2-pyrazinyl}benzenesulphonamide
N-(5-Bromo-3-methoxypyrazinyl)-2-cyanobenzenesulphonamide
N-(5-Bromo-3-methoxypyrazinyl)-2,3-dichloro-4-fluorobenzenesulphonamide
N-(3-Allyloxy-5-chloro-2-pyrazinyl)-2,3-dichlorobenzenesulphonamide
2,3-Dichloro-N-[5-chloro-3-(2-propynyloxy)-2-pyrazinyl]benzenesulphonamide
2,3-Dichloro-N-[3-(2-propynyloxy)-2-pyrazinyl)benzenesulphonamide
2,3-Dichloro-N-(5-cyano-3-methoxy-2-pyrazinyl)benzenesulphonamide
2,3-Dichloro-N-(3-methoxy-6-methyl-2-pyrazinyl)benzenesulphonamide
2,3-Dichloro-N-[3-methoxy-5-(2-propyn-1yloxy)-2-pyrazinyl]benzenesulphonamide
{[5-(2,3-Dichlorophenylsulfonylamino)-6-methoxy-2-pyrazinyl]oxy}acetic acid, methyl ester
N-[5-(2,3-Dichlorophenylsulphonylamino)-6-methoxy-2-pyrazinyl]-2-hydroxyacetamide
6-(2,3-Dichlorophenylsulphonylamino)-5-methoxy-2-pyrazinecarboxylic acid, methyl ester
2,3-Dichloro-N-[6-(hydroxymethyl)-3-methoxy-2-pyrazinyl]benzenesulphonamide
2,3-Dichloro-N-(5-methanesulphonyl-3-methoxy-2-pyrazinyl)benzenesulphonamide
2-[5-(2,3-Dichlorobenzenesulphonylamino)-6-methoxy-2-pyrazinyloxy]-N,N-diethyl-acetamide
2,3-Dichloro-N-{5-[2-(dimethylamino)ethylsulphanyl]-3-methoxy-2-pyrazinyl}benzenesulphonamide
2,3-Dichloro-N-(5-difluoromethyl-3-methoxy-2-pyrazinyl)benzenesulphonamide
2,3-Dichloro-4-fluoro-N-(3-methoxy-2-pyrazinyl)benzenesulphonamide, or
N-[5,6-bis-(Hydroxymethyl)-3-methoxy-2-pyrazinyl]-2,3-dichlorobenzenesulphonamide
or a pharmaceutically acceptable salt thereof.

7. A process for the preparation of compound (I) which comprises:
(a) reaction, of a compound of formula (II):

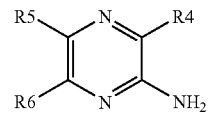

where $R^4$, $R^5$ and $R^6$ are as defined in formula (I) or are protected derivatives thereof with a compound of formula (III):

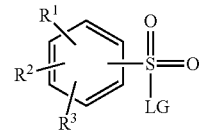

where $R^1$, $R^2$ and $R^3$ are as defined in formula (I) or are protected derivatives thereof and LG is a leaving group, or (b) for compounds where $R^4$ is $C_{1-6}$ alkoxy
treating a compound of the formula (VI), where LG is a leaving group:

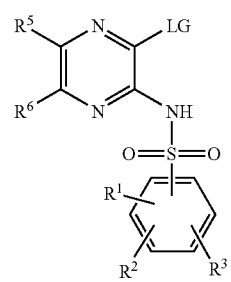

with a compound of formula $R^4$-H (V) in the presence of a suitable base,
and optionally thereafter process (a) or (b)
removing any protecting groups,
converting a compound of formula (I) to a further compound of formula (I)
forming a pharmaceutically acceptable salt.

8. A pharmaceutical composition comprising a compound of formula (I), or a pharmaceutically acceptable salt thereof, as claimed in claim 1 in association with a pharmaceutically acceptable adjuvant, diluent or carrier.

9. A process for the preparation of a pharmaceutical composition as claimed in claim 2 which comprises mixing a compound of formula (I), or a pharmaceutically acceptable salt thereof, as claimed in claim 1 with a pharmaceutically acceptable adjuvant, diluent or carrier.

10. A compound according to claim 1 which is 2,3-dichloro-N-(3-methoxy-2-pyrazinyl)benzenesulphonamide or a pharmaceutically acceptable salt thereof.

11. A compound according to claim 1 which is 2,3-dichloro-N-[5-(hydroxymethyl)-3-methoxy-6-methyl-2-pyrazinyl)benzenesulphonamide or a pharmaceutically acceptable salt thereof.

12. A compound according to claim 1 which is 2,3-dichloro-N-[6-chloro-5-(hydroxymethyl)-3-methoxy-pyrazin-2-yl]benzenesulphonamide or a pharmaceutically acceptable salt thereof.

13. A compound according to claim 1 which is 2,3-dichloro-N-[6-chloro-3-methoxy-5-(methoxymethyl)-2-pyrazinyl]benzenesulphonamide or a pharmaceutically acceptable salt thereof.

14. A compound according to claim 1 which is 2,3-dichloro-N-[5-(hydroxymethyl)-3-methoxy)-2-pyrazinyl]benzenesulphonamide or a pharmaceutically acceptable salt thereof.

* * * * *

UNITED STATES PATENT AND TRADEMARK OFFICE
CERTIFICATE OF CORRECTION

PATENT NO. : 7,662,825 B2
APPLICATION NO. : 10/501510
DATED : February 16, 2010
INVENTOR(S) : Baxter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1123 days.

Signed and Sealed this

Thirtieth Day of November, 2010

David J. Kappos
*Director of the United States Patent and Trademark Office*